(12) United States Patent
Suzuki et al.

(10) Patent No.: US 6,455,708 B1
(45) Date of Patent: Sep. 24, 2002

(54) PROCESSES FOR THE PREPARATION OF 4-SUBSTITUTED BENZOPYRAN DERIVATIVES

(75) Inventors: Yukio Suzuki; Takenori Ishizawa; Vladimir A. Khlebnikov, all of Shizouka; Masashi Watanabe, Tokyo, all of (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/787,673

(22) PCT Filed: Sep. 30, 1999

(86) PCT No.: PCT/JP99/05387

§ 371 (c)(1),
(2), (4) Date: Mar. 21, 2001

(87) PCT Pub. No.: WO00/18754

PCT Pub. Date: Apr. 6, 2000

(30) Foreign Application Priority Data

Sep. 30, 1998 (JP) ............................................. 10-277561
Sep. 30, 1998 (JP) ............................................. 10-277952
Sep. 30, 1998 (JP) ............................................. 10-278741

(51) Int. Cl.[7] ............................................. C07D 311/68
(52) U.S. Cl. ............................................. 549/404
(58) Field of Search ......................................... 549/404

(56) References Cited

FOREIGN PATENT DOCUMENTS

JP        07188210    *   7/1995
WO        wo 92/20671 *  11/1992

OTHER PUBLICATIONS

Fenwick, A, Tetrahedron Letters, 1993, 34(11), 1815–1818.*

Plevyak et al., "Selective Palladium–Catalyzed Vinylic Substitutions with Bromoiodo Aromatics", *J. Org. Chem.*, 1979, pp. 4078–4080, vol. 44, No. 23.

Willstaedt, "Über Brom–Addition an substituierte Zimtasäaren", Chem. Ber., 1931, pp. 2688–2695, vol. 64.

M. Yoshida et al., "Synthesis of Aryl Substituted Epihalohydrin Derivatives", Heterocycles, 1992, pp. 507–510, vol. 33, No. 2.

* cited by examiner

*Primary Examiner*—Ceila Chang
*Assistant Examiner*—Andrea D. Small
(74) *Attorney, Agent, or Firm*—Browdy and Neimark, P.L.L.C.

(57) ABSTRACT

Starting, for example, from 1-fluoro-2-fluoromethyl-3-butyn-2-yl 4-trifluoromethylphenyl; ether, N-(2-cyanoethyl)-5-fluoro-4-fluoromethyl-4-(4-trifluoromethylphenoxy)-2-pentynamide is produced and then cyclized to synthesize 2,2-bis(fluoromethyl)-N-(2-cyanoethyl)-6-trifluoromethyl-2H-1-benzopyran-4-carboxamide. The invention processes for producing 4-substituted benzopyran derivatives involve fewer steps, feature greater safety and allow for easier purification than the prior art processes.

10 Claims, No Drawings

US 6,455,708 B1

PROCESSES FOR THE PREPARATION OF 4-SUBSTITUTED BENZOPYRAN DERIVATIVES

REFERENCE TO RELATED APPLICATIONS

The present application is the national stage under 35 U.S.C. §371 of international application PCT/JP99/05387, filed Sep. 30, 199 which designated the United States, and which application was not published in the English language.

TECHNICAL FIELD

This invention relates to novel processes for producing 4-substituted benzopyran derivatives useful as medicines, agrichemicals and cosmetics, as well as intermediates for their synthesis and processes for producing such intermediates.

BACKGROUND ART

One of the prior art techniques known in the field contemplated by the invention is a process for synthesizing 4-substituted benzopyran derivatives via 4-bromobenzopyran drivatives (JPA Hei 7-188210).

According to JPA Hei 7-188210, a compound represented by the general formula (XVIII) (the chemical formulae embraced by the general formula (XVIII) are set forth in the List of Chemical Formulae at the end of the specification; all the chemical formulae referred to hereinafter are collectively set forth in the List of Chemical Formulae at the end of the specification) is reacted with carbon monoxide and amine in the presence of a palladium catalyst to give an amide form represented by the general formula (XXVI).

A method generally known to be applicable in the synthesis of benzopyrans is by subjecting a compound of the general formula (D) to thermal cyclization reaction to give a compound of the general formula (E) (see, for example, Australian Journal Chemistry, 1971, Vol. 24, pp. 2347–2354).

It is also known that the 4-bromobenzopyran derivative (XVIII) can be produced from a compound of the general formula (XII) in six steps (JPA Hei 5-294954). According to JPA Hei 5-294954, an acetophenone derivative represented by the general formula (XII) (where $Z^5$ and $Z^6$ which may be the same or different represent a hydrogen atom, a lower alkyl group, a lower haloalkyl group, a halogen atom, a lower haloalkoxy group, an amino group, an acylamino group, a nitro group, a cyano group, an alkoxycarbonyl group, an optionally substituted lower alkylsulfonyl group or an arylsulfonyl group or, when taken together, represent a substituent =N—O—N=) is condensed with an acetone derivative represented by the general formula (XIII) (where $Z^7$ and $Z^8$ which may be the same or different represent a hydrogen atom, a lower alkyl group or a substituted lower alkyl group or, when taken together, represent a polymethylene group or a substituent forming a heterocycle) in the presence of a base such as pyrrolidine to give a benzopyran derivative represented by the general formula (XIV) (where $Z^5, Z^6, Z^7$ and $Z^8$ have the same meanings as defined above). The benzopyran derivative (XIV) is reduced with a suitable reducing agent such as sodium borohydride to give a benzopyran derivative represented by the general formula (XV) (where $Z^5, Z^6, Z^7$ and $Z^8$ have the same meanings as defined above). The benzopyran derivative (XV) is dehydrated with a suitable dehydrating agent such as p-toluenesulfonic acid to give a benzopyran derivative represented by the general formula (XVI) (where $Z^5, Z^6, Z^7$ and $Z^8$ have the same meanings as defined above). The benzopyran derivative (XVI) is brominated with a suitable brominating agent such as bromine to give a 3,4-dibromobenzopyran derivative represented by the general formula (XVII) (where $Z^5, Z^6, Z^7$ and $Z^8$ have the same meanings as defined above). The 3,4-dibromobenzopyran derivative (XVII) is treated with a suitable base such as sodium hydroxide to give a 4-bromobenzopyran derivative represented by the general formula (XVIII) (where $Z^5, Z^6, Z^7$ and $Z^8$ have the same meanings as defined above).

Other processes for producing the benzopyran derivative (XVI) as an intermediate for the general formula (XXVII) have been reported elsewhere (Tetrahedron Letters, 1993, 34, 1815–1818; The 20th Symposium on Progress in Organic Reactions and Syntheses, Shizuoka (1994)).

According to Tetrahedron Letters, 1993, 34, 1815–1818, a compound (IIf) and trimethylsilyl acetylene are subjected to cross-coupling reaction in the presence of copper(I) iodide and tetrakis(triphenylphosphine)palladium and the resulting trimethylsilyl acetylene compound is treated with potassium carbonate in methanol to give a compound represented by the formula (XIX) set forth below. This compound is reacted with hexafluoroacetone using n-butyllithium to give a compound represented by the formula (XX). This compound is reduced with a palladium-barium sulfate catalyst under a hydrogen atmosphere to give a compound represented by the formula (XXI). This compound is reacted with sodium hydride to give a benzopyran derivative represented by the formula (XXII).

According to the 20th Symposium on Progress in Organic Reactions and Syntheses, Shizuoka (1994), 4-fluoronitrobenzene and acetylene represented by the general formula (XXIII) (where $Z^9$ represents a methyl group or a fluoromethyl group) are reacted in the presence of sodium hydride to give a compound represented by the general formula (XXIV) (where $Z^9$ has the same meaning as defined above). This compound is heated in dichlorobenzene to give a benzopyran derivative represented by the general formula (XXV) (where $Z^9$ has the same meaning as defined above).

In the production method of the invention, phenylpropargyl ethers are one of the important intermediates for synthesis and can be produced by known methods such as those described in Synthetic Communications, 19, 1255–1259 (1989) and U.S. Pat. No. 5,463,059.

According to Synthetic Communications, 19, 1255 (1989), a phenol represented by the general formula (H) and a substituted propargyl alcohol represented by the general formula (J) are condensed in benzene in the presence of diethyl azodicarboxylate and triphenylphosphine to give a compound represented by the general formula (K).

According to U.S. Pat. No. 5,463,059, a compound represented by the general formula (L) and a substituted propargyl alcohol represented by the general formula (M) (where L represents a leaving group such as a halogen atom, a trifluoroacetoxy group or an alkoxycarbonyloxy group) are reacted in acetonitrile in the presence of an organic base and a catalytic amount of a copper salt to give a compound represented by the general formula (N).

Other prior art techniques known in the field contemplated by the invention are processes for synthesizing 4-substituted benzopyran derivatives via 4-bromobenzopyran derivatives (XVIII) (JPA Hei 7-17965, JPA Hei 7-188210 and Tetrahedron Letters, 1995, 36, 87–90). According to JPA Hei 7-17965 and JPA Hei 7-188210, the general formula (P) (where $Z^a$ and $Z^b$ which may be the same or different represent a hydrogen atom, a lower alkyl group, a lower haloalkyl group, a halogen atom, a lower haloalkoxy group, an amino group, an acylamino group, a nitro group, a cyano group, an ester group, a lower alkylsulfonyl group or a lower arylsulfonyl group or, when taken together, represent a substituent =N—O—N=; $Z^c$ and $Z^d$ which may be the same or different represent a hydrogen atom, a lower alkyl group or a substituted alkyl group or, when taken together, represent a polymethylene group or a substituent forming a heterocycle) is reacted with carbon monoxide and amine in the presence of a palladium catalyst to give an amide form represented by the general formula (Q).

However, the reaction for the synthesis of benzopyran having a bromine-containing group introduced at 4-position involves so many steps that cumbersome treatment procedures are required. In particular, the intermediate benzopyran derivative (XIV) is a labile compound, so large amounts of decomposition products occur as by-products during the synthesis of the benzopyran and very cumbersome post-treatment procedures are involved. As a further problem, due to their labile nature, derivatives having acid- or base-sensitive functional groups such as a perfluoroalkyl group in $Z^7$ and $Z^8$ cannot be synthesized without suitable protective groups. Because of these problems, extreme difficulties have often been encountered in the synthesis of the benzopyran. In order to produce the compound (XXIV), the presence of a nitro group in para-position is essential, so the process involving the formation of this compound as an intermediate does not have extensive applicability.

The method of synthesis of 4-halobenzopyrans that is described in JPA Hei 5-294954 has a long synthesis pathway and is not satisfactory in terms of yield. It has therefore been desired to develop a synthesis pathway that is short and yet has a broad range of applications. The idea of condensing phenol and alcohol using the Mitsunobu Reaction as described in Synthetic Communications, 19, 1255–1259 (1989) turned out to be very inefficient (low yield) when it was applied to the synthesis of the compounds of the present invention. U.S. Pat. No. 5,463,059 gives no example of condensation between a dihalomethyl-substituted propargyl alcohol and phenol and it involves other difficulties such as the use of expensive anhydrous trifluoroacetic acid and 1,8-diazabicyclo(5.4.0)-7-undecene.

Under these circumstances, it has been required to develop a process for producing 4-substituted benzopyran derivatives that involves a smaller number of steps, that is economical and which yet allows for easy post-treatment and purification procedures.

As a result of their intensive studies, the present inventors found very useful processes for producing 4-substituted benzopyran derivatives that were shorter, safe, high in yield and which yet allowed for easy treatment and purification procedures.

DISCLOSURE OF THE INVENTION

The present invention provides the following various production processes.

1. A process for producing 4-substituted benzopyran derivatives represented by the general formula (G-VI) [where $R^1$ and $R^2$ which may be the same or different represent a hydrogen atom, an optionally substituted lower alkyl group, an optionally substituted lower alkoxy group, an optionally substituted lower alkoxycarbonyl group, an optionally substituted lower alkylsulfonyl group, an optionally substituted arylsulfonyl group, a halogen atom, a nitro group, a cyano group or $NY_aY_b$ (where $Y_a$ and $Y_b$ which may be the same or different each represent a hydrogen atom, an optionally substituted lower alkyl group, an optionally substituted lower alkoxycarbonyl group, an acyl group, an optionally substituted lower alkylsulfonyl group or an optionally substituted arylsulfonyl group or, when taken together with the nitrogen atom to which they are bound, may form a 3- to 8-membered ring) or, when taken together, represent a substituent =N—O—N=; $R^3$ and $R^4$ which may be the same or different represent a hydrogen atom or an optionally substituted lower alkyl group or, when taken together with the carbon atom to which they are bound, represent a polymethylene group or a substituent forming a heterocycle, provided that $R^3$ and $R^4$ are not both a hydrogen atom; $R^5$ and $R^6$ which may be the same or different represent a hydrogen atom or an optionally substituted lower alkyl group] by any one of the schemes (1), (2), (3), (4), (5) and (6) containing a plurality of steps as indicated below, namely, (1): (1-1)→(1-2)→(1-3)→(1-4)→(1-5);
(2): (2-1)→(2-2)→(2-3)→(2-4)→(2-5)→(1-5);
(3): (3-1)→(3-2);
(4): (4-1)→(4-2);
(5): (a-1)→(a-2)→(b-1)→(b-2)→(1-5); and
(6): (a-1)→(a-2)→(d-1)→(d-2)→(d-3);

(1-1) the step of reacting a compound of the general formula (II) (where X and Y which may be the same or different represent a leaving group such as a halogen atom, an optionally substituted lower alkylsulfonyloxy group or an arylsulfonyloxy group; $R^1$ and $R^2$ have the same meanings as defined above) with an olefin of the general formula (III) (where $R^3$ and $R^4$ have the same meanings as defined above) to give a compound of the general formula (IV) (where Y, $R^1$, $R^2$, $R^3$ and $R^4$ have the same meanings as defined above);

(1-2) the step of reacting the resulting compound of the general formula (IV) with a halogenating agent to give a compound of the general formula (V) (where Y, $R^1$, $R^2$, $R^3$, $R^4$ and Hal have the same meanings as defined above);

(1-3) the step of reacting the resulting compound of the general formula (V) with a base to give a compound of the general formula (VI) (where Y, $R^1$, $R^2$, $R^3$, $R^4$ and Hal have the same meanings as defined above);

(1-4) the step of reacting the resulting compound-of the general formula (VI) with a base to give a 4-halobenzopyran of the general formula (I) (where Y, $R^1$, $R^2$, $R^3$, $R^4$ and Hal have the same meanings as defined above);

(1-5) the step of reacting the compound of the general formula (I) with carbon monoxide and a compound of the general formula (G-III)

$R^5R^6NH$            (G-III)

(where $R^5$ and $R^6$ which may be the same or different represent a hydrogen atom or an optionally substituted lower alkyl group) in the presence of a metal to give a 4-substituted benzopyran derivative of the general formula (G-VI) set forth above;

(2-1) the step of reacting a compound of the general formula (III) with acetylene of the general formula (VII) (where $R^3$ and $R^4$ have the same meanings as defined above) to give a compound of the general formula (VIII) (where Y, $R^1$, $R^2$, $R^3$ and $R^4$ have the same meanings as defined above);

(2-2) the step of reacting the resulting compound of the general formula (VIII) with a reducing agent to give a compound of the general formula (IX) (where Y, $R^1$, $R^2_1$, $R^3$ and $R^4$ have the same meanings as defined above);

(2-3) the step of reacting the resulting compound of the general formula (IX) with a base to give a benzopyran derivative of the general formula (X) (where $R^1$, $R^2$, $R^3$ and $R^4$ have the same meanings as defined above);

(2-4) the step of reacting the resulting compound of the general formula (X) with a halogenating agent to give a 3,4-dihalobenzopyran derivative of the general formula (XI) (where $R^1$, $R^2$, $R^3$, $R^4$ and Hal have the same meanings as defined above);

(2-5) the step of reacting the resulting compound of the general formula (XI) with a base to give a 4-halobenzopyran derivative of the general formula (I) (where $R^1$, $R^2$, $R^3$, $R^4$ and Hal have the same meanings as defined above);

(3-1) the step of reacting a compound of the general formula (G-I) (where $R^1$, $R^2$, $R^3$ and $R^4$ have the same meanings as defined above) with carbon dioxide in the presence of a base to give a compound of the general formula (G-II) (where $R^1$, $R^2$, $R^3$ and $R^4$ have the same meanings as defined above) or a salt thereof;

(3-2) the step of reacting the resulting compound of the general formula (G-II) or salt thereof with a compound of the genera formula (G-III)

$$R^5R^6NH \qquad (G\text{-}III)$$

(where $R^5$ and $R^6$ which may be the same or different represent a hydrogen atom or an optionally substituted lower alkyl group) to give a 4-substituted benzopyran derivative of the general formula (G-VI) set forth above;

(4-1) the step of reacting a compound of the general formula (G-I) (where $R^1$, $R^2$, $R^3$ and $R^4$ have the same meanings as defined above) with a compound of the general formula (G-IVa) (where $R^5$ and $R^6$ which may be the same or different represent a hydrogen atom or an optionally substituted lower alkyl group) or a compound of the general formula (G-IVb)

$$R^{6a}NCO \qquad (G\text{-}IVb)$$

(where $R^{6a}$ represents an optionally substituted lower alkyl group) in the presence of a base to give a compound of the general formula (G-V) (where $R^1$, $R^2$, $R^3$, $R^4$, $R^5$ and $R^6$ have the same meanings as defined above);

(4-2) the step of subjecting the resulting compound of the general formula (G-V) to thermal cyclization reaction to give a 4-substituted benzoyran derivative of the general formula (G-VI) set forth above;

(a-1) the step of reacting an alcohol of the general formula (C-I) (where $R^3$ and $R^4$ have the same meanings as defined above) with a compound of the general formula (C-II) or (C-III)

$$R^7SO_2Cl \qquad (C\text{-}II)$$

$$(R^7SO_2)_2O \qquad (C\text{-}II)$$

(where $R^7$ represents an optionally substituted alkyl group or an optionally substituted aryl group) in the presence of a base to give a compound of the general formula (C-IV) (where $R^7$, $R^3$ and $R^4$ have the same meanings as defined above);

(a-2) the step of reacting the compound of the general formula (C-IV) with a compound of the general formula (C-V) (where $R^1$ and $R^2$ have the same meanings as defined above) in the presence of a base and a monovalent or divalent copper salt to give a compound of the general formula (C-VI) (where $R^1$, $R^2$, $R^3$ and $R^4$ have the same meanings as defined above);

(b-1) the step of subjecting the compound of the general formula (C-VI) which is the end product of step (a-2) to halogenation reaction to give a compound of the general formula (D-II) (where $R^1$, $R^2$, $R^3$ and $R^4$ have the same meanings as defined above and Hal represents a halogen atom);

(b-2) the step of subjecting the compound of the general formula (D-II) to thermal cyclization reaction to give a 4-halobenzopyran derivative of the general formula (I) (where $R^1$, $R^2$, $R^3$, $R^4$ and Hal have the same meanings as defined above);

(d-1) the step of reacting the compound of the general formula (C-VI), which is the end product of step (a-2), with a compound of the general formula (H-II)

$$O=C(OR^8)_2 \qquad (H\text{-}II)$$

or a compound of the general formula (H-III)

$$ClC=O(OR^8) \qquad (H\text{-}III)$$

(where $R^1$ represents an optionally substituted lower alkyl group) to give a compound of the general formula (H-IV) (where $R^1$, $R^2$, $R^3$, $R^4$ and $R^8$ have the same meanings as defined above);

(d-2) the step of subjecting the compound of the general formula (H-IV) to thermal cyclization reaction to give a compound of the general formula (H-V) (where $R^1$, $R^2$, $R^3$, $R^4$ and $R^8$ have the same meanings as defined above);

(d-3) the step of hydrolyzing the resulting compound of the general formula (H-V) and then subjecting the hydrolyzate to dehydrative condensation with a compound of the general formula (G-III)

$$R^5R^6NH \qquad (G\text{-}III)$$

(where $R^5$ and $R^6$ which may be the same or different represent a hydrogen atom or an optionally substituted lower alkyl group) to give a 4-substituted benzopyran derivative of the general formula (G-VI) set forth above.

2. A process for producing 4-substituted benzopyran derivatives represented by the general formula (G-VIa) (where $R^{1a}$ represents a lower perfluoroalkyl group, a nitro group or a cyano group; $R^{3a}$ and $R^{4a}$ which may be the same or different represent a hydrogen atom, an optionally substituted lower alkyl group or, when taken together with the carbon atom to which they are bound, represent a polymethylene group or a substituent forming a heterocycle, provided that $R^{3a}$ and $R^{4a}$ are not both a hydrogen atom; $R^5$ and $R^6$ which may be the same or different represent a hydrogen atom or an optionally substituted lower alkyl group) by any one of the schemes (1a) and (2a) containing a plurality of steps as indicated below, namely, (1a) (1a-1)→(1a-2)→(1a-3)→(1a-4)→(1a-5); and (2a) (2a-1)→(2a-2)→(2a-3)→(2a-4)→(2a-5)→(1a-5);

(1a-1) the step of reacting a compound of the general formula (IIa) (where X and Y which may be the same or different represent a leaving group such as a halogen atom, an optionally substituted lower alkylsulfonyloxy group or an arylsulfonyloxy group; $R^{1a}$ has the same meaning as defined above) with an olefin of the general formula (IIIa) (where $R^{3a}$ and $R^{4a}$ have the same meanings as defined above) to give a compound of the general formula (IVa) (where Y, $R^{1a}$, $R^{3a}$ and $R^{4a}$ have the same meanings as defined above);

(1a-2) the step of reacting the resulting compound of the general formula (IVa) with a halogenating agent to give a compound of the general formula (Va) (where Y, $R^{1a}$, $R^{3a}$ and $R^{4a}$ have the same meanings as defined above, and Hal represents a halogen atom);

(1a-3) the step of reacting the resulting compound of the general formula (Va) with a base to give a compound of the general formula (VIa) (where Y, $R^{1a}$, $R^{3a}$, $R^{4a}$ and Hal have the same meanings as defined above);

(1a-4) the step of reacting the resulting compound of the general formula (VIa) with a base to give a compound of the general formula (Ia) (where $R^{1a}$, $R^{3a}$, $R^{4a}$ and Hal have the same meanings as defined above);

(1a-5) the step of reacting the resulting compound of the general formula (Ia) with carbon monoxide and a compound of the general formula (G-III)

$$R^5R^6NH \qquad \text{(G-III)}$$

(where $R^5$ and $R^6$ which may be the same or different represent a hydrogen atom or an optionally substituted lower alkyl group) in the presence of a metal to give a 4-substituted benzopyran derivative of the general formula (G-VIa) set forth above (where $R^{1a}$, $R^{3a}$, $R^{4a}$, $R^5$ and $R^6$ have the same meanings as defined above);

(2a-1) the step of reacting a compound of the general formula (IIa) with acetylene of the general formula (VIIa) (where $R^{3a}$ and $R^{4a}$ have the same meanings as defined above) to give a compound of the general formula (VIIIa) (where Y, $R^{1a}$, $R^{3a}$ and $R^{4a}$ have the same meanings as defined above);

(2a-2) the step of treating the resulting compound of the general formula (VIIIa) with a reducing agent to give a compound of the general formula (IXa) (where Y, $R^{1a}$, $R^{3a}$ and $R^{4a}$ have the same meanings as defined above);

(2a-3) the step of reacting the resulting compound of the general formula (IXa) with a base to give a benzopyran derivative of the general formula (Xa) (where $R^{1a}$, $R^{3a}$ and $R^{4a}$ have the same meanings as defined above);

(2a-4) the step of reacting the resulting compound of the general formula (Xa) with a halogenating agent to give a 3,4-dihalobenzopyran derivative of the general formula (XIa) (where $R^{1a}$, $R^{3a}$ and $R^{4a}$ have the same meanings as defined above and Hal represents a halogen atom);

(2a-5) the step of treating the resulting compound of the general formula (XIa) with a base to give a 4-halobenzopyran derivative of the general formula (Ia) set forth above.

3. A process for producing 4-substituted benzopyran derivatives represented by the general formula (G-VIb) (where $R^{1b}$ represents a lower perfluoroalkyl group; $R^{3b}$ and $R^{4b}$ which may be the same or different represent a hydrogen atom, an optionally substituted lower alkyl group or, when taken together with the carbon atom to which they are bound, represent a polymethylene group, provided that $R^{3b}$ and $R^{4b}$ are not both a hydrogen atom; $R^5$ and $R^6$ which may be the same or different represent a hydrogen atom or an optionally substituted lower alkyl group) by any one of the schemes (1b) and (2b) containing a plurality of steps as indicated below, namely, (1b) (1b-1)→(1b-2)→(1b-3)→(1b-4)→(1b-5); and
(2b)→(2b-1)→(2b-2)→(2b-3)→(2ba-4)→(2b-5)→(1b-5);

(1b-1) the step of reacting a compound of the general formula (IIb) (where X and Y which may be the same or different represent a leaving group such as a halogen atom, an optionally substituted lower alkylsulfonyloxy group or an arylsulfonyloxy group; $R^{1b}$ has the same meaning as defined above) with an olefin of the general formula (IIIb) (where $R^{3b}$ and $R^{4b}$ have the same meanings as defined above) to give a compound of the general formula (IVb) (where Y, $R^{1b}$, $R^{3b}$ and $R^{4b}$ have the same meanings as defined above); (1b-2) the step of reacting the resulting compound of the general formula (IVb) with a halogenating agent to give a compound of the general formula (Vb) (where Y, $R^{1b}$, $R^{3b}$ and $R^{4b}$ have the same meanings as defined above, and Hal represents a halogen atom);

(1b-3) the step of reacting the resulting compound of the general formula (Vb) with a base to give a compound of the general formula (VIb) (where Y, $R^{1b}$, $R^{3b}$, $R^{4b}$ and Hal have the same meanings as defined above);

(1b-4) the step of reacting the resulting compound of the general formula (VIb) with a base to give a compound of the general formula (Ib) (where $R^{1b}$, $R^{3b}$, $R^{4b}$ and Hal have the same meanings as defined above);

(Ib-5) the step of reacting the resulting compound of the general formula (Ib) with carbon monoxide and a compound of the general formula (G-III)

$$R^5R^6NH \qquad \text{(G-III)}$$

(where $R^5$ and $R^6$ which may be the same or different represent a hydrogen atom or an optionally substituted lower alkyl group) in the presence of a metal to give a 4-substituted benzopyran derivative of the general formula (G-VIb) set forth above (where $R^{1b}$, $R^{3b}$, $R^{4b}$, $R^5$ and $R^6$ have the same meanings as defined above);

(2b-1) the step of reacting a compound of the general formula (IIb) with acetylene of the general formula (VIIb) (where $R^{3b}$ and $R^{4b}$ have the same meanings as defined above) to give a compound of the general formula (VIIIb) (where Y, $R^{1b}$, $R^{3b}$ and $R^{4b}$ have the same meanings as defined above);

(2b-2) the step of treating the resulting compound of the general formula (VIIIb) with a reducing agent to give a compound of the general formula (IXb) (where Y, $R^{1b}$, $R^{3b}$ and $R^{4b}$ have the same meanings as defined above);

(2b-3) the step of reacting the resulting compound of the general formula (IXb) with a base to give a benzopyran derivative of the general formula (Xb) (where $R^{1b}$, $R^{3b}$ and $R^{4b}$ have the same meanings as defined above);

(2b-4) the step of reacting the resulting compound of the general formula (Xb) with a halogenating agent to give a 3,4-dihalobenzopyran derivative of the general formula (XIb) (where $R^{1b}$, $R^{3b}$, $R^{4b}$ and Hal have the same meanings as defined above);

(2b-5) the step of treating the resulting compound of the general formula (XIb) with a base to give a 4-halobenzopyran derivative of the general formula (Ib) set forth above.

4. A process for producing 4-substituted benzopyran derivatives represented by the general formula (G-VIc) (where $R^{1b}$ represents a lower perfluoroalkyl group; $R^{3c}$ and $R^{4c}$ which are the same represent a lower alkyl group or a lower fluoroalkyl group; $R^{5c}$ represents a hydrogen atom and $R^6$ represents an optionally substituted lower alkyl group) by any one of the schemes (1c) and (2c) containing a plurality of steps as indicated below, namely, (1c) (1c-1)→(1c-2)→(1c-3)→(1c-4)→(1c-5); and (2c) (2c-1)→(2c-2)→(2c-3)→(2c-4)→(2c-5)→(1c-5);

(1c-1) the step of reacting a compound of the general formula (IIb) (where X and Y which may be the same or different represent a leaving group such as a halogen atom, an optionally substituted lower alkylsulfonyloxy group or an arylsulfonyloxy group; $R^{1b}$ has the same meaning as defined above) with an olefin of the general formula (IIIc) (where $R^{3c}$ and $R^{4c}$ have the same meanings as defined above) to give a compound of the general formula (IVc) (where Y, $R^{1b}$, $R^{3c}$ and $R^{4c}$ have the same meanings as defined above);

(1c-2) the step of reacting the resulting compound of the general formula (IVc) with a halogenating agent to give a compound of the general formula (Vc) (where Y, $R^{1b}$, $R^{3c}$ and $R^{4c}$ have the same meanings as defined above, and Hal represents a halogen atom);

(1c-3) the step of reacting the resulting compound of the general formula (Vc) with a base to give a compound of the general formula (VIc) (where Y, $R^{1b}$, $R^{3c}$ and $R^{4c}$ have the same meanings as defined above, and Hal represents a halogen atom);

(1c-4) the step of reacting the resulting compound of the general formula (VIc) with a base to give a compound of the general formula (Ic) (where $R^{1b}$, $R^{3c}$, $R^{4c}$ and Hal have the same meanings as defined above);

(Ic-5) the step of reacting the resulting compound of the general formula (Ic) with carbon monoxide and a compound of the general formula (G-IIIc)

 (G-IIIc)

(where $R^{5c}$ represents a hydrogen atom and $R^{6a}$ represents an optionally substituted lower alkyl group) in the presence of a metal to give a 4-substituted benzopyran derivative of the general formula (G-VIc) set forth above;

(2c-1) the step of reacting a compound of the general formula (IIb) with acetylene of the general formula (VIIc) (where $R^{3c}$ and $R^{4c}$ have the same meanings as defined above) to give a compound of the general formula (VIIIc) (where Y, $R^{1b}$, $R^{3c}$ and $R^{4c}$ have the same meanings as defined above);

(2c-2) the step of treating the resulting compound of the general formula (VIIIc) with a reducing agent to give a compound of the general formula (IXc) (where Y, $R^{1b}$, $R^{3c}$ and $R^{4c}$ have the same meanings as defined above);

(2c-3) the step of reacting the resulting compound of the general formula (IXc) with a base to give a benzopyran derivative of the general formula (Xc) (where $R^{1b}$, $R^{3c}$ and $R^{4c}$ have the same meanings as defined above);

(2c-4) the step of reacting the resulting compound of the general formula (Xc) with a halogenating agent to give a 3,4-dihalobenzopyran derivative of the general formula (XIc) (where $R^{1b}$, $R^{3c}$, $R^{4c}$ and Hal have the same meanings as defined above);

(2c-5) the step of treating the resulting compound of the general formula (XIc) with a base to give a 4-halobenzopyran derivative of the general formula (Ic) set forth above.

5. A process for producing 4-substituted benzopyran derivatives represented by the general formula (G-VId) (where $R^{1b}$ represents a lower perfluoroalkyl group; $R^{5c}$ represents a hydrogen atom; and $R^{6b}$ represents a lower alkyl group which may optionally have a cyano group) by any one of the schemes (1d) and (2d) containing a plurality of steps as indicated below, namely, (1d) (1d-1)→(1d-2)→(1d-3)→(1d-4)→(1d-5); and (2d) (2d-1)→(2d-2)→(2d-3)→(2d-4)→(2d-5)→(1d-5);

(1d-1) the step of reacting a compound of the general formula (IId) (where X and Y which may be the same or different represent a leaving group such as a halogen atom, an optionally substituted lower alkylsulfonyloxy group or an arylsulfonyloxy group; $R^{1b}$ has the same meaning as defined above) with an olefin of the general formula (IIId) set forth below to give a compound of the general formula (IVd) (where Y and $R^{1b}$ have the same meanings as defined above);

(1d-2) the step of reacting the resulting compound of the general formula (IVd) with a halogenating agent to give a compound of the general formula (Vd) (where Y and $R^{1b}$ have the same meanings as defined above, and Hal represents a halogen atom);

(1d-3) the step of reacting the resulting compound of the general formula (Vd) with a base to give a compound of the general formula (VId) (where Y, $R^{1b}$ and Hal have the same meanings as defined above);

(1d-4) the step of reacting the resulting compound of the general formula (VId) with a base to give a 4-halobenzopyran derivative of the general formula (Id) (where $R^{1b}$ and Hal have the same meanings as defined above);

(Id-5) the step of reacting the resulting compound of the general formula (Id) with carbon monoxide and a compound of the general formula (G-IIId)

 (G-IIId)

(where $R^{5c}$ represents a hydrogen atom and $R^{6b}$ represents a lower alkyl group which may optionally have a cyano group) in the presence of a metal to give a 4-substituted benzopyran derivative of the general formula (G-VId) set forth above;

(2d-1) the step of reacting a compound of the general formula (IId) with acetylene of the general formula (VIId) to give a compound of the general formula (VIIId) (where Y and $R^{1b}$ have the same meanings as defined above);

(2d-2) the step of treating the resulting compound of the general formula (VIIId) with a reducing agent to give a compound of the general formula (IXd) (where Y and $R^{1b}$ have the same meanings as defined above);

(2d-3) the step of reacting the resulting compound of the general formula (IXd) with a base to give a benzopyran derivative of the general formula (Xd) (where $R^{1b}$ has the same meaning as defined above);

(2d-4) the step of reacting the resulting compound of the general formula (Xd) with a halogenating agent to give a 3,4-dihalobenzopyran derivative of the general formula (XId) (where $R^{1b}$ and Hal have the same meanings as defined above);

(2d-5) the step of treating the resulting compound of the general formula (XId) with a base to give a 4-halobenzopyran derivative of the general formula (Id) (where $R^{1b}$ and Hal have the same meanings as defined above).

6. A process for producing 4-substituted benzopyran derivatives represented by the general formula (G-VIe) (where $R^{1e}$ represents a trifluoromethyl group or a pentafluoroethyl group; $R^{5c}$ represents a hydrogen atom; $R^{6d}$ represents a cyanoethyl group) by any one of the schemes (1e) and (2e) containing a plurality of steps as indicated below, namely, (1e) (1e-1)→(1e-2)→(1e-3)→(1e-4)→(1e-5); and (2e) (2e-1)→(2e-2)→(2e-3)→(2e-4)→(2e-5)→(1e-5);

(1e-1) the step of reacting a compound of the general formula (IIe) (where $R^{1e}$ has the same meaning as defined above) with an olefin of the general formula (IIId) set forth below to give a compound of the general formula (IVe) (where $R^{1e}$ has the same meaning as defined above);

(1e-2) the step of reacting the resulting compound of the general formula (IVe) with a halogenating agent to give a compound of the general formula (Ve) (where $R^{1e}$ has the same meaning as defined above; Hal represents a halogen atom);

(1e-3) the step of reacting the resulting compound of the general formula (Ve) with a base to give a compound of the general formula (VIe) (where $R^{1e}$ and Hal have the same meanings as defined above);

(1e-4) the step of reacting the resulting compound of the general formula (VIe) with a base to give a 4-halobenzopyran derivative of the general formula (Ie) (where $R^{1e}$ and Hal have the same meanings as defined above);

(Ie-5) the step of reacting the resulting compound of the general formula (Ie) with carbon monoxide and a compound of the general formula (G-IIIe)

$$R^{5c}R^{6d}NH \qquad \text{(G-IIIe)}$$

(where $R^{5c}$ represents a hydrogen atom and $R^{6d}$ represents a cyanoethyl group) in the presence of a metal to give a 4-substituted benzopyran derivative of the general formula (G-VIe) set forth above;

(2e-1) the step of reacting a compound of the general formula (IIe2) (where $R^{1e}$ has the same meaning as defined above) with acetylene of the general formula (VIId) set forth below to give a compound of the general formula (VIIIe) (where $R^{1e}$ has the same meaning as defined above);

(2e-2) the step of treating the resulting compound of the general formula (VIIIe) with a reducing agent to give a compound of the general formula (IXe) (where $R^{1e}$ has the same meaning as defined above);

(2e-3) the step of reacting the resulting compound of the general formula (IXe) with a base to give a benzopyran derivative of the general formula (Xd) (where $R^{1d}$ has the same meaning as defined above);

(2e-4) the step of reacting the resulting compound of the general formula (Xd) with a halogenating agent to give a 3,4-dihalobenzopyran derivative of the general formula (XIe) (where $R^{1e}$ and Hal have the same meanings as defined above);

(2e-5) the step of treating the resulting compound of the general formula (XIe) with a base to give a 4-halobenzopyran derivative of the general formula (Ie) set forth above.

7. A process according to scheme (3) or (4) in Process 1 for producing 4-substituted benzopyran derivatives represented by the general formula (G-VIg) [where $R^{1g}$ and $R^{2g}$ which may be the same or different represent a hydrogen atom, an optionally substituted lower alkyl group, an optionally substituted lower alkoxy group, an optionally substituted lower alkoxycarbonyl group, an optionally substituted lower alkylsulfonyl group, an optionally substituted arylsulfonyl group, a halogen atom, a nitro group, a cyano group or $NY_aY_b$ (where $Y_a$ and $Y_b$ which may be the same or different each represent a hydrogen atom, an optionally substituted lower alkyl group, an optionally substituted lower alkoxycarbonyl group, an acyl group, an optionally substituted lower alkylsulfonyl group or an optionally substituted arylsulfonyl group or, when taken together with the nitrogen atom to which they are bound, may form a 3- to 8-membered ring); $R^{3g}$ and $R^{4g}$ which may be the same or different represent a hydrogen atom or an optionally substituted α-haloalkyl group, provided that they are not both a hydrogen atom; $R^5$ and $R^6$ which may be the same or different represent a hydrogen atom or an optionally substituted lower alkyl group] by the steps of:

reacting an alcohol of the general formula (C-Ig) (where $R^{3g}$ and $R^{4g}$ have the same meanings as defined above) with a compound of the general formula (C-II) or (C-III)

$$R^7SO_2Cl \qquad \text{(C-II)}$$

$$(R^7SO_2)_2O \qquad \text{(C-III)}$$

(where $R^7$ represents an optionally substituted alkyl group or an optionally substituted aryl group) in the presence of a base to give a compound of the general formula (C-IVg) (where $R^7$, $R^{3g}$ and $R^{4g}$ have the same meanings as defined above);

reacting the compound of the general formula (C-IVg) with a compound of the general formula (C-Vg) (where $R^{1g}$ and $R^{2g}$ have the same meanings as defined above) in the presence of a base and a monovalent or divalent copper salt to give a compound of the general formula, (G-Ig) (where $R^{1g}$, $R^{2g}$, $R^{3g}$ and $R^{4g}$ have the same meanings as defined above);

reacting the compound of the general formula (G-Ig) with carbon dioxide in the presence of a base to give a compound of the general formula (G-IIg) (where $R^{1g}$, $R^{2g}$, $R^{3g}$ and $R^{4g}$ have the same meanings as defined above) or a salt thereof;

reacting the compound of the general formula (G-IIg) or salt thereof with a compound of the general formula (G-III)

$$R^5R^6NH \qquad \text{(G-III)}$$

(where $R^5$ and $R^6$ which may be the same or different represent a hydrogen atom or an optionally substituted lower alkyl group) to give a compound of the general formula (G-Vg) (where $R^{1g}$, $R^{2g}$, $R^{3g}$, $R^{4g}$, $R^5$ and $R^6$ have the same meanings as defined above); or alternatively reacting the compound of the general formula (G-Ig) (where $R^{1g}$, $R^{2g}$, $R^{3g}$ and $R^{4g}$ have the same meanings as defined above) with a compound of the general formula (G-IVa) (where $R^5$ and $R^6$ which may be the same or different represent a hydrogen atom or an optionally substituted lower alkyl group) or a compound of the general formula (G-IVb)

$$R^{6a}NCO \qquad \text{(G-IVb)}$$

(where $R^{6a}$ represents an optionally substituted lower alkyl group) in the presence of a base to give a compound of the general formula (G-Vg) (where $R^{1g}$, $R^2$, $R^{3g}$, $R^{4g}$, $R^5$ and $R^6$ have the same meanings as defined above); and subjecting the compound of the general formula (G-Vg) to thermal cyclization reaction.

8. A process according to scheme (3) or (4) in Process 1 or a process according to Process 7 for producing 4-substituted benzopyran derivatives represented by the general formula (G-VIh) set forth below, wherein $R^1$ and $R^2$ in the general formula (G-VI) which may be the same or different represent a hydrogen atom, an optionally substituted lower alkyl group, an optionally substituted lower alkoxy group, an optionally substituted lower alkoxycarbonyl group, an optionally substituted lower alkylsulfonyl group, an optionally substituted arylsulfonyl group, a halogen atom, a nitro group, a cyano group or $NY_aY_b$ (where $Y_a$ and $Y_b$ which may be the same or different each represent a hydrogen atom, an optionally substituted lower alkyl group, an optionally substituted lower alkoxycarbonyl group, an acyl group, an optionally substituted lower alkylsulfonyl group or an optionally substituted arylsulfonyl group or, when taken together, may form a 3- to 8-membered ring); $R^3$ and $R^4$ each represent a fluoromethyl group; and $R^5$ and $R^6$ which may be the same or different represent a hydrogen atom or an optionally substituted lower alkyl group.

9. A process according to scheme (3) or (4) in Process 1 or a process according to Process 7 for producing 4-substituted benzopyran derivatives represented by the general formula (G-VIi) set forth below, wherein $R^1$ in the general formula (G-VI) represents a 6-trifluoromethyl group or a 6-pentafluoroethyl group; $R^2$ represents a hydrogen atom; $R^3$ and $R^4$ each represent a fluoromethyl group; and $R^5$ and $R^6$ which may be the same or different represent a hydrogen atom or an optionally substituted lower alkyl group.

10. A process according to scheme (3) or (4) in Process 1 or a process according to Process 7 for producing 4-substituted benzopyran derivatives represented by the general formula (G-VIj) set forth below, wherein $R^1$ in the general formula (G-VI) represents a 6-trifluoromethyl group or a 6-pentafluoroethyl group; $R^2$ represents a hydrogen atom; $R^3$ and $R^4$ each represent a fluoromethyl group; and $R^5$ represents a hydrogen atom and $R^6$ represents a 2-cyanoethyl group.

11. A process for producing 4-substituted benzopyran derivatives represented by the general formula (G-VIg) [where $R^{1g}$ and $R^{2g}$ which may be the same or different represent a hydrogen atom, an optionally substituted lower alkyl group, an optionally substituted lower alkoxy group, an optionally substituted lower alkoxycarbonyl group, an optionally substituted lower alkylsulfonyl group, an optionally substituted arylsulfonyl group, a halogen atom, a nitro group, a cyano group or $NY_aY_b$ (where $Y_a$ and $Y_b$ which may be the same or different each represent a hydrogen atom, an optionally substituted lower alkyl group, an optionally substituted lower alkoxycarbonyl group, an acyl group, an optionally substituted lower alkylsulfonyl group or an optionally substituted arylsulfonyl group or, when taken together with the nitrogen atom to which they are bound, may form a 3- to 8-membered ring); $R^{3g}$ and $R^{4g}$ which may be the same or different represent a hydrogen atom or an optionally substituted α-haloalkyl group, provided that they are not both a hydrogen atom; $R^5$ and $R^6$ which may be the same or different represent a hydrogen atom or an optionally substituted lower alkyl group], wherein a compound represented by the general formula (G-VIg) (where $R^{1g}$, $R^{2g}$, $R^{3g}$, $R^{4g}$, $R^5$ and $R^6$ have the same meanings as defined above).

12. A process according to Process 11 for producing 4-substituted benzopyran derivatives represented by the general formula (G-VIl) set forth below, wherein $R^{1g}$ and $R^{2g}$ in the general formula (G-VIg) which may be the same or different represent a hydrogen atom, an optionally substituted lower alkyl group, an optionally substituted lower alkoxy group, an optionally substituted lower alkoxycarbonyl group, an optionally substituted lower alkylsulfonyl group, an optionally substituted arylsulfonyl group, a halogen atom, a nitro group, a cyano group or $NY_aY_b$ (where $Y_a$ and $Y_b$ which may be the same or different each represent a hydrogen atom, an optionally substituted lower alkyl group, an optionally substituted lower alkoxycarbonyl group, an acyl group, an optionally substituted lower alkylsulfonyl group or an optionally substituted arylsulfonyl group or, when taken together with the nitrogen atom to which they are bound, may form a 3- to 8-membered ring); $R^{3g}$ and $R^{4g}$ each represent a fluoromethyl group; $R^5$ and $R^6$ which may be the same or different represent a hydrogen atom or an optionally substituted lower alkyl group.

13. A process according to Process 11 for producing 4-substituted benzopyran derivatives represented by the general formula (G-VIm) set forth below, wherein $R^{1g}$ in the general formula (G-VIg) represents a 6-trifluoromethyl group or a 6-pentafluoroethyl group; $R^{2g}$ represents a hydrogen atom; $R^{3g}$ and $R^{4g}$ each represent a fluoromethyl group; and $R^5$ and $R^6$ which may be the same or different represent a hydrogen atom or an optionally substituted lower alkyl group.

14. A process according to Process 11 for producing 4-substituted benzopyran derivatives represented by the general formula (G-VIn) set forth below, wherein $R^{1g}$ in the general formula (G-VIg) represents a 6-trifluoromethyl group or a 6-pentafluoroethyl group; $R^{2g}$ represents a hydrogen atom; $R^{3g}$ and $R^{4g}$ each represent a fluoromethyl group; and $R^5$ represents a hydrogen atom and $R^6$ represents a 2-cyanoethyl group.

15. A process according to scheme (5) or (6) in Process 1 for producing 4-substituted benzopyran derivatives represented by the general formula (Iz) set forth below [where $R^{1g}$ and $R^{2g}$ which may be the same or different represent a hydrogen atom, an optionally substituted lower alkyl group, a halogen atom, an optionally substituted lower alkoxy group, $NY_aY_b$ (where $Y_a$ and $Y_b$ which may be the same or different each represent a hydrogen atom, an optionally substituted lower alkyl group, an optionally substituted lower alkoxycarbonyl group, an acyl group, an optionally substituted lower alkylsulfonyl group or an optionally substituted arylsulfonyl group or, when taken together with the nitrogen atom to which they are bound, may form a 3- to 8-membered ring), a nitro group, a cyano group, an optionally substituted lower alkoxycarbonyl group, an optionally substituted lower alkylsulfonyl group or an optionally substituted arylsulfonyl group; Hal represents a halogen atom] by the steps of:

reacting an alcohol of the general formula (C-Ia) with a compound of the general formula (C-II) or (C-III)

 (C-II)

 (C-III)

(where $R^7$ represents an optionally substituted lower alkyl group or an optionally substituted aryl group) in the presence of a base to give a compound of the general formula (C-IVa) (where $R^7$ has the same meaning as defined above);

reacting the compound of the general formula (C-IVa) with a compound of the general formula (C-Vg) (where $R^{1g}$ and $R^{2g}$ have the same meanings as defined above) in the presence of a base and a monovalent or divalent copper salt to give a compound of the general formula (G-VIa) (where $R^{1g}$ and $R^{2g}$ have the same meanings as defined above);

subjecting the compound of the general formula (G-VIa) to halogenation reaction to give a compound of the general formula (D-IIa) (where $R^{1g}$, $R^{2g}$ and Hal have the same meanings as defined above); and subjecting the compound of the general formula (D-IIa) to thermal cyclization reaction.

16. A process according to scheme (5) or (6) in Process 1 for producing 4-substituted benzopyran derivatives represented by the general formula (Iy) set forth below (where $R^1$ in the general formula (I) represents a 6-trifluoromethyl group or a 6-pentafluoroethyl group; $R^2$ represents a hydrogen atom; $R^3$ and $R^4$ both represent a fluoromethyl group; X is a bromine atom) by the steps of:

reacting an alcohol of the general formula (C-Ia) with a compound of the general formula (C-II) or (C-III)

  (C-II)

  (C-III)

(where $R^7$ represents an optionally substituted lower alkyl group or an optionally substituted aryl group) in the presence of a base to give a compound of the general formula (C-IVa) (where $R^7$ has the same meaning as defined above);

reacting the compound of the general formula (C-IVa) with a 4-substituted phenol derivative of the general formula (C-Va) (where $R^{1e}$ has the same meaning as defined above) in the presence of a base and a monovalent or divalent copper salt to give a compound of the general formula (G-VIb) (where $R^{1e}$ has the same meaning as defined above);

subjecting the compound of the general formula (G-VIb) to bromination reaction to give a compound of the general formula (D-IIb) (where $R^{1e}$ has the same meaning as defined above); and subjecting the compound of the general formula (G-IIb) to thermal cyclization reaction.

17. A process according to scheme (5) or (6) in Process 1 for producing 4-substituted benzopyran derivatives represented by the general formula (G-VIz) set forth below, wherein $R^1$ in the general formula (G-VI) represents a 6-trifluoromethyl group or a 6-pentafluoroethyl group; $R^2$ represents a hydrogen atom; $R^3$ and $R^4$ each represent a fluoromethyl group; and $R^5$ and $R^6$ which may be the same or different represent a hydrogen atom or an optionally substituted lower alkyl group.

18. A process according to scheme (5) or (6) in Process 1 for producing 4-substituted benzopyran derivatives represented by the general formula (G-VIy) set forth below, wherein $R^1$ in the general formula (G-VI) represents a 6-trifluoromethyl group or a 6pentafluoroethyl group; $R^2$ represents a hydrogen atom; $R^3$ and $R^4$ each represent a fluoromethyl group; and $R^5$ represents a hydrogen atom and $R^6$ represents a 2-cyanoethyl group.

19. A process according to scheme (5) or (6) in Process 1, which uses a compound of the general formula (C-IVb) as obtained by reacting methanesulfonyl chloride of the general formula (C-II) where $R^7$ is a methyl group with a compound of the general formula (C-I) where $R^3$ and $R^4$ are each a fluoromethyl group.

20. A process according to scheme (5) or (6) in Process 1, which uses a compound of the general formula (C-IVc) (where Tol represents a tolyl group) that is obtained by reacting p-toluenesulfonyl chloride of the general formula (C-II) where $R^7$ is a p-tolyl group with a compound of the general formula (C-I) where $R^3$ and $R^4$ are each a fluoromethyl group in the presence of a base.

21. A process according to scheme (5) or (6) in Process 1, which uses a compound of the general formula (C-VIb) (where $R^{1e}$ has the same meaning as defined above) that is obtained by reacting a compound of the general formula (C-Va) set forth below (where $R^{1e}$ has the same meaning as defined above; $R^1$ in the general formula (C-V) is a 4-trifluoromethyl group or a 4-pentafluoroethyl group and $R^2$ is a hydrogen atom) with a compound of the general formula (C-IVb) or (C-IVc) set forth below, wherein Tol represents a p-tolyl group.

22. A process according to scheme (5) or (6) in Process 1, which uses a compound of the general formula (D-IIb) (where $R^{1e}$ has the same meaning as defined above) that is obtained by brominating a compound of the general formula (C-VIb) set forth below (where $R^{1e}$ has the same meaning as defined above; $R^1$ in the general formula (C-VI) is a 4-trifluoromethyl group or a 4-pentafluoroethyl group; $R^2$ is a hydrogen atom; $R^3$ and $R^4$ are both a fluoromethyl group).

23. A process according to scheme (5) or (6) in Process 1, which uses a 4-bromobenzopyran derivative of the general formula (Iq) (where $R^{1e}$ has the same meaning as defined above) that is obtained by subjecting a compound of the general formula (D-IIb) set forth below (where $R^{1e}$ has the same meaning as defined above; $R^1$ in the general formula (D-II) is a 4-trifluoromethyl group or a 4-pentafluoroethyl group; $R^2$ is a hydrogen atom; $R^3$ and $R^4$ are both a fluoromethyl group; X is a bromine atom) to thermal cyclization reaction.

The general formula (G-1) and the general formula (C-VI) represent substantially the same compound. $R^1$ and $R^{1g}$ represent substantially the same group, so do $R^2$ and $R^{2g}$.

The general formula (C-V) and the general formula (C-Vg) represent substantially the same compound.

The general formulae (C-VIe), (C-VIj) and (C-VIy) represent substantially the same compound.

BEST MODE FOR CARRYING OUT THE INVENTION

As mentioned above, the present invention relates to a process for producing 4-substituted benzopyran derivatives represented by the general formula (G-VI) [where $R^1$ and $R^2$ which may be the same or different represent a hydrogen atom, an optionally substituted lower alkyl group, an optionally substituted lower alkoxy group, an optionally substituted lower alkoxycarbonyl group, an optionally substituted lower alkylsulfonyl group, an optionally substituted arylsulfonyl group, a halogen atom, a nitro group, a cyano group or $NY_aY_b$ (where $Y_a$ and $Y_b$ which may be the same or different each represent a hydrogen atom, an optionally substituted lower alkyl group, an optionally substituted lower alkoxycarbonyl group, an acyl group, an optionally substituted lower alkylsulfonyl group or an optionally substituted arylsulfonyl group or, when taken together with the nitrogen atom to which they are bound, may form a 3- to 8-membered ring) or, when taken together, represent a substituent =N=O—N=; $R^3$ and $R^4$ which may be the same or different represent a hydrogen atom or an optionally substituted lower alkyl group or, when taken together with the carbon atom to which they are bound, represent a polymethylene group or a substituent forming a heterocycle, provided that $R^3$ and $R^4$ are not both a hydrogen atom; $R^5$ and $R^6$ which may be the same or different represent a hydrogen atom or an optionally substituted lower alkyl group] by any one of the schemes (1), (2), (3), (4), (5) and (6) containing a plurality of steps as indicated below, namely, (1): (1-1)→(1-2)→(1-3)→(1-4)→(1-5):
(2): (2-1)→(2-2)→(2-3)→(2-4)→(2-5)→(1-5);
(3): (3-1)→(3-2);
(4): (4-1)→(4-2);
(5): (a-1)→(a-2)→(b-1)→(b-2)→(1-5); and
(6): (a-1)→(a-2)→(d-1)→(d-2)→(d-3).

Referring to the 4-substituted benzopyran derivatives represented by the general formula (G-VI), examples of the optionally substituted lower alkyl group as $R^1$ and $R^2$ include a lower alkyl group, a lower haloalkyl group, a lower perfluoroalkyl group, a lower alkyl group having a halogen atom as a substituent, and an α-haloalkyl group; examples of the optionally substituted lower alkoxy group as $R^1$ and $R^2$ include a lower alkoxy group and a lower haloalkoxy group; examples of $NY_aY_b$ as $R^1$ and $R^2$ include an amino group and an acylamino group.

Examples of the optionally substituted lower alkyl group as $R^3$ and $R^4$ include a lower alkyl group, a substituted lower alkyl group, a lower fluoroalkyl group, a lower alkyl group having a halogen atom as a substituent, and an α-haloalkyl group.

On the pages that follow, the practice of the present invention is described for six different schemes grouped in three, the first consisting of schemes (1) and (2), the second being schemes (3) and (4), and the third being schemes (5) and (6).

A. Schemes (1) and (2):

Speaking of the process according to schemes (1) and (2), the preferred substituents in the 4-substituted benzopyran derivatives of the general formula (G-VI) are exemplified by the following.

Preferably, $R^1$ and $R^2$ which may be the same or different represent a hydrogen atom, a lower alkyl group, a lower haloalkyl group, a halogen atom, a lower haloalkoxy group, an amino group, an acylamino group, a nitro group, a cyano group, an alkoxycarbonyl group, an optionally substituted lower alkylsulfonyl group, an arylsulfonyl group or, when taken together, represent a substituent =N—O—N=.

Preferably, $R^3$ and $R^4$ which maybe the same or different represent a hydrogen atom or an optionally substituted lower alkyl group or, when taken together with the carbon atom to which they are bound, represent a polymethylene group or a substituent forming a heterocycle, provided that $R^3$ and $R^4$ are not both a hydrogen atom.

Preferably, $R^5$ and $R^6$ which may be the same or different represent a hydrogen atom or an optionally substituted lower alkyl group.

In schemes (1) and (2), the term "halogen atom" means a fluorine atom, a chlorine atom, a bromine atom or an iodine atom.

In schemes (1) and (2), the lower alkyl group means a straight-chained or branched alkyl group having 1–4 carbon atoms or a cyclic alkyl group having 3–6 carbon atoms; examples include a methyl group, an ethyl group, a n-propyl group, a n-butyl group, an i-propyl group, an i-butyl group, a sec-butyl group, a tert-butyl group, a cyclopropyl group, a cyclobutyl group, a cyclopentyl group and a cyclohexyl group.

In schemes (1) and (2), the lower alkoxy group means a straight-chained or branched alkoxy group having 1–4 carbon atoms or a cyclic alkoxy group having 3–6 carbon atoms; examples include a methoxy group, an ethoxy group, a n-propoxy group, a n-butoxy group, an i-propoxy group, an i-butoxy group, a sec-butoxy group, a tert-butoxy group, a cyclopropoxy group, a cyclobutoxy group, a cyclopentoxy group and a cyclohexoxy group.

The lower haloalkyl group as $R^1$ and $R^2$ means a straight-chained or branched alkyl group having 1–4 carbon atoms or a cyclic alkyl group having 3–6 carbon atoms, in which at least one hydrogen atom is replaced by a halogen atom; examples include a fluoromethyl group, a difluoromethyl group, a trifluoromethyl group, a fluoroethyl group, a difluoroethyl group, a trifluoroethyl group, a tetrafluoroethyl group, a pentafluoroethyl group, a n-fluoropropyl group, a n-difluoropropyl group, a n-trifluoropropyl group, a n-tetrafluoropropyl group, a n-pentafluoropropyl group, a n-hexafluoropropyl group, a n-heptafluoropropyl group, a n-fluorobutyl group, a n-difluorobutyl group, a n-trifluorobutyl group, a n-tetrafluorobutyl group, a n-pentafluorobutyl group, a n-hexafluorobutyl group, a n-heptafluorobutyl group, a n-octafluorobutyl group, a n-nonafluorobutyl group, an i-fluoropropyl group, an i-difluoropropyl group, an i-trifluoropropyl group, an i-tetrafluoropropyl group, an i-pentafluoropropyl group, an i-hexafluoropropyl group, an i-heptafluoropropyl group, an i-fluorobutyl group, an i-difluorobutyl group, an i-trifluorobutyl group, an i-tetrafluorobutyl group, an i-pentafluorobutyl group, an i-hexafluorobutyl group, an i-heptafluorobutyl group, an i-octafluorobutyl group, an i-nonafluorobutyl group, a sec-fluorobutyl group, a sec-difluorobutyl group, a sec-trifluorobutyl group, a sec-tetrafluorobutyl group, a sec-pentafluorobutyl group, a sec-hexafluorobutyl group, a sec-heptafluorobutyl group, a sec-octafluorobutyl group, a sec-nonafluorobutyl group, a tert-fluorobutyl group, a tert-difluorobutyl group, a tert-trifluorobutyl group, a tert-tetrafluorobutyl group, a tert-pentafluorobutyl group, a tert-hexafluorobutyl group, a tert-heptafluorobutyl group, a tert-octafluorobutyl group, a tert-nonafluorobutyl group, a fluorocyclopropyl group, a difluorocyclopropyl group, a trifluorocyclopropyl group, a tetrafluorocyclopropyl group, a pentafluorocyclopropyl group, afluorocyclobutyl group, a difluorocyclobutyl group, a trifluorocyclobutyl group, a tetrafluorocyclobutyl group, a pentafluorocyclobutyl group, a hexafluorocyclobutyl group, a heptafluorocyclobutyl group, a fluorocyclopentyl group, a difluorocyclopentyl group, a trifluorocyclopentyl group, a tetrafluorocyclopentyl group, a pentafluorocyclopentyl group, a hexafluorocyclopentyl group, a heptafluorocyclopentyl group, an octafluorocyclopentyl group, a nonafluorocyclopentyl group, a fluorocyclohexyl group, a difluorocyclohexyl group, a trifluorocyclohexyl group, a tetrafluorocyclohexyl group, a pentafluorocyclohexyl group, a hexafluorocyclohexyl group, a heptafluorocyclohexyl group, an octafluorocyclohexyl group, a nonafluorocyclohexyl group, a decafluorocyclohexyl group, and an undecafluorocyclohexyl group.

The lower perfluoroalkyl group as $R^1$ means a straight-chained or branched perfluoroalkyl group having 1–4 carbon atoms or a cyclic perfluoroalkyl group having 3–6 carbon atoms; examples include a trifluoromethyl group, a pentafluoroethyl group, a n-heptafluoropropyl group, a n-nonafluorobutyl group, an i-heptafluoropropyl group, an i-nonafluorobutyl group, a sec-nonafluorobutyl group, a tert-nonafluorobutyl group, a pentafluorocyclopropyl group, a heptafluorocyclobutyl group, a nonafluorocyclopentyl group and an undecafluorocyclohexyl. group.

Examples of the optionally substituted lower alkylsulfonyloxy group as X and Y include a methanesulfonyloxy group and a trifluoromethanesulfonyloxy group.

Examples of the arylsulfonyloxy group as X and Y include a benzenesulfonyloxy group and a p-toluenesulfonyloxy group.

The lower haloalkoxy group as $R^1$ and $R^2$ means a straight-chained or branched alkoxy group having 1–4 carbon atoms or a cyclic alkoxy group having 3–6 carbon atoms, in which at least one hydrogen atom is replaced by a halogen atom; examples include a trifluoromethoxy group, a fluoroethoxy group, a difluoroethoxy group, a trifluoroethoxy group, a tetrafluoroethoxy group, a pentafluoroethoxy group, a n-fluoropropoxy group, a n-difluoropropoxy group, a n-trifluoropropoxy group, a n-tetrafluoropropoxy group, a n-pentafluoropropoxy group, a n-hexafluoropropoxy group, a n-heptafluoropropoxy group, a n-fluorobutoxy group, a n-difluorobutoxy group, a n-trifluorobutoxy group, a n-tetrafluorobutoxy group, a n-pentafluorobutoxy group, a n-hexafluorobutoxy group, a n-heptafluorobutoxy group, a n-octafluorobutoxy group, a n-nonafluorobutoxy group, an i-fluoropropoxygroup, an i-difoluoropropoxy group, an i-trifluoropropoxy group, an i-tetrafluoropropoxy group, an i-pentafluoropropoxy group, an i-hexafluoropropoxy group, an i-heptafluoropropoxy group, an i-fluorobutoxy group, an i-difluorobut oxy group, an i-trifluorobutoxy group, an 1-tetrafluorobutoxy group, an i-pentafluorobutoxy group, an i-hexafluorobutoxy group, an i-heptafluorobutoxy group, an i-octafluorobutoxy group, an i-nonafluorobutoxy group, a sec-fluorobutoxy group, a sec-difluorobutoxy group, a sec-trifluorobutoxy group, a sec-tetrafluorobutoxy group, a sec-pentafluorobutoxy group, a sec-hexafluorobutoxy group, a sec-peptafluorobutoxy group, a sec-octafluorobutoxy group, a sec-nonafluorobutoxy group, a tert-fluorobutoxy group, a tert-difluorobutoxy group, a tert-trifluorobutoxy group, a tert-tetrafluorobutoxy group, a tert-pentafluorobutoxy group, a tert-hexafluorobutoxy group, a tert-heptafluorobutoxy group, a tert-octafluorobuoxty group, a tert-nonafluorobutoxy group, a fluorocyclopropoxy group, a difluorocyclopropoxy group, a trifluorocyclopropoxy group, a tetrafluorocyclopropoxy group, a pentafluorocyclopropoxy group, a fluorocyclobutoxy group, a difluorocyclobutoxy group, a trifluorocyclobutoxy group, a tetrafluorocyclobutoxy group, a pentafluorocyclobutoxy group, a hexafluorocyclobutoxy group, a heptafluorocyclobutoxy group, a fluorocyclopentoxy group, a difluorocyclopentoxy group, a trifluorocyclopentoxy group, a tetrafluorocyclopentoxy group, a pentafluorocyclopentoxy group, a hexafluorocyclopentoxy group, a heptafluorocyclopentoxy group, an octafluorocyclopentoxy group, a nonafluorocyclopentoxy group, a fluorocyclohexoxy group, a difluorocyclohexoxy group, a trifluorocyclohexoxy group, a d tetrafluorocyclohexoxy group, a pentafluorocyclohexoxy group, a hexafluorocyclohexoxy group, a heptafluorocyclohexoxy group, an octafluorocyclohexoxy group, a nonafluorocyclohexoxy group, a decafluorocyclohexoxy group, and an undecafluorocyclohexoxy group.

The acylamino group as $R^1$ and $R^2$ means an amino group in which one of the hydrogen atoms present is replaced by an acyl group and exemplary acyl groups include a formyl group, an acetyl group, a trifluoroacetyl group, a propanoyl group, a n-butanoyl group, an i-butanoyl group, a pivaloyl group, a benzoyl group, an anisoyl group, and a nitrobenzoyl group.

Examples of the alkoxycarbonyl group as $R^1$ and $R^2$ include a methoxycarbonyl group, an ethoxycarbonyl group, a tert-butoxycarbonyl group, a benzyloxycarbonyl group, a methoxybenzylcarbonyl group and a nitrobenzylcarbonyl group.

Examples of the optionally substituted lower alkylsulfonyl group as $R^1$ and $R^2$ include a methanesulfonyl group and a trifluoromethanesulfonyl group.

Examples of the arylsulfonyl group as $R^1$ and $R^2$ include a benzensulfonyl group and a p-toluenesulofnyl group.

Examples of the substituent in the optionally substituted lower alkyl group as $R^3$ and $R^4$ include a halogen atom, a phenyl group, a hydroxyl group, a lower alkoxy group optionally substituted by a halogen atom or a phenyl group, and a lower alkylthio group optionally substituted by a halogen atom or a phenyl group. Preferred are halogen atoms, among which a fluorine atom is particularly preferred.

Examples of the optionally substituted lower alkyl group as $R^3$ and $R^4$ include a fluoromethyl group, a difluoromethyl group, a trifluoromethyl group, a fluoroethyl group, a difluoroethyl group, a trifluoroethyl group, a tetrafluoroethyl group, a pentafluoroethyl group, a n-fluoropropyl group, a n-difluoropropyl group, a n-trifluoropropyl group, a n-tetrafluoropropyl group, a n-pentafluoropropyl group, a n-hexafluoropropyl group, a n-heptafluoropropyl group, a n-fluorobutyl group, a n-difluorobutyl group, a n-trifluorobutyl group, a n-tetrafluorobutyl group, a n-pentafluorobutyl group, a n-hexafluorobutyl group, a n-heptafluorobutyl group, a n-octafluorobutyl group, a n-nonafluorobutyl group, an i-fluoropropyl group, an i-difluoropropyl group, an i-trifluoropropyl group, an i-tetrafluoropropyl group, an i-pentafluoropropyl group, an i-hexafluoropropyl group, an i-heptafluoropropyl group, an i-fluorobutyl group, an i-difluorobutyl group, an i-trifluorobutyl group, an i-tetrafluorobutyl group, an i-pentafluorobutyl group, an i-hexafluorobutyl group, an i-heptafluorobutyl group., an i-octafluorobutyl group, an i-nonafluorobutyl group, a sec-fluorobutyl group, a sec-difluorobutyl group, a sec-trifluorobutyl group, a sec-tetrafluorobutyl group, a sec-pentafluorobutyl group, a sec-hexafluorobutyl group, a sec-heptafluorobutyl group, a sec-octafluorobutyl group, a sec-nonafluorobutyl group, a tert-fluorobutyl group, a tert-difluorobutyl group, a tert-trifluorobutyl group, a tert-tetrafluorobutyl group, a tert-pentafluorobutyl group, a tert-hexafluorobutyl group, a tert-heptafluorobutyl group, a tert-octafluorobutyl group, a tert-nonafluorobutyl group, a benzyl group, a methoxymethyl group, an ethoxymethyl group, a trifluoromethoxymethyl group, a benzyloxymethyl group, a methylthiomethyl group, an ethylthiomethyl group, and a methoxycarbonylmethyl group.

The lower fluoroalkyl group as $R^3$ and $R^4$ means a straight-chained or branched alkoxy group having 1–4 carbon atoms in which at least one hydrogen atom is replaced by a fluorine atom; examples include a fluoromethyl group, a difluoromethyl group, a trifluoromethyl group, a fluoroethyl group, a difluoroethyl group, a trifluoroethyl group, a tetrafluoroethyl group, a pentafluoroethyl group, a n-fluoropropyl group, a n-difluoropropyl group, a n-trifluoropropyl group, a n-tetrafluoropropyl group, a n-pentafluoropropyl group, a n-hexafluoropropyl group, a n-heptafluoropropyl group, a n-fluorobutyl group, a n-difluorobutyl group, a n-trifluorobutyl group, a n-tetrafluorobutyl group, a n-pentafluorobutyl group, a n-hexafluorobutyl group, a n-heptafluorobutyl group, a n-octafluorobutyl group, a n-nonafluorobutyl group, an i-fluoropropyl group, an i-difluoropropyl group, an i-trifluoropropyl group, an i-tetrafluoropropyl group, an i-pentafluoropropyl group, an i-hexafluoropropyl group, an i-heptafluoropropyl group, an i-fluorobutyl group, an i-difluorobutyl group, an i-trifluorobutyl group, an i-tetrafluorobutyl grop up, an pentafluorobutyl group, an i-hexafluorobutyl group, an i-heptafluorobutyl group, an i-octafluorobutyl group, an i-nonafluorobutyl group, a sec-fluorobutyl group, a sec-difluorobutyl group, a sec-trifluorobutyl group, a sec-tetrafluorobutyl group, a sec-pentafluorobutyl group, a sec-hexafluorobutyl group, a sec-heptafluorobutyl group, a sec-octafluorobutyl group, a sec-nonafluorobutyl group, a tert-fluorobutyl group, a tert-difluorobutyl group, a tert-trifluorobutyl group, a tert-tetrafluorobutyl group, a tert-pentafluorobutyl group, a tert-hexafluorobutyl group, a tert-heptafluorobutyl group, a tert-octafluorobutyl group, and a tert-nonafluorobutyl group.

If $R^3$ and $R^4$ represent substituents which, when taken together with the carbon atom to which they are bound, form a polymethylene group, they are saturated spiro rings having 3–7 carbon atoms, as exemplified by a cyclopropane ring, a cyclobutane ring, a cyclopentane ring, a cyclohexane ring and a cycloheptane ring.

If $R^3$ and $R^4$ represent substituents which, when taken together with the carbon atom to which they are bound, form a heterocycle, they are saturated spiro heterocycles having 3–7 carbon atoms which contain a hetero atom, as exemplified by an azetidine ring, pyrrolidine ring, a piperidine ring, an oxetane ring, a tetrahydrofuran ring, a tetrahydropyran ring, a tetrahydrothiophene ring, and a tetrahydrothiopyran ring.

Preferred examples of X are an iodine atom, a bromine atom and a trifluoromethanesulfonyloxy group.

Preferred examples of Y include a fluorine atom, a chlorine atom, a methanesulfonyloxy group, a benzenesulfonyloxy group and a p-toluenesulfonyl group; among these, a fluorine atom and a chlorine atom are particularly preferred.

While X and Y may be the same or different, they are preferably different.

There are two preferred combinations of X and Y; in one combination, X is a bromine atom and Y is a chlorine atom and in the other combination, X is an iodine atom and Y is a chlorine atom.

Preferred examples of $R^1$ are a lower perfluoroalkyl group, a nitro group and a cyano group; among these, lower perfluoroalkyl groups are preferred, with a trifluoromethyl group and a pentafluoroethyl group being particularly preferred.

The preferred position of substitution by $R^1$ is in 6-position on the benzopyran ring.

The preferred example of $R^2$ is a hydrogen atom.

It is preferred that $R^3$ and $R^4$ are the same; more preferably, they both are a lower alkyl group or a lower fluoroalkyl group; most preferably, they both are a fluoromethyl group.

Examples of the optionally substituted lower alkyl group as $R^5$ and $R^6$ include a methyl group, a benzyl group, a cyclopropylmethyl group, an ethyl group, a 2-cyanoethyl group, a 2-fluoroethyl group and a n-propyl group.

Preferably, $R^5$ is a hydrogen. atom and $R^6$ is an optionally substituted lower alkyl group; more preferably, $R^5$ is a hydrogen atom and $R^6$ is a lower alkyl group optionally having a cyano group; most preferably, $R^5$ is a hydrogen atom and $R^6$ is a 2-cyanoethyl group or a 2-cyanomethyl group.

A compound represented by the general formula (II) (where X and Y have the same meanings as defined above; $R^1$ and $R^2$ have the same meanings as defined above) is reacted with an olefin represented by the general formula (III) (where $R^3$ and $R^4$ have the same meanings as defined above) in a suitable solvent in the presence of a suitable metal catalyst, a suitable base and a suitable quaternary ammonium salt under an inert atomosphere at a suitable temperature to give a compound represented by the general formula (IV) (where Y, $R^1$, $R^2$, $R^3$ and $R^4$ have the same meanings as defined above). The suitable metal catalyst as used herein means a palladium or a nickel catalyst and examples include palladium acetate, palladium chloride, palladium carbon, bis(triphenylphosphine)palladium acetate, bis(triphenylphosphine)palladium chloride, tris(dibenzylideneacetone)dipalladium, bis(dibenzylideneacetone)palladium, tetrakis(triphenylphosphine)palladium, [1,1'-bis(diphenylphosphino)ferrocene]palladium chloride, allyl palladium chloride, bis(acetonitrile)palladium chloride, nickel acetate, nickel chloride, bis(1,5-octadiene)nickel, bis(triphenylphosphine)nickel chloride, dicyclopentadienyl nickel, and nickel acetoacetonate; among these, palladium acetate is preferred. Examples of the suitable base include diethylamine, triethylamine, diisopropylethylamine, sodium hydrogencarbonate, sodium carbonate, potassium hydrogencarbonate, potassium carbonate, dipotassium hydrogenphosphate, potassium phosphate, sodium hydroxide and potassium hydroxide; among these, potassium carbonate is preferred. Examples of the suitable quaternary ammonium salt include tetrabutylammonium iodide, tetrabutylammonium bromide, tetrabutylammonium chloride, benzyltriethylammonium chloride and benzyltrimethylammonium hydroxide; among these, tetrabutylammonium bromide is preferred. Examples of the suitable solvent include N,N-dimethylformamide, N,N-dimethylacetamide, toluene, xylene, acetonitrile and dioxane; among these, N,N-dimethylacetamide is preferred. An example of the suitable temperature is between room temperature and 130° C., preferably between 75° C. and 85° C. Examples of the inert gas are nitrogen and argon.

The resulting compound of the general formula (IV) is reacted with a halogenating agent (e.g. bromine) in a suitable solvent at a suitable temperature to give a compound represented by the general formula (V) (where Y, $R^1$, $R^2$, $R^3$, $R^4$ and Hal have the same meanings as defined above). Examples of the suitable solvent include dichloromethane, chloroform, carbon tetrachloride, 1,2-dichloroethane, diethyl ether, tert-butyl methyl ether, tert-butyl alcohol, tert-amyl alcohol, 3-methyl-3-pentanol and 3-ethyl-3-pentanol; among these, tert-amyl alcohol is preferred. An example of the suitable temperature is between –78° C. and 80° C., preferably between –15° C. and –5° C.

The resulting compound of the general formula (V) is reacted with a suitable base in a suitable solvent at a suitable temperature to give a compound represented by the general formula (VI) (where Y, $R^1$, $R^2$, $R^3$, $R^4$ and Hal have the same meanings as defined above). Examples of the suitable base include diethylamine, triethylamine, diisopropylethylamine, sodium hydride, potassium hydride, potassium tert-butoxide, sodium methoxide, sodium ethoxide, sodium bis(trimethylsilyl)amide, potassium bis(trimethylsilyl)amide, soium hydrogencarbonate, sodium carbonate, potassium hydrogencarbonate, potassium carbonate, dipotassium hydrogenphosphate, potassium phosphate, sodium hydroxide and potassium hydroxide; among these, sodium hydride and potassium carbonate are preferred. Examples of the suitable solvent include dichloromethane, chloroform, carbon tetrachloride, 1,2-dichloroethane, tert-butyl alcohol, tert-amyl alcohol, 3-methyl-3-pentanol, 3-ethyl-3-pentanol, tetrahydrofuran, dioxane, N,N-dimethylformamide, N,N-dimethylacetamide, toluene and xylene; among these, toluene and tert-amyl alcohol are preferred. An example of the suitable temperature is between –78° C. and 80° C., preferably between 30° C. and 60° C.

The resulting compound of the general formula (VI) is reacted with a suitable base in asuitable solvent at a suitable temperature to give a compound represented by the general formula (I) (where $R^1$, $R^2$, $R^3$, $R^4$ and Hal have the same meanings as defined above). Examples of the suitable base include sodium hydride, potassium hydride, potassium tert-butoxide, sodium bis(trimethylsilyl)amide and potassium bis(trimethylsilyl)amide; among these, sodium hydride and potassium bis(trimethylsilyl)amide are preferred. Examples of the preferred suitable solvent include tetrahydrofuran, dioxane, N,N-dimethylformamide, N,N-dimethylacetamide, toluene and xylene; among these, toluene and tetrahydrofuran are preferred. An example of the suitable temperature is between −78° C. and 80° C., preferably between −15° C. and −5° C.

The compound of the general formula (I) can also be prepared by the following scheme. Namely, a compound represented by the general formula (II) (where X, Y, $R^1$ and $R^2$ have the same meanings as defined above) is reacted with acetylene represented by the general formula (VII) (where $R^3$ and $R^4$ have the same meanings as defined above) in a suitable solvent in the presence of a suitable metal catalyst, a suitable ligand, a suitable copper salt and a suitable base in an inert atmosphere at a suitable temperature to give a compound represented by the general formula ((VIII) (where Y, $R^1$, $R^2$, $R^3$ and $R^4$ have the same meanings as defined above). The suitable metal catalyst as used herein means a palladium or a nickel catalyst and examples include palladium acetate, palladium chloride, palladium carbon, nickel acetate and nickel chloride; alternatively, the metal catalyst is a complex with a ligand, as exemplified by bis(triphenylphosphine)palladium acetate, bis(triphenylphosphine)palladium chloride, tris(dibenzylideneacetone)dipalladium, bis(dibenzylideneacetone)palladium, tetrakis(triphenylphosphine)palladium, [1,1'-bis(diphenylphosphino)ferrocene]palladium chloride, allyl palladium chloride, bis(acetonitrile)palladium chloride, bis(1,5-octadiene)nickel, bis(triphenylphosphine)nickel chloride, dicyclopentadienyl nickel and nickel acetoacetonate. Examples of the suitable ligand include triphenylphosphine, tris(o-tolyl)phosphine, 1,1'-bis(diphenylphosphino)ferrocene and dibenzylidene acetone; among these bis(triphenylphosphine)palladium chloride is preferred. Examples of the suitable copper salt include a copper(0) powder, cuprous chloride, cuprous bromide, cuprous iodide and cuprous acetate; among these, cuprous iodide is preferred. Examples of the suitable base include diethylamine, triethylamine, diisopropylethylamine, sodium hydrogencarbonate, sodium carbonate, potassium hydrogencarbonate, potassium carbonate, dipotassium hydrogenphosphate, potassium phosphate, sodium hydroxide and potassium hydroxide; among these, triethylamine being preferred. Examples of the suitable solvent include triethylamine, N,N-dimethylformamide, N,N-dimethylacetamide, toluene, xylene, acetonitrile and dioxane; among these, N,N-dimethylformamide is preferred. An example of the preferred temperature is between room temperature and 130° C., preferably between 75° C. and 85° C. Examples of the inert gas include nitrogen and argon.

The resulting compound of the general formula (VIII) is subjected to reaction under a hydrogen atmosphere in the presence of a suitable catalyst and a suitable solvent at a suitable temperature to give a compound represented by the general formula (IX) (where Y, $R^1$, $R^2$, $R^3$ and $R^4$ have the same meanings as defined above). Examples of the suitable catalyst include a Lindlar catalyst, developed Raney nickel, barium carbonate-palladium and barium sulfate-palladium, with 5% palladium-bariuxm carbonate being preferred. Examples of the suitable solvent include methanol, ethanol, ethyl acetate and methanol-pyridine, with 5% pyridine-methanol and ethyl acetate being preferred. An example of the suitable temperature is between room temperature and 60° C. preferably room temperature.

The resulting compound of the general formula (IX) is reacted with a suitable base in a suitable solvent at a suitable temperature to give a compound represented by the general formula (X) (where $R^1$, $R^2$, $R^3$ and $R^4$ have the same meanings as defined above). Examples of the suitable base include sodium hydride, potassium hydride, potassium tert-butoxide, sodium-bis(trimethylsilyl)amide and potassium bis(trimethylsilyl)amide, with potassium tert-butoxide being preferred. Examples of the suitable solvent include tetrahydrofuran, dioxane, N,N-dimethylformamide, N,N-dimethylacetamide, 1,3-dimethylimidazolidin-2-one, N-methylpyrrolidone, sulfolane, toluene and xylene, with N,N-dimethylformamide being preferred. An example of the suitable temperature is between −78° C. and 80° C., preferably between 55° C. and 65° C.

The resulting compound of the general formula (X) is reacted with a halogenating agent (e.g. bromine) in a suitable solvent at a suitable temperature to give a compound represented by the general formula (XI) (where $R^1$, $R^2$, $R^3$, $R^4$ and Hal have the same meanings as defined above). Examples of the suitable solvent include dichloromethane, chloroform, carbon tetrachloride, 1,2-dichloroethane, diethyl ether and tert-butyl methyl ether, with chloroform and tert-butyl methyl ether being preferred. An example of the preferred temperature is between −78° C. and room temperature, preferably between −10° C. and room temperature.

The resulting compound of the general formula (XI) is reacted with a suitable base in a suitable solvent at a suitable temperature to give a compound represented by the general formula (I) (where $R^1$, $R^2$, $R^3$, $R^4$ and Hal have the same meanings as defined above). Examples of the suitable base include sodium hydride, potassium hydride, potassium tert-butoxide, sodium hydrogencarbonate, sodium carbonate, potassium hydrogencarbonate, potassium carbonate, dipotassium hydrogenphosphate, potassium phosphate, sodium hydroxide and potassium hydroxide, with potassium hydroxide being preferred. Examples of the suitable solvent include water, tetrahydrofuran, dioxane, N,N-dimethylformamide, N,N-dimethylacetamide, toluene, xylene, methanol and ethanol, with water-dioxane and ethanol being preferred. An example of the suitable temperature is between −78° C. and 80° C., preferably between room temperature and 80° C.

The resulting compound of the general formula (I) is converted to a compound of the general formula (G-VI) by a method that involves a carbon monoxide inserting cross-coupling reaction as a key reaction that uses a metal as a catalyst. To be specific, the compound of the general formula (I) (where $R^1$, $R^2$, $R^3$, $R^4$ and Hal have the same meanings as defined above) is subjected to a cross-coupling reaction with a compound of the general formula (G-III)

$$HNR^5R^6 \tag{G-III}$$

(where $R^5$ and $R^6$ have the same meanings as defined above) under a carbon monoxide gas at atmospheric or superatmospheric pressure from a CO gas container, preferably at atmospheric pressure, at a reaction temperature between −78° C. and 150° C., preferably between room temperature and 130° C., for a reaction time of from 1 hour to 3 days, preferably from 3 hours to 1 day, in the presence of a zero-valence or divalent metal catalyst such as palladium, nickel, copper, zinc, tin or magnesium, preferably, 1–5 mol % of zero-valence or divalent palladium such as bis(triphenylphosphine)palladium acetate, palladium acetate and triphenylphosphine, bis(triphenylphosphine)palladium chloride, [1,1'-bis(diphenylphosphino)ferrocene]palladium chloride dichloromethane adduct, tetrakis(triphenylphosphine)palladium, tris(dibenzylideneacetone)dipalladium chloroform adduct and triphenylphosphine, and tris(dibenzylideneacetone)dipalladium chloroform adduct in a solvent such as N,N-dimethylformamide, tetrahydrofuran, dioxane, ether, acetonitrile, toluene, benzene or water, preferably N,N-dimethylformamide, thereby giving a 4-substituted benzopyran derivative represented by the general formula (G-VI) (where $R^1$, $R^2$, $R^3$, $R^4$, $R^5$ and $R^6$ have the same meanings as defined above).

B. Schemes (3) and (4):

Speaking of the process according to schemes (3) and (4), the preferred substituents in the 4-substituted benzopyran derivatives of the general formula (G-VI) are exemplified by the following.

Preferably, $R^1$ and $R^2$ which may be the same or different represent a hydrogen atom, an optionally substituted lower alkyl group, an optionally substituted lower alkoxy group, an optionally substituted lower alkoxycarbonyl group, an optionally substituted lower alkylsulfonyl group, an optionally substituted arylsulfonyl group, a halogen atom, a nitro group, a cyano group or $NY_aY_b$ (where $Y_a$ and $Y_b$ which may be the same or different each represent a hydrogen atom, an optionally substituted lower alkyl group, an optionally substituted lower alkoxycarbonyl group, an acyl group, an optionally substituted lower alkylsulfonyl group or an optionally substituted arylsulfonyl group or, when taken together with the nitrogen atom to which they are bound, may form a 3- to 8-membered ring).

Preferably, $R^3$ and $R^4$ which may be the same or different represent a hydrogen atom or an optionally substituted α-haloalkyl group, provided that they are not both a hydrogen atom.

Preferably, $R^5$ and $R^6$ which may be the same or different represent a hydrogen atom or an optionally substituted lower alkyl group.

In schemes (3) and (4), unless otherwise noted, the following definitions hold:

the lower alkyl group means a straight-chained alkyl group having 1–6 carbon atoms or a branched or cyclic alkyl group having 3–8 carbon atoms; examples include a methyl group, an ethyl group, a n-propyl group, a n-butyl group, a n-pentyl group, a n-hexyl group, an i-propyl group, an i-butyl group, a sec-butyl group, a tert-butyl group, an i-pentyl group, a neopentyl group, a tert-pentyl group, an i-hexyl group, a cyclopropyl group, a cyclobutyl group, a cyclopentyl group, a cyclohexyl group, a cycloheptyl group and a cyclooctyl group;

the halogen atom means a fluorine atom, a chlorine atom, a bromine atom or an iodine atom;

the lower alkoxy group means a straight-chained alkoxy group having 1–6 carbon atoms or a branched or cyclic alkoxy group having 3–8 carbon atoms; examples include a methoxy group, an ethoxy group, a n-propoxy group, a n-butoxy group, a n-pentoxy group, a n-hexoxy group, an i-propoxy group, an i-butoxy group, a sec-butoxy group, a tert-butoxy group, an i-pentoxy group, a neopentoxy group, a tert-pentoxy group, an i-hexoxy group, a cyclopropoxy group, a cyclobutoxy group, a cyclopentoxy group, a cyclohexoxy group, a cycloheptoxy group and a cyclooctoxy group.

the lower alkoxycarbonyl group means an alkoxycarbonyl group whose alkyl portion is a straight-chained alkyl group having 1–6 carbon atoms or an alkoxycarbonyl group whose alkyl portion is a branched or cyclic alkyl group having 3–8 carbon atoms, and examples include a methoxycarbonyl group, an ethoxycarbonyl group, a n-propoxycarbonyl group, a n-butoxycarbonyl group, a n-pentoxycarbonyl group, a n-hexoxycarbonyl group, an i-propoxycarbonyl group, an i-butoxycarbonyl group, a sec-butoxycarbonyl group, a tert-butoxycarbonyl group, an i-pentoxycarbonyl group, a neopentoxycarbonyl group, a tert-pentoxycarbonyl group, an i-hexoxycarbonyl group, a cyclopropoxycarbonyl group, a cyclobutoxycarbonyl group, a cyclopentoxycarbonyl group, a cyclohexoxycarbonyl group, a cycloheptoxycarbonyl group and a cyclooctoxycarbonyl group;

the lower alkylsulfonyl group means an alkylsulfonyl group having 1–8 carbon atoms whose alkyl portion is a straight-chained alkyl group or an alkylsulfonyl group having 3–8 carbon atoms whose alkyl portion is a branched or cyclic alkyl group, and examples include a methylsulfonyl group, an ethylsulfonyl group, a propylsulfonyl group, an isopropylsulfonyl group, a butylsulfonyl group and an isobutylsulfonyl group.

the arylsulfonyl group means an aromatic sulfonyl group and examples include a phenylsulfonyl group, a p-tolylsulfonyl group, a p-chlorophenylsulfonyl group, a 2-furylsulfonyl group, a 3-furylsulfonyl group, a 2-thienylsulfonyl group, a 3-thienylsulfonyl group, a 2-pyridylsulfonyl group, a 3-pyridylsulfonyl group and a 4-pyridylsulfonyl group.

$Y_a$ and $Y_b$ in $NY_aY_b$ which may be the same or different each represent a hydrogen atom, an optionally substituted lower alkyl group, an optionally substituted lower alkoxycarbonyl group, an acyl group, an optionally substituted lower alkylsulfonyl group or an optionally substituted arylsulfonyl group or, when taken together with the nitrogen atom to which they are bound, may form a 3- to 8-membered ring.

The acyl group as used herein means a formyl group or an alkylcarbonyl group having 1–8 carbon atoms whose alkyl portion is an optionally substituted straight-chained alkyl group, an alkylcarbonyl group having 3–8 carbon atoms whose alkyl portion is an optionally substituted branched or cyclic alkyl group, or an arylcarbonyl group, and examples include a formyl group, an acetyl group, a trifluoroacetyl group, a propionyl group, a butyryl group, a valeryl group, an isobutyryl group, an isovaleryl group, a pivaloyl group, a benzoyl group, a phthaloyl group and a toluoyl group.

When either one of $Y_a$ and $Y_b$ is a hydrogen atom and the other is an acyl group, $NY_aY_b$ represents an acylamino group.

When both $Y_a$ and $Y_b$ are a hydrogen atom, $NY_aY_b$ represents an amino group.

If $R^1$, $R^2$, $R^3$, $R^4$, $R^5$ or $R^6$ represents an optionally substituted lower alkyl group, an optionally substituted lower alkoxy group, an optionally substituted lower alkoxycarbonyl group or an optionally substituted lower alkylsulfonyl group, the optionally present substituent may be exemplified by a halogen atom, a phenyl group, a hydroxy group, a nitro group, a cyano group, a cyclic alkyl group having 3–8 carbon atoms, a lower alkoxy group optionally substituted by a halogen atom or a phenyl group, a lower alkoxycarbonyl group, a carboxyl group and $NY_cY_d$; $Y_c$ and $Y_d$ which may be the same or different each represent a hydrogen atom, a lower alkyl group, a lower alkoxycarbonyl group, an acyl group, a lower alkylsulfonyl group or an optionally substituted arylsulfonyl group or, when taken together with the nitrogen atom to which they are bonded, may form a 3- to 8-numbered ring.

When taken together with the nitrogen atom to which they are bound, $Y_a$ and $Y_b$, $Y_c$ and $Y_d$, or $Y_e$ and $Y_f$ may form a 3- to 8-membered ring and the ring has 2–7 carbon atoms, with any carbon atom on the ring being optionally replaced by a nitrogen atom, an oxygen atom or a sulfur atom. Specific examples include an aziridine ring, an azetidine ring, a pyrrole ring, a pyrrolidine ring, a pyridine ring, a 3,4-dihydro-2H-azepine ring, a 3,4,5,6-tetrahydro-2H-azepine ring, an azocine ring, a 5,6-dihydro-azocine ring, a 5,6,7,8-tetrahydroazocine ring, an oxazoline ring, an isoxazoline ring, a thioxazoline ring, a piperazine ring, a morpholine ring and a thiomorpholine ring.

The α-haloalkyl group as $R^3$ and $R^4$ means a straight-chained alkyl group having 1–6 carbon atoms or a branched or cyclic alkyl group having 3–8 carbon atoms that have 1–3 halogen atoms in 1-position and which may further possess a substituent, and examples include a fluoromethyl group, a difluoromethyl group, a trifluoromethyl group, a 1-fluoroethyl group, a 1,1-difluoroethyl group, a 1-fluoropropyl group, a 1,1-difluoropropyl group, a 1-fluorocyclopropyl group, a 1-fluorobutyl group, a 1,1-difluorobutyl group, a chloromethyl group, a dichloromethyl group, a trichloromethyl group, a. -chloroethyl group, a 1,1-dichloroethyl group, a 1-chloropropyl group, a 1,1-chloropropyl group, a 1-chlorocyclopropyl group, a 1-chlorobutyl group, a 1,1-dichlorobutyl group, a bromomethyl group, a dibromomethyl group, a tribromomethyl group, a 1-bromoethyl group, a 1,1-dibromoethyl group, a 1-bromopropyl group, a 1,1-dibromopropyl group, a 1-bromocyclopropyl group, a 1-bromobutyl group, a 1,1-dibromobutyl group, an iodomethyl group, a diodomethyl group, a triiodomethyl group, a 1-iodoethyl group, a 1, i-diiodoethyl group, a 1-iodopropyl group, a 1,1-diiodopropyl group, a 1-iodocyclopropyl group, a 1-iodobutyl group and a 1,1-dijodobutyl group.

If $R^1$ or $R^2$ represents an optionally substituted arylsulfonyl group or an optionally substituted aryl group, the optionally present substituent may be exemplified by a halogen atom, a phenyl group, a hydroxy group, a nitro group, a cyano group, a straight-chained alkyl group having 1–6 carbon atoms, a branched or cyclic alkyl group having 3–8 carbon atoms, a lower alkoxy group optionally substituted by a halogen atom or a phenyl group, a lower alkylthio group optionally substituted by a halogen atom or a phenyl group, a lower alkoxycarbonyl group, a carboxyl group and $NY_eY_f$; $Y_e$ and $Y_f$ which may be the same or different each represent a hydrogen atom, an optionally substituted lower alkyl group, an optionally substituted lower alkoxycarbonyl group, an acyl group, an optionally substituted lower alkylsulfonyl group or an arylsulfonyl group or, when taken together, may form a 3- to 8-numbered ring.

Examples of the optionally substituted lower alkyl group as $R^1$ and $R^2$ include a methyl group, a fluoromethyl group, a trifluoromethyl group, a pentafluoroethyl group, a benzyl group, a nitromethyl group, a cyclopropylmethyl group, a methoxymethyl group, an ethoxymethyl group, a benzyloxymethyl group, a methylthiomethyl group, an ethylthiomethyl group, a methoxycarbonylmethyl group, a dimethylaminomethyl group, an ethyl group, a 2-fluoroethyl group, a n-propyl group, an i-propyl group, a 1-methylthiopropyl group and a n-butyl group.

Examples of the optionally substituted lower alkyl group as $R^5$, $R^6$ and $R^{6a}$ include a methyl group, a benzyl group, a cyclopropylmethyl group, an ethyl group, a 2-cyanoethyl group, a 2-fluoroethyl group and a n-propyl group.

Speaking of $R^5$ and $R^6$, a preferred case is where $R^5$ is a hydrogen atom and $R^6$ is an optionally substituted lower alkyl group; a more preferred case is where $R^5$ is a hydrogen atom and $R^6$ is a lower alkyl group optionally having a cyano group, and a particularly preferred case is where $R^5$ is a hydrogen atom and $R^6$ is a 2-cyanoethyl group or a 2-cyanomethyl group.

A preferred example of $R^{6a}$ is a lower alkyl group optionally having a cyano group; more preferred examples are a 2-cyanoethyl group and a 2-cyanomethyl group, with a 2-cyanoethyl group being particularly preferred.

Examples of the optionally substituted lower alkoxy group as $R^1$ and $R^2$ include a methoxy group, a trifluoromethoxy group, a benzyloxy group, a cyclopropylmethoxy group, an ethoxy group and a n-propoxy group.

Examples of the optionally substituted lower alkoxycarbonyl group as $R^1$ and $R^2$ include a methoxycarbonyl group, a trifluoromethoxycarbonyl group, a benzyloxycarbonyl group, a cyclopropylmethoxycarbonyl group, an ethoxycarbonyl group, a n-propoxycarbonyl group and a tert-butoxycarbonyl group.

The preferred position of substitution by $R^1$ is in 6-position on the benzopyran ring. Preferred examples of $R^1$ include an optionally substituted lower alkyl group, an optionally substituted alkylsulfonyl group, an optionally substituted arylsulfonyl group, a nitro group and a cyano group; among these, lower alkyl groups having a fluorine atom as a substituent are preferred, with a 6-trifluoromethyl group and a 6-pentafluoroethyl group being particularly preferred.

The preferred example of $R^2$ is a hydrogen atom.

Speaking of $R^3$ and $R^4$, they are preferably the same; more preferably, they both are an optionally substituted α-haloalkyl group; most preferably, they both are a fluoromethyl group.

Examples of the optionally substituted alkyl group as $R^7$ include a methyl group, an ethyl group and a propyl group. Examples of the optionally substituted aryl group as $R^7$ include a phenyl group, a p-tolyl group and a p-chlorophenyl group; among these, a p-tolyl group and a methyl group are preferred, with a p-tolyl group being particularly preferred.

Examples of the above-mentioned $NY_aY_b$, $NY_cY_d$ and $NY_eY_f$ include an amino group, a methylamino group, a benzylamino group, an ethylamino group, a dimethylamino group, an ethylmethylamino group, a pyrrolidinyl group, a piperidino group, a morpholino group, an acetamido group, a benzamido group, an N-methylacetamido group, a tert-butoxycarbonylamino group, an N-methyl-tert-butoxycarbonylamino group, a methylsulfonylamino group, an ethylsulfonylamino group, a propylsulfonylamino group, an isopropylsulfonylamino group, a butylsulfonylamino group, an isobutylsulfonylamino group, a phenylsulfonylamino group, a p-tolylsulfonylamino group and a p-chlorophenylsulfonylamino group.

For synthesis of the compound represented by the general formula (G-II), the compound represented by the general formula (G-I) is used as an intermediate and this compound, being undocumented and novel, constituents the present invention. To give the compound of the general formula (G-I), a sulfonate ester represented by the general formula (C-IV) (where $R^7$, $R^3$ and $R^4$ have the same meanings as defined above) may be reacted with a phenol represented by the general formula (C-V) (where $R^1$ and $R^2$ have the same meanings as defined above) in an inert solvent such as acetonitrile that does not affect the reaction, in the presence of a suitable base and a catalytic amount of a suitable copper salt at a temperature between −78° C. and room temperature, preferably between 0° C. and room temperature. Examples of the suitable base that can be used in the reaction include organic strong bases such as 1,8-diazabicyclo(5.4.0)-7-undecene and 1,5-diazabicyclo(4.3.0)-5-nonene, and tertiary amines such as triethylamine, tributylamine and N,N-diisopropylethylamine, with N,N-diisopropylethylamine being preferred. Exampples of the suitable copper base that can be used in the reaction include cuprous salts such as copper(I) acetate, copper(I) trifluoroacetate, cuprous chloride, cuprous bromide, cuprous iodide and cuprous cyanide, and cupric salts such as cupric chloride and cupric bromide, with cupric chloride and cupric bromide being preferred.

For synthesis of the compound of the general formula (G-I), the compound represented by the general formula (C-IV) is used as an intermediate and this compound, being undocumented and novel, constitutes the present invention. To prepare the compound of the general formula (C-IV), an alcohol represented by the general formula (C-I) (where $R^3$ and $R^4$ have the same meanings as defined above) may be reacted with a compound of the general formula (C-II) or (C-III)

$$R^7SO_2Cl \qquad\qquad\qquad\qquad\qquad\qquad (C\text{-}II)$$

$$(R^7SO_2)_2O \qquad\qquad\qquad\qquad\qquad\qquad (C\text{-}III)$$

(where $R^7$ represents an optionally substituted alkyl group or an optionally substituted aryl group) either after reacting the alcohol with a suitable base in a suitable solvent to be converted to an alkoxide or directly in a suitable solvent in the presence of a suitable base at a temperature between −78° C. and room temperature, preferably between 0° C. and room temperature. In this reaction, a suitable catalyst such as N,N-dimethylaminopyridine may be used. The suitable solvent that can be used in this reaction is an inert solvent that does not affect the reaction, as exemplified by diethyl ether, diisopropyl ether, tert-butyl methyl ether, tetrahydrofuran, dioxane, diglyme, acetone, N,N-dimethylformamide, N,N-dimethylacetamide and dimethyl sulfide, with tetrahydrofuran and tert-butyl methyl ether being preferred. Examples of the suitable base that can be used in the reaction include alkali metal hydrides such as potassium hydride, sodium hydride and lithium hydride, or carbonates such as potassium carbonate and sodium carbonate, bicarbonates such as potassium hydrogencarbonate and sodium hydrogencarbonate, organic strong bases such as 1,8-diazabicyclo(5.4.0)-7-undecene and 1,5-diazabicyclo (4.3.0)-5-nonene, tertiary amines such as triethylamine, tributylamine and N,N-diisopropylethylamine; among these, sodium hydride and triethylamine are preferred.

The compound of the invention which is represented by the general formula (G-VI) may be synthesized by the following procedure:

a compound represented by the general formula (G-I) (where $R^1$, $R^2$, $R^3$ and $R^4$ have the same meanings as defined above) is reacted in an inert solvent such as hexane, toluene, diethyl ether, diisopropyl ether, tert-butyl methyl ether, tetrahydrofuran, dioxane or tert-butanol, preferably in tert-butyl methyl ether, tetrahydrofuran or diethyl ether, at a temperature between −78° C. and the boiling point of the reaction mixture, preferably between −40° C. and room temperature, with an alkali metal such as lithium, sodium or potassium, alkyllithium such as methyllithium, ethyllithium, n-propyllithium, i-propyllithium, n-butyllithium, sec-butyllithium or tert-butyllithium, or a Grignard reagent such as methylmagnesium chloride, methylmagnesium bromide, methylmagnesium iodide, ethylmagnesium chloride, ethylmagnesium bromide, ethylmagnesium iodide, n-propylmagnesium chloride, n-propylmagnesium bromide, n-propylmagnesium iodide, i-propylmagnesium chloride, i-propylmagnesium bromide, i-propylmagnesium iodide, n-butylmagnesium chloride, n-butylmagnesium bromide, n-butylmagnesium iodide, sec-butylmagnesium chloride, sec-butylmagnesium bromide, sec-butylmagnesium iodide, tert-butylmagnesium chloride, tert-butylmagnesium bromide or tert-butylmagnesium iodide, or a reagent selected from among lithium hydride, sodium hydride, potassium hydride, tert-butoxypotassium, lithium amide, sodium amide, potassium amide, lithium diisopropylamide, sodium diisopropylamide, potassium diisopropylamide, sodium bis(trimethylsilyl) amide and potassium bis(trimethylsilyl)amide, preferably reacted with n-butyllithium or tert-butylmagnesium chloride; then, reaction with carbon dioxide follows to give a compound represented by the general formula (G-II) (where $R^1$, $R^2$, $R^3$ and $R^4$ have the same meanings as defined above); subsequently, the compound represented by the general formula (G-VI) (where $R^1$, $R^2$, $R^3$, $R^4$, $R^5$ and $R^6$ have the same meanings as defined above) is obtained by performing amidation reaction on the compound of the general formula (G-II) in the usual manner. Amidation reaction typically involves reaction with a suitable condensing agent and an amine of the general formula (G-III)

$$R^5R^6NH \qquad\qquad\qquad\qquad\qquad\qquad (G\text{-}III)$$

(where $R^5$ and $R^6$ which may be the same or different represent a hydrogen atom or an optionally substituted lower alkyl group) in an inert solvent in the presence or absence of an organic base or an inorganic base (preferably, in their absence).

The condensing agent is a reagent selected from among commonly used condensing agents such as hydrochlorides of dicyclohexylcarbodiimide, diisopropylcarbodiimide and 1-ethyl-3-(3-dimethylaminopropyl)carbodiimide, and methyl chloroformate, ethyl chloroformate and isopropyl chloroformate, with a hydrochloride of 1-ethyl-3-(3-dimethylaminopropyl)carbodiimide and ethyl chloroformate being preferred.

Exemplary organic bases include pyridine and triethylamine. Exemplary inorganic bases include sodium hydroxide, sodium alkoxide, potassium alkoxide, alkyllithium, potassium carbonate., sodium carbonate and potassium hydroxide.

Useful reaction solvents are inert solvents such as toluene, diethyl ether, diisopropyl ether, tert-butyl methyl ether, tetrahydrofuran, dioxane, dichloromethane, dichloroethane, chloroform and ethyl acetate, or mixtures of solvents selected from among these solvents; preferably, tert-butyl methyl ether, ethyl acetate and dichloromethane are used. The reaction temperature is between −78° C. and the boiling point of the reaction mixture, preferably between −40° C. and room temperature.

The compound which is represented by the general formula (G-V) (where $R^1$, $R^2$, $R^3$, $R^4$, $R^5$ and $R^6$ have the same meanings as defined above) can also be obtained by the following procedure:

a compound represented by the general formula (G-I) (where $R^1$, $R^2$, $R^3$ and $R^4$ have the same meanings as defined above) is reacted in an inert solvent such as hexane, toluene, diethyl ether, diisopropyl ether, tert-butyl methyl ether, tetrahydrofuran or dioxane, preferably in tert-butyl methyl ether, tetrahydrofuran or diethyl ether, at a temperature between −78° C. and the boiling point of the reaction mixture, preferably between −40° C. and room temperature, with an alkali metal such as lithium, sodium or potassium, alkyllithium such as methyllithium, ethyllithium, n-propyllithium, i-propyllithium, n-butyllithium, sec-butyllithium or tert-butyllithium, or a Grignard reagent such as methylmagnesium chloride, methylmagnesium bromide, methylmagnesium iodide, ethylmagnesium chloride, ethylmagnesium bromide, ethylmagnesium iodide, n-propylmagnesium chloride, n-propylmagnesium bromide, n-propylmagnesium iodide, i-propylmagnesium chloride, i-propylmagnesium bromide, i-propylmagnesium iodide, n-butylmagnesium chloride, n-butylmagnesium bromide, n-butylmagnesium iodide, sec-butylmagnesium chloride, sec-butylmagnesium bromide, sec-butylmagnesium iodide, tert-butylmagnesium chloride, tert-butylmagnesium bromide or tert-butylmagnesium iodide, or a reagent selected from among lithium hydride, sodium hydride, potassium hydride, tert-butoxypotassium, lithium amide, sodium amide, potassium amide, lithium diisopropylamide, sodium diisopropylamide, potassium diisopropylamide, sodium bis(trimethylsilyl) amide and potassium bis(trimethylsilyl)amide, preferably reacted with n-butyllithium or tert-butylmagnesium chloride; subsequently, reaction is performed with a compound represented by the general formula (G-IVa) (where $R^5$ and $R^6$ which may be the same or different represent a hydrogen atom or an optionally substituted lower alkyl group) or a compound represented by the general formula (G-IVb)

$$R^{6a}NCO \quad\quad\quad (G\text{-}IVb)$$

(where $R^{6a}$ represents an optionally substituted lower alkyl group).

If the resulting compound of the general formula (G-V) is heated in an inert solvent such as a saturated hydrocarbon (e.g. decane, undecane, dodecane, tridecane, tetradecane, cis-decalin or trans,-decalin), an aromatic hydrocarbon (e.g. toluene, xylene, dichlorobenzene, tetralin or biphenyl), an ether-containing hydrocarbon (e.g. diglyme, triglyme, tetraglyme or diphenyl ether), a sulfolane-containing hyrocarbon (e.g. sulfolane) or a mixture thereof, preferably, undecane, dodecane, cis-decalin, trans-decalin, tetralin or a mixture thereof, at 100–300° C., preferably at 160–250° C., there is produced a 4-substituted benzopyran derivative represented by the general formula (G-VI) (where $R^1$, $R^2$, $R^3$, $R^4$, $R^5$ and $R^6$ have the same meanings as defined above). During this thermal cyclization reaction, a benzofuran derivative represented by the general formula (G-VII) forms as a by-product. It was found that the yield ratio between the end product 4-substituted benzopyran derivative and the by-product benzofuran derivative depends largely upon the reaction solvent and the reaction temperature; when diethylaniline, a common conventional solvent for the thermal cyclization reaction, was used as the reaction solvent, benzopyran derivatives were not obtained at all but only benzofuran derivatives occurred.

The compound of the general formula (G-II) can also be obtained in salt form; specific examples of its salt include a lithium salt, a sodium salt, a potassium salt and a magnesium salt, with a sodium salt and a potassium salt being preferred.

If a compound of the general, formula (G-IVb) is used, $R^5$ in the compound of the general formula (G-VI) is a hydrogen atom.

C. Schemes (5) and (6):

For schemes (5) and (6), preferred examples of $R^1$ and $R^2$ which may be the same or different include a hydrogen atom, an optionally substituted lower alkyl group, a halogen atom, an optionally substituted lower alkoxy group, $NY_aY_b$ (where $Y_a$ and $Y_b$ which may be the same or different each represent a hydrogen atom, an optionally substituted lower alkyl group, an optionally substituted lower alkoxycarbonyl group, an acyl group, an optionally substituted lower alkylsulfonyl group or an optionally substituted arylsulfonyl group or, when taken together with the nitrogen atom to which they are bound, may form a 3- to 8-membered ring), a nitro group, a cyano group, an optionally substituted lower alkoxycarbonyl group, an optionally substituted lower alkylsulfonyl group, and an optionally substituted arylsulfonyl group. These groups correspond to $R^{1g}$ and $R^{2g}$ as defined in the general formula (Iz).

Preferably, $R^5$ and $R^6$ which may be the same or different are a hydrogen atom or an optionally substituted lower alkyl group.

In schemes (5) and (6), unless otherwise noted, the following definitions hold:

the lower alkyl group means a straight-chained alkyl group having 1–6 carbon atoms or a branched or cyclic alkyl group having 3–8 carbon atoms; examples include a methyl group, an ethyl group, a n-prbpyl group, a n-butyl group, a n-pentyl group, a n-hexyl group, an i-propyl group, an i-butyl group, a sec-butyl group, a tert-butyl group, an i-pentyl group, a neopentyl group, a tert-pentyl group, an i-hexyl group, a cyclopropyl group, a cyclobutyl group, a cyclopentyl group, a cyclohexyl group, a cycloheptyl group and a cyclooctyl group;

the halogen atom means a fluorine atom, a chlorine atom, a bromine atom or an iodine atom;

the lower alkoxy group means a straight-chained alkoxy group having 1–6 carbon atoms or a branched or cyclic alkoxy group having 3–8 carbon atoms; examples include a methoxy group, an ethoxy group, a n-propoxy group, a n-butoxy group, a n-pentoxy group, a n-hexoxy group, an i-propoxy group, an i-butoxy group, a sec-butoxy group, a tert-butoxy group, an i-pentoxy group, a neopentoxy group, a tert-pentoxy group, an i-hexoxy group, a cyclopropoxy group, a cyclobutoxy group, a cyclopentoxy group, a cyclohexoxy group, a cycloheptoxy group and a cyclooctoxy group.

the lower alkoxycarbonyl group means an alkoxycarbonyl group whose alkyl portion is a straight-chained alkyl group having 1–6 carbon atoms or an alkoxycarbonyl group whose alkyl portion is a branched or cyclic alkyl group having 3–8 carbon atoms, and examples include a methoxycarbonyl group, an ethoxycarbonyl group, a n-propoxycarbonyl group, a n-butoxycarbonyl group, a n-pentoxycarbonyl group, a n-hexoxycarbonyl group, an i-propoxycarbonyl group, an i-butoxycarbonyl group, a sec-butoxycarbonyl group, a tert-butoxycarbonyl group, an i-pentoxycarbonyl group, a neopentoxycarbonyl group, a tert-pentoxycarbonyl group, an i-hexoxycarbonyl group, a cyclopropoxycarbonyl group, a cyclobutoxycarbonyl group, a cyclopentoxycarbonyl group, a cyclohexoxycarbonyl group, a cycloheptoxycarbonyl group and a cyclooctoxycarbonyl group;

the lower alkylsulfonyl group means an alkylsulfonyl group having 1–8 carbon atoms whose alkyl portion is a straight-chained alkyl group or an alkylsulfonyl group having 3–8 carbon atoms whose alkyl portion is a branched or cyclic alkyl group, and examples include a methylsulfonyl group, an ethylsulfonyl group, a propylsulfonyl group, an isopropylsulfonyl group, a butylsulfonyl group and an isobutylsulfonyl group.

the arylsulfonyl group means an aromatic sulfonyl group and examples include a phenylsulfonyl group, a p-tolylsulfonyl group, a p-chlorophenylsulfonyl group, a 2-furylsulfonyl group, a 3-furylsulfonyl group, a 2-thienylsulfonyl group, a 3-thienylsulfonyl group, a 2-pyridylsulfonyl group, a 3-pyridylsulfonyl group and a 4-pyridylsulfonyl group.

$Y_a$ and $Y_b$ in $NY_aY_b$ which may be the same or different each represent a hydrogen atom, an optionally substituted lower alkyl group, an optionally substituted lower alkoxycarbonyl group, an acyl group, an optionally substituted lower alkylsulfonyl group or an optionally substituted arylsulfonyl group or, when taken together with the nitrogen atom to which they are bound, may form a 3- to 8-membered ring. The acyl group as used herein means a formyl group or an alkylcarbonyl group having 1–8 carbon atoms whose alkyl portion is an optionally substituted straight-chained alkyl group, an alkylcarbonyl group having 3–8 carbon atoms whose alkyl portion is an optionally substituted branched or cyclic alkyl group, or an arylcarbonyl group, and examples include a formyl group, an acetyl group, a trifluoroacetyl group, a propionyl group, a butyryl group, a valeryl group, an isobutyryl group, an isovaleryl group, a pivaloyl group, a benzoyl group, a phthaloyl group and a toluoyl group.

If $R^1$, $R^2$, $R^3$ $R^4$, $R^5$, $R^6$, $R^7$ or $R^8$ represents an optionally substituted lower alkyl group, an optionally substituted lower alkoxy group, an optionally substituted lower alkoxycarbonyl group or an optionally substituted lower alkylsulfonyl group, the optionally present substituent may be exemplified by a halogen atom, a phenyl group, a hydroxy group, a nitro group, a cyano group, a cyclic alkyl group having 3–8 carbon atoms, a lower alkoxy group optionally substituted by a halogen atom or a phenyl group, a lower alkoxycarbonyl group, a carboxyl group and $NY_cY_d$; $Y_c$ and $Y_d$ which may be the same or different each represent a hydrogen atom, a lower alkyl group, a lower alkoxycarbonyl group, an acyl group, a lower alkylsulfonyl group or an optionally substituted arylsulfonyl group or, when taken together with the nitrogen atom to which they are bonded, may form a 3- to 8-numbered ring.

In the case where $R^1$, $R^2$, $R^3$, $R^4$, $R^5$, $R^6$, $R^7$ or $R^8$ represents a lower alkyl having a halogen atom as a substituent, an α-haloalkyl group may be mentioned as an example. The α-haloalkyl group means a straight-chained alkyl group having 1–6 carbon atoms or a branched or cyclic alkyl group having 3–8 carbon atoms that have 1–3 halogen atoms in 1-position and which may further possess a substituent, and examples include a fluoromethyl group, a difluoromethyl group, a trifluoromethyl group, a 1-fluoroethyl group, a 1,1-difluoroethyl group, a 1-fluoropropyl group, a 1,1-difluoropropyl group, a 1-fluorocyclopropyl group, a 1-difluorobutyl group, a 1,1-difluorobutyl group, a chloromethyl group, a dichloromethyl group, a trichloromethyl group, a 1-chloroethyl group, a 1,1-dichloroethyl group, a 1-chloropropyl group, a 1,1-chloropropyl group, a 1-chlorocyc lopropyl group, a 1-chlorobutyl group, a 1,1-dichlorobutyl group, a bromomethyl group, a dibromomethyl group, a tribromomethyl group, a 1-bromoethyl group, a 1,1-dibromoethyl group, a 1-bromopropyl group, a 1,1-dibromopropyl group, aa 1-bromocyclopropyl group, a 1-brrmobutyl group, a 1,1-dibromobutyl group, an iodomethyl group, a diodomethyl group, a trurodomethyl group, a 1-modoethyl group, a 1,1-dirodoethyl group, a 1-iodopropyl group, a 1,1-diuodopropyl group, a 1-iodocyclopropyl group, a 1-iodobutyl group and a 1,1-diiodobutyl group.

If $R^1$, $R^2$, $R^5$, $R^6$ or $R^7$ represents an optionally substituted arylsulfonyl group or an optionally substituted aryl group, the optionally present substituent may be exemplified by a halogen atom, a phenyl group, a hydroxy group, a nitro group, a cyano group, a straight-chained alkyl group having 1–6 carbon atoms, a branched or cyclic alkyl group having 3–8 carbon atoms, a lower alkoxy group optionally substituted by a halogen atom or a phenyl group, a lower alkylthio group optionally substituted by a halogen atom or a phenyl group, a lower alkoxycarbonyl group, a carboxyl group and $NY_eY_f$; $Y_e$ and $Y_f$ which may be the same or different each represent a hydrogen atom, an optionally substituted lower alkyl group, an optionally substituted lower alkoxycarbonyl group, an acyl group, an optionally substituted lower alkylsulfonyl group or an arylsulfonyl group or, when taken together, may form a 3- to 8-numbered ring.

Examples of the optionally substituted lower alkyl group as $R^1$ and $R^2$ include a methyl group, a fluoromethyl group, a trifluoromethyl group, a pentafluoroethyl group, a benzyl group, a nitromethyl group, a cyclopropylmethyl group, a methoxymethyl group, an ethoxymethyl group, a benzyloxymethyl group, a methylthiomethyl group, an ethylthiomethyl group, a methoxycarbonylmethyl group, a dimethylaminomethyl group, an ethyl group, a 2-fluoroethyl group, a n-propyl group, an i-propyl group, a 1-methylthiopropyl group and a n-butyl group.

Examples of the optionally substituted lower alkyl group as $R^3$ and $R^4$ include a methyl group, an ethyl group, a n-propyl group, a n-butyl group, a fluoromethyl group, a trifluoromethyl group, a benzyl group, a cyclopropylmethyl group, a 1-fluoroethyl group and a 1,1-difluoroethyl group.

Examples of the optionally substituted lower alkyl group as $R^5$ and $R^6$ include a methyl group, a benzyl group, a cyclopropylmethyl group, an ethyl group, a 2-cyanoethyl group, a 2-fluoroethyl group and a n-propyl group.

Examples of the optionally substituted lower alkoxy group as $R^1$ and $R^2$ include a methoxy group, a trifluoromethoxy group, a benzyloxy group, a cyclopropylmethoxy group, an ethoxy group and a n-propoxy group.

Examples of the optionally substituted lower alkoxycarbonyl group as $R^1$ and $R^2$ include a methoxycarbonyl group, a trifluoromethoxycarbonyl group, a benzyloxycarbonyl group, a cyclopropylmethoxycarbonyl group, an ethoxycarbonyl group, a n-propoxycarbonyl group and a tert-butoxycarbonyl group.

Examples of the above-mentioned $NY_aY_b$, $NY_cY_d$ and $NY_eY_f$ include an amino group, a methylamino group, a benzylamino group, an ethylamiono group, a dimethylamino group, an ethylmethylamino group, a pyrrolidinyl group, a piperidino group, a morpholino group, an acetamido group, a benzamido group, an N-methylacetamido group, a tert-butoxycarbonylamino group, an N-methyl-tert-butoxycarbonylamino group, a methylsulfonylamino group, an ethylsulfonylamino group, a propylsulfonylamino group, an isopropylsulfonylamino group, a butylsulfonylamino group, an isobutylsulfonylamino group, a phenylsulfonylamino group, a p-tolylsulfonylamino group and a p-chlorophenylsulfonylamino group.

When taken together with the nitrogen atom to which they are bound, $Y_a$ and $Y_b$, $Y_c$ and $Y_d$, or $Y_e$ and $Y_f$ may form a 3- to 8-membered ring and the ring has 2–7 carbon atoms, with any carbon atom on the ring being optionally replaced by a nitrogen atom, an oxygen atom or a sulfur atom. Specific examples include an aziridine ring, an azetidine ring, a pyrrole ring, a pyrrolidine ring, a pyridine ring, a 3,4-dihydro-2H-azepine ring, a 3,4,5,6-tetrahydro-2H-azepine ring, an azocine ring, a 5,6-dihydro-azocine ring, a 5,6,7,8-tetrahydroazocine ring, an oxazoline ring, an isoxazoline ring, a thioxazoline ring, a piperazine ring, a morpholine ring and a thiomorpholine ring.

The preferred position of substitution by $R^1$ is in 6-position on the benzopyran ring.

Preferred examples of $R^1$ include an optionally substituted lower alkyl group, an optionally substituted alkylsulfonyl group, an optionally substituted arylsulfonyl group, a nitro group and a cyano group; among these, lower alkyl groups having a fluorine atom as a substituent are preferred, with a 6-trifluoromethyl group and a 6-pentafluoroethyl group being particularly preferred.

The preferred example of $R^2$ is a hydrogen atom.

Speaking of $R^3$ and $R^4$, they are preferably the same; more preferably, they both are an optionally substituted α-haloalkyl group; most preferably, they both are a fluoromethyl group.

Examples of the optionally substituted lower alkyl group as $R^5$ and $R^6$ include a methyl group, a benzyl group, a cyclopropylmethyl group, an ethyl group, a 2-cyanoethyl group, a 2-fluoroethyl group and a n-propyl group.

Speaking of $R^5$ and $R^6$, a preferred case is where $R^5$ is a hydrogen atom and $R^6$ is an optionally substituted lower alkyl group; a more preferred case is where $R^5$ is a hydrogen atom and $R^6$ is a lower alkyl group optionally having a cyano group, and a particularly preferred case is where $R^5$ is a hydrogen atom and $R^6$ is a 2-cyanoethyl group or a 2-cyanomethyl group.

Examples of the optionally substituted alkyl group as $R^7$ include a methyl group, an ethyl group and a propyl group. Examples of the optionally substituted aryl group as $R^7$ include a phenyl group, a p-tolyl group and a p-chlorophenyl group; among these, a p-tolyl group and a methyl group are preferred, with a p-tolyl group being particularly preferred.

Speaking of $R^8$, it represents an optionally substituted lower alkyl group; it is preferably an unsubstituted alkyl group, with a methyl group and an ethyl group being particularly preferred.

The compound of the general formula (I) (where $R^1$, $R^2$, $R^3$, $R^4$ and Hal have the same meanings as defined above) may be synthesized by the following procedure. Stated specifically, the compound can be obtained by heating a compound of the general formula (D-II) (where $R^1$, $R^2$, $R^3$, $R^4$ and Hal have the same meanings as defined above) either with or without a solvent, preferably in a suitable solvent for smooth progress of the reaction, at a temperature between 130° C. and the boiling point of the solvent, preferably at 150–200° C. The suitable solvent to be used in the reaction is an inert high-boiling point solvent that does not affect the reaction and examples are solvent naphtha, xylene, o-xylene, m-xylene, p-xylene, mesitylene, o-chlorotoluene, m-chlorotoluene, p-chlorotoluene, o-dichlorobenzene, dodecane, tetralin, decalin and diphenyl ether, with solvent naphtha and o-xylene being preferred.

A compound of the general formula (G-VI) (where $R^1$, $R^2$, $R^3$, $R^4$, $R^5$ and $R^6$ have the same meanings as defined above) can typically be synthesized by conversion from the compound of the general formula (I) by a method that involves a carbon monoxide inserting cross-coupling reaction as a key reaction that uses a metal as a catalyst. To be specific, the compound of the general formula (I) (where $R^1$, $R^2$, $R^3$, $R^4$ and Hal have the same meanings as defined above) is subjected to a cross-coupling reaction with a compound of the general formula (G-III)

$$HNR^5R^6 \qquad \text{(G-III)}$$

(where $R^5$ and $R^6$ have the same meanings as defined above) in a carbon monoxide stream at atmospheric or subatmospheric pressure from a $CO_2$ gas container, preferably at atmospheric pressure, at a reaction temperature between −78° C. and 150° C., preferably between room temperature and 130° C., for a reaction time of from 1 hour to 3 days, preferably from 3 hours to 1 day, in the presence of a zero-valence or divalent metal catalyst such as palladium, nickel, copper, zinc, tin or magnesium, preferably, 1–5 mol % of zero-valence or divalent palladium such as bis(triphenylphosphine)palladium:acetate, palladium acetate and triphenylphosphine, bis(triphenylphosphine)palladium chloride, [1,1'-bis(diphenylphosphino)ferrocene]palladium chloride dichloromethane adduct, tetrakis(triphenylphosphine)palladium, tris(dibenzylideneacetone)dipalladium chloroform adduct and triphenylphosphine, or tris(dibenzylideneacetone)dipalladium chloroform adduct in a solvent such as N,N-dimethylformamide, tetrahydrofuran, dioxane, ether, acetonitrile, toluene, benzene or water, preferably N,N-dimethylformamide, thereby giving a 4-substituted benzopyran derivative represented by the general formula (G-VI) (where $R^1$, $R^2$, $R^3$, $R^4$, $R^5$ and $R^6$ have the same meanings as defined above).

For synthesis of the compound represented by the general formula (I), the compound represented by the general formula (D-II) is used as an intermediate and this compound, being undocumented and novel, constitutes the present invention. To give the compound of the general formula (D-II), a compound represented by the general formula (C-VI) (where $R^1$, $R^2$, $R^3$ and $R^4$ have the same meanings as defined above) is reacted with a suitable base in a suitable solvent at a temperature between −78° C. and the boiling point of the reaction mixture, preferably between −40° C. and room temperature, and without subsequent isolation, reaction is performed with a halogen (preferably bromine). The suitable solvent to be used in this reaction is an inert solvent that does not affect the reaction and may be exemplified by hexane, toluene, diethyl ether, diisopropyl ether, tert-butyl methyl ether, tetrahydrofuran and dioxane, with tetrahydrofuran and diethyl ether being preferred. The suitable base tobe used in this reaction is exemplified by alkyllithium such as methyllithium, ethyllithium, n-propyllithium, i-propyllithium, n-butyllithium, sec-butyllithium or tert-butyllithium, alkoxides such as potassium t-butoxide, sodium methoxide and sodium ethoxide, or Grignard reagents such as methylmagnesium chloride, methylmagnesium bromide, methylmagnesium iodide, ethylmagnesium chloride, ethylmagnesium bromide, ethylmagnesium iodide, n-propylmagnesium chloride, n-propylmagnesium bromide, n-propylmagnesium iodide, i-propylmagnesium chloride, i-propylmagnesium bromide, i-propylmagnesium iodide, n-butylmagnesium chloride, n-butylmagnesium bromide, n-butylmagnesium iodide, sec-butylmagnesium chloride, sec-butylmagnesium bromide, sec-butylmagnesium iodide, tert-butylmagnesium chloride, tert-butylmagnesium bromide and tert-butylmagnesium iodide; among these, n-butyllithium and ethylmagnesium bromide are preferred.

The compound of the general formula (D-II) can also be obtained by reacting a compound of the general formula (C-VI) (where $R^1$, $R^2$, $R^3$ and $R^4$ have the same meanings as defined above) with a halogen (preferably bromine) in a suitable solvent in the presence of a suitable base at a temperature between −40° C. and room temperature, preferably between 0° C. and room temperature. The suitable solvent to be used in this invention may be selected from among alcohols such as methanol, ethanol, n-propyl alcohol, i-propyl alcohol, n-butyl alcohol, i-butyl alcohol, sec-butyl alcohol and tert-butyl alcohol, mixtures of these alcohols with inert solvents that do not affect the reaction such as diethyl ether, diisopropyl ether, tert-butyl methyl ether, tetrahydrofuran and dioxane; among these, a mixture of tert-butyl methyl ether and tert-butyl alcohol is a preferred solvent system. The suitable base to be used in this reaction is an alkoxide such as potassium tert-butoxide, sodium methoxide or sodium ethoxide, with potassium tert-butoxide being preferred.

For synthesis of the compound represented by the general formula (D-II), the compound represented by the general formula (C-VI) is used as an intermediate and this compound, being undocumented and novel, constituents the present invention. To give the compound of the general formula (C-VI), a sulfonate ester represented by the general formula (C-IV) (where $R^7$, $R^3$ and $R^4$ have the same meanings as defined above) may be reacted with a phenol represented by the general formula (C-V) (where $R^1$ and $R^2$ have the same meanings as definedabove) in an inert solvent such as acetonitrile that does not affect the reaction, in the presence of a suitable base and a catalytic amount of a suitable copper salt at a temperature between −78° C. and room temperature, preferably between 0° C. and room temperature. Examples of the suitable base that can be used in the reaction include organic strong bases such as 1,8-diazabicyclo(5.4.0)-7-undecene and 1,5-diazabicyclo(4.3.0)-5-nonene, and tertiary amines such as triethylamine, tributylamine and N,N-diisopropylethylamine, with N,N-diisopropylethylamine being preferred. Exampples of the suitable copper salt that can be used in the reaction include cuprous salts such as copper(I) acetate, copper(I) trifluoroacetate, cuprous chloride, cuprous bromide, cuprous iodide and cuprous cyanide, and cupric salts such as cupric chloride and cupric bromide, with cupric chloride and cupric bromide being preferred.

For synthesis of the compound of the general formula (C-VI), the compound represented by the general formula (C-IV) is used as an intermediate and this compound, being undocumented and novel, constitutes the present invention. To prepare the compound of the general formula (C-IV), an alcohol represented by the general formula (C-I) (where $R^3$ and $R^4$ have the same meanings as defined above) may be reacted with a compound of the general formula (C-II) or (C-III)

  (C-II)

  (C-III)

(where $R^7$ represents an optionally substituted alkyl group or an optionally substituted aryl group) either after reacting the alcohol with a suitable base in a suitable solvent to be converted to an alkoxide or directly in a suitable solvent in the presence of a suitable base at a temperature between −78° C. and room temperature, preferably between 0° C. and room temperature. In this reaction, a suitable catalyst such as N,N-dimethylaminopyridine may be used. The suitable solvent that can be used in this reaction is an inert solvent that does not affect the reaction, as exemplified by diethyl ether, diisopropyl ether, tert-butyl methyl ether, tetrahydrofuran, dioxane, diglyme, acetone, N,N-dimethylformamide, N,N-dimethylacetamide and dimethyl sulfide, with tetrahydrofuran and tert-butyl methyl ether being preferred. Examples of the suitable base that can be used in the reaction include alkali metal hydrides such as potassium hydride, sodium hydride and lithium hydride, or carbonates such as potassium carbonate and sodium carbonate, bicarbonates such as potassium hydrogencarbonate and sodium hydrogencarbonate, organic strong bases such as 1,8-diazabicyclo(5.4.0)-7-undecene and 1,5-diazabicyclo(4.3.0)-5-nonene, tertiary amines such as triethylamine, tributylamine and N,N-diisopropylethylamine; among these, sodium hydride and triethylamine are preferred.

Among the compounds represented by the general formula (H-V), a compound in which $R^3$ and $R^4$ are a trifluoromethyl group (—$CH_2F$) is an undocumented novel compound and constitutes the present invention. To give the compound of the general formula (H-V), a compound represented by the general formula (H-IV) (where $R^1$, $R^2$, $R^3$, $R^4$ and $R^8$ have the same meanings as defined above) may be rapidly heated to a temperature between 180° C. and 250° C., preferably between 180° C. and 200° C., either with or without a solvent, preferably in a suitable solvent for smooth progress of the reaction, either at atmospheric or superatmospheric pressure. The suitable solvent to be used in this reaction is a high-boiling point solvent that does not affect the reaction and may be exemplified by mesitylene, dichlorobenzene, dodecane, tetralin, decalin and diphenyl ether, with 1,2-dichlorobenzene being preferred.

For synthesis of the compound represented by the general formula (H-V), the compound represented by the general formula (H-IV) is used as an intermediate. Among the compounds represented by the general formula (H-IV), a compound in which $R^3$ and $R^4$ are a trifluoromethyl group (—$CH_2F$) is an undocumented novel compound and constitutes the present invention. To give the compound of the general formula (H-IV), a compound represented by the general formula (C-VI) (where $R^1$, $R^2$, $R^3$ and $R^4$ have the same meanings as defined above) is reacted with a suitable base in a suitable solvent at a temperature between −78° C. and the boiling point of the reaction mixture, preferably between −40° C. and room temperature, and without subsequent isolation, reaction is performed with a compound represented by the general formula (H-II)

  (H-II)

or the general formula (H-III)

  (H-III)

(where $R^8$ represents an optionally substituted lower alkyl group). The suitable solvent to be used in this reaction is an inert solvent that does not affect the reaction and may be exemplified by hexane, toluene, diethyl ether, diisopropyl ether, tert-butyl methyl ether, tetrahydrofuran and dioxane, with tetrahydrofuran and diethyl ether being preferred. The suitable base to be used in this reaction is exemplified by alkyllithium such as methyllithium, ethyllithium, n-propyllithium, i-propyllithium, n-butyllithium, sec-butyllithium or tert-butyllithium, or Grignard reagents such as methylmagnesium chloride, methylmagnesium bromide, methylmagnesium iodide, ethylmagnesium chloride, ethylmagnesium bromide, ethylmagnesium iodide, n-propylmagnesium chloride, n-propylmagnesium bromide, n-propylmagnesium iodide, i-propylmagnesium chloride, i-propylmagnesium bromide, i-propylmagnesium iodide, n-butylmagnesium chloride, n-butylmagnesium bromide, n-butylmagnesium iodide, sec-butylmagnesium chloride, sec-butylmagnesium bromide, sec-butylmagnesium iodide, tert-butylmagnesium chloride, tert-butylmagnesium bromide and tert-butylmagnesium iodide, and alkoxides such as potassium t-butoxide, sodium methoxide and sodium ethoxide; among these, n-butyllithium and ethylmagnesium bromide are preferred.

The compound represented by the general formula (G-VI) can be obtained by conversion from the compound of the general formula (H-V) in the following manner. To be specific, the compound represented by the general formula (H-V) (where $R^1$, $R^2$, $R^3$, $R^4$ and $R^8$ have the same meanings as defined above) is reacted with a suitable reagent in a suitable solvent at a temperature between 0° C. and the boiling point of the solvent, preferably between room temperature and 80° C., to effect hydrolysis (conversion from —$COOR^8$ to —COOH); thereafter, the carboxylate is reacted with a compound represented by the general formula (G-III)

$HNR^5R^6$                      (G-III)

(where $R^5$ and $R^6$ have the same meanings as defined above) and a suitable reagent to effect dehydrative condensation in a suitable solvent at a temperature between 0° C. and the boiling point of the solvent, preferably at room temperature, thereby producing the general formula (G-VI) (where $R^1$, $R^2$, $R^3$, $R^4$, $R^5$ and $R^6$ have the same meanings as defined above).

The suitable solvent for use in hydrolysis is an inert solvent that does not affect the reaction, as exemplified by water, methanol, ethanol, isopropanol, hydrous methanol, hydrous ethanol, hydrous isopropanol, hydrous tetrahydrofuran, hydrous dioxane, benzene and toluene, with ethanol being preferred. The suitable reagent for use in hydrolysis is a base such as lithium hydroxide, sodium hydroxide, potassium hydroxide, barium hydroxide, lithium carbonate, sodium carbonate or potassium carbonate, or an acid such as hydrochloric acid, hydrobromic acid, acetic acid or sulfuric acid, with potassium hydroxide being preferred.

The suitable solvent for use in dehydrative condensation is an inert solvent that does not affect the reaction, as exemplified by tetrahydrofuran, dichloromethane, chloroform, carbon tetrachloride, acetonitrile, benzene, toluene, N,N-dimethylformamide and dimethyl sulfoxide, with tetrahydrofuran being preferred. The suitable reagent for use in dehydrative condensation may be selected from among reagents such as N,N'-carbonyldiimidazole, 1,3-dicyclohexylcarbodiimide, 1-ethyl-3-(3-dimethylaminopropyl)carbodiimide, 2,2'-pyridine sulfide and triphenylphosphine, 2-ethoxy-1-ethoxycarbonyl-1,2-dihydroquinoline, thionyl chloride, phosphorus pentochloride and phosphorus oxychloride; among these, N,N'-carbonyldiimidazole is preferred.

EXAMPLES

The following examples are provided for the purpose of further illustrating the present invention. The term "room temperature" as used hereinafter means a temperature between 10° C. and 30° C.

A. Examples for Schemes (1) and (2):

Example A1

Preparation of 4-Bromo-2,2-bis(fluoromethyl)-6-trifluoromethyl-2-H-1-benzopyran 1) 1-Fluoro-2-fluoromethyl-3-buten-2-ol To a 1 M vinylmagnesium bromide-tetrahydrofuran solution (1 L), 1,3-difluoroacetone (105 g) was added dropwise at −30° C. and the mixture was stirred at the same temperature for 1 hour. To the reaction mixture, a saturated aqueous solution of ammonium chloride was added and following extraction with hexane and washing with a saturated aqueous solution of sodium chloride, the mixture was dried with anhydrous sodium sulfate and concentrated at atmospheric pressure; the resulting residue was purified by distillation to give 1-fluoro-2-fluoromethyl-3-buten-2-ol (105 g) having a boiling point of 78–81° C./106 mm Hg.

1H-NMR (CDCl$_3$) δ: 2.50–2.55(1H, m), 4.26–4.55(4H, m), 5.40(1H, dd, J=10.9, 1.3 Hz), 5.56(1H, dd, J=17.5, 1.3 Hz), 5.91(1H, dd, J=17.5, 10.9 Hz);

2) 4-(2-Chloro-5-trifluoromethylphenyl)-1-fluoro-2-fluoromethyl-3-trans-buten-2-ol A mixture of 3-bromo-4-chlorobenzotrifluoride (1.50 g), 1-fluoro-2-fluoromethyl-3-buten-2-ol (0.80 g), potassium carbonate (2.10 g), tetrabutylammonium bromide (325 mg), palladium acetate (56 mg) and N,N-dimethylacetamide (10 ml) was stirred under a nitrogen atmosphere at 80° C. for 14 hours. To the reaction mixture, 1 N HCl was added followed by extraction with a hexane/ethyl acetate mixed (1/1) solvent; the resulting organic layers were combined and washed with a saturated aqueous solution of sodium thiosulfate and a saturated aqueous solution of sodium chloride; the mixture was dried with anhydrous sodium sulfate and concentrated under reduced pressure; the resulting residue was subjected to silica gel column chromatography (eluent; hexane/ethyl acetate=10/1) to give 4-(2-chloro-5-trifluoromethylphenyl)-1-fluoro-2-fluoromethyl-3-trans-buten-2-ol (1.53 g) having a melting point of 61–62° C.

1H-NMR (CDCl$_3$) δ: 2.76(1H, s), 4.41–4.61(4H, m), 6.31(1H, d, J=16.2 Hz), 7.30(1H, d, J=1.6.2 HZ), 7.42–7.51 (2H, m), 7.75(1H, d, J=1.3 Hz).

3) 3,4-Dibromo-4-(2-chloro-5-trifluoromethylphenyl)-1-fluoro-2-(fluoromethyl)butan-2-ol A mixture of 4-(2-chloro-5-trifluoromethylphenyl)-1-fluoro-2-fluoromethyl-3-trans-buten-2-ol (11.3 g) and tert-amyl alcohol (75 ml) was stirred at −10° C. and, after dropwise addition of bromine (3.88 ml), further stirred at −10° C. for an additional 3 hours. To the reaction mixture, a hexane/ethyl acetate mixed solvent (1/1) was added and the mixture was washed with a saturated aqueous solution of sodium thiosulfate and a saturated aqueous solution of sodium chloride, dried with anhydrous sodium sulfate and concentrated under reduced pressure to give 3,4-dibromo-4-(2-chloro-5-trifluoromethylphenyl)-1-fluoro-2-(fluoromethyl)butan-2-ol (17.3 g).

1H-NMR (CDCl$_3$) δ: 2.70–3.20(1H, m) 4.57–5.10(5H, m), 5.90–6.20(1H, m), 7.50–7.60(2H, m), 7.80–8.20(1H, m).

4) 3-(2-Chloro-5-trifluoromethylphenyl)bromomethyl-2,2-bis(fluoromethyl)oxirane

A mixture of 3,4-dibromo-4-(2-chloro-5-trifluoromethylphenyl)-1-fluoro-2-(fluoromethyl)butan-2-ol (0.46 g), sodium hydride (48 mg) and toluene (10 ml) was stirred at 60° C. for 30 minutes. To the reaction mixture, 2 N HCl was added; after extraction with a hexane/ethyl acetate mixed solvent (5/1), the mixture was washed with a saturated aqueous solution of sodium chloride, dried with anhydrous sodium sulfate and concentrated under reduced pressure; the resulting residue was subjected to silica gel column chromatography to give 3-(2-chloro-5-trifluoromethylphenyl)bromomethyl-2,2-bis(fluoromethyl) oxirane (0.37 g) having a melting point of 54–55° C.

1H-NMR (CDCl$_3$) δ: 3.96(1H, dd, J=9.2, 2.3 Hz), 4.38–4.76(4H, m), 5.29(1H, d, J=9.2 Hz), 7.56–7.57(2H, m), 7.83(1H, s).

5) 4-Bromo-2,2-bis(fluoromethyl)-6-trifluoromethyl-2H-1-benzopyran

A mixture of 3-(2-chloro-5-trifluoromethylphenyl) bromomethyl-2,2-bis(fluoromethyl)oxirane (9.59 g) and tetrahydrofuran (80 ml) was stirred at −10° C. and, following dropwise addition of 0.5 M potassium bis(trimethylsilyl) amide in toluene (50 ml), further stirred at −10° C. for an additional 1.5 hours. To the reaction mixture, 2 N HCl was added, followed by extraction with a hexane/ethyl acetate mixed solvent (1/1); the resulting organic layers were combined, washed with a saturated aqueous solution of sodium chloride, dried with anhydrous sodium sulfate and concentrated under reduced pressure; the resulting residue was purified by distillation to give 4-bromo-2,2-bis (fluoromethyl)-6-trifluoromethyl-2H-1-benzopyran (6.0 g) having a boiling point of 122–123° C./5 mmHg.

1H-NMR (CDCl$_3$) δ: 4.41–4.71(4H, m), 6.14(1H, s), 6.95(1H, d, J=8.6 Hz), 7.50(1H, dd, J=8.6, 2.0 Hz), 7.71(1H, d, J=2.0 Hz).

Example A2

Preparation of 4-Bromo-2,2-bis(fluoromethyl)-6-trifluoromethyl-2H-1-benzopyran via 2,2-Bisfluoromethyl-6-trifluoromethyl-2H-1-benzopyran (alternative method for preparing the end compound of Example A1)

1) 4-(2-Chloro-5-trifluoromethylphenyl)-1-fluoro-2-fluoromethyl-3-butyn-2-ol

A mixture of 4-chloro-3-iodobenzotrifluoride (63.3 g), 1-fluoro-2-fluoromethyl-3-butyn-2-ol (28.8 g), triethylamine (26.2 g), cuprous iodide (0.38 g), bis (triphenylphosphine)palladium chloride (1.40 g) and N,N-dimethylformamide (100 ml) was stirred under a nitrogen atmosphere under heating at 80° C. for 1.5 hours. To the reaction mixture, 2 N HCl and a hexane/ethyl acetate mixed solvent (3/1) were added and the insoluble matter was filtered off with Celite; following extraction with a hexane/ethyl acetate mixed solvent (3/1), the resulting organic layers were combined, washed with a saturated aqueous solution of sodium chloride, dried with anhydrous sodium sulfate and concentrated under reduced pressure; the resulting residue was purified by distillation to give 4-(2-chloro-5-trifluoromethylphenyl)-1-fluoro-2-fluoromethyl-3-butyn-2-ol (44.5 g) having a boiling point of 105–107° C./1 mmHg.

1H-NMR (CDCl$_3$) δ: 2.70–3.00(1H, m), 4.52–4.74(4H, m), 7.54–7.56(2H, m), 7.76(1H, t, J=0.7 Hz)

2) 4-(2-Chloro-5-trifluoromethylphenyl)-1-fluoro-2-fluoromethyl-3-cis-buten-2-ol A mixture of 4-(2-chloro-5-trifluoromethylphenyl)-1-fluoro-2-fluoromethyl-3-butyn-2-ol (44.5 g), 5% palladium-barium carbonate (6.6 g), pyridine (2.3 g) and ethyl acetate (500 ml) was stirred under a hydrogen atmosphere at room temperature for 10 days. The catalyst was filtered off from the reaction mixture; subsequent concentrating under reduced pressure gave 4-(2-chloro-5-trifluoromethylphenyl)-1-fluoro-2-fluoromethyl-3-cis-buten-2-ol (44.0 g).

1H-NMR (CDCl$_3$) δ: 2.00–2.20(1H, m), 4.24–4.52(4H, m), 5.83(1H, dt, J=12.5, 1.3 Hz), 6.74(1H, d, J=12.5 Hz), 7.48(1H, d, J=1 Hz), 7.70(1H, s).

3) 2,2-bis(fluoromethyl)-6-trifluoromethyl-2H-1-benzopyran

A mixture of 4-(2-chloro-5-trifluoromethylphenyl)-1-fluoro-2-fluoromethyl-3-cis-buten-2-ol (8.80 g), potassium tert-butoxide (3.50 g) and N,N-dimethylformamide (60 ml) was stirred at 60° C. for 40 minutes. To the reaction mixture, 2 N HCl was added, followed by extraction with ethyl acetate; the resulting organic layers were combined, washed with a saturated aqueous solution of sodium bicarbonate and a saturated aqueous solution of sodium chloride, dried with anhydrous sodium sulfate and concentrated under reduced pressure to give 2,2-bis(fluoromethyl)-6-trifluoromethyl-2H-1-benzopyran (7.0 g).

1H-NMR (CDCl$_3$) δ: 4.38–4.72(4H, m), 5.72(1H, d, J=9.9 Hz), 6.65(1H, d, J=9.9 Hz), 6.94(1H, d, J=8.6 Hz), 7.27–7.28(2H, m), 7.42(1H, dd, J=8.6, 2.0 Hz).

4) 3,4-Dibromo-2,2-bis(fluoromethyl)-6-trifluoromethyl-3, 4-dihydro-2H-1-benzopyran A mixture of 2,2-bis(fluoromethyl)-6-trifluoromethyl-2H-1-benzopyran (6.68 g), bromine (2 ml) and 3chloroform (150 ml) was stirred at −10° C. for 20 minutes. The reaction mixture was concentrated under reduced pressure to give 3,4-dibromo-2,2-bis(fluoromethyl)-6-trifluoromethyl-3,4-dihydro-2H-1-benzopyran (10.72 g).

1H-NMR (CDCl$_3$) δ: 4.62–5.25(5H, m), 5.66(1H, d, J=4.6 Hz), 7.07(1H, d, J=8.6 Hz), 7.53(1H, dd, J=8.6, 1.6 Hz), 7.73(1H, d, J=1.6 Hz).

5) 4-Bromo-2,2-bis(fluoromethyl)-6-trifluoromethyl-2H-1-benzopyran

A mixture of 3,4-dibromo-2,2-bis(fluoromethyl)-6-trifluoromethyl-3,4-dihydro-2H-1-benzopyran (10.72 g), a 2 N aqueous solution of sodium hydroxide (60 ml) and dioxane (100 ml) was stirred at room temperature for 2 hours. To the reaction mixture, 2 N HCl was added, followed by extraction with ethyl acetate; the resulting orgnaic layers were combined, washed with a saturated aqueous solution of sodium chloride, dried with anhydrous sodium sulfate and concentrated under reduced pressure; the resulting residue was subjected to silica gel column chromatography (eluent; hexane/ethyl acetate=10/1) to give 4-bromo-2,2-bis (fluoromethyl)-6-trifluoromethyl-2H-1-benzopyran (8.18 g).

1H-NMR (CDCl$_3$) δ: 4.41–4.71(4H, m), 6.14(1H, s), 6.95(1H, d, J=8.6 Hz), 7.50(1H, dd, J=8.6, 2.0 Hz), 7.71(1H, d, J=2.0 Hz).

Example A3

Preparation of N-(2-Cyanoethyl)-2,2-bis (fluoromethyl)-6-trifluoromethyl-2H-1-benzopyran-4-carboxamide A mixture of 4-bromo-2,2-bis(fluoromethyl)-6-trifluoromethyl-2H-1-benzopyran (1.73 g), 2-cyanoethylamine (1.44 g), potassium iodide (0.86 g), triphenylphosphine (26 mg), palladium acetate (11 mg) and N,N-dimethylacetamide (10 ml) was stirred under a CO atmosphere at 100° C. for 3 hours. To the reaction mixture, 2 N HCl was added and the precipitating crystals were recovered by filtration. To the recovered crystals, ethyl acetate was added and the insoluble matter was filtered off; the filtrate was washed with a saturated aqueous solution of sodium thiosulfate and a saturated aqueous solution of sodium chloride, dried with anhydrous sodium sulfate and concentrated under reduced pressure; the resulting residue was recrystallized with an ethanol/water mixed solvent, thereby giving N-(2-cyanoethyl)-2,2-bis(fluoromethyl)-6-trifluoromethyl-2H-1-benzopyran-4-carboxamide (1.46 g) having a melting point of 129–131° C.

1H-NMR (DMSO-$d_6$) δ: 2.77(2H, t, J=6.3 Hz), 3.47(2H, q, J=6.3 Hz), 4.53–4.82(4H, m), 6.14(1H, s), 7.11(1H, d, J=8.6 Hz), 7.59(1H, dd, J=8.6,2.0 Hz), 7.83(1H, d, J=2.0 Hz), 8.85–9.00(1H, m). MSm/z:360($M^+$).

Example A4

Preparation of N-(2-Cyanoethyl)-2,2-bis (fluoromethyl)-6-trifluoromethyl-2H-1-benzopyran-4-carboxamide via 2,2-Bis(fluoromethyl)-6-trifluoromethyl-2H-1-benzopyran-4-carboxylic Acid (alternative method for preparing the end compound of Example A3)

1) 2,2-Bis(fluoromethyl)-6-trifluoromethyl-2H-1-benzopyran-4-carboxylic Acid

A mixture of 4-bromo-2,2-bis(fluoromethyl)-6-trifluoromethyl-2H-1-benzopyran (1.72 g), potassium acetate (2.00 g), potassium iodide (0.85 g), triphenylphosphine (27 mg), palladium acetate (11 mg) and N,N-dimethylacetamide (10 ml) was stirred under a CO atmosphere at 120° C. for 9 hours. To the reaction mixture, 2 N HCl was added and the precipitating crystals were recovered by filtration. To the recovered crystals, ethyl acetate was added and the insoluble matter was filtered off; the filtrate was washed with a saturated aqueous solution of sodium thiosulfate and a saturated aqueous solution of sodium chloride, dried with anhydrous sodium sulfate and concentrated under reduced pressure; the resulting residue was dissolved in a saturated aqueous solution of sodium hydrogencarbonate and washed with dichloromethane; to the resulting aqueous layer, concentrated HCl was added to render it acidic and the precipitating crystals were recovered by filtration. The recovered crystals were dissolved in ethyl acetate, dried with anhydrous magnesium sulfate and concentrated under reduced pressure; the resulting residue was recrystallized with an ethyl acetate/hexane mixed solvent to give 2,2-bis(fluoromethyl)-6-trifluoromethyl-2H-1-benzopyran-4-carboxylic acid (1.25 g) having a melting point of 162–163° C.

1H-NMR (DMSO-$d_6$) δ: 4.56–4.85(4H, m), 6.81(1H, s), 7.08(1H, d, J=8.6 Hz), 7.60(1H, dd, J=8.6, 2.0 Hz), 7.83(1H, d, J=2.0 Hz), 8.86(1H, d, J=2.0 Hz), 13.45–13.70(1H, m). MSm/z:308($M^+$).

2) N-(2-Cyanoethyl)-2,2-bis(fluoromethyl)-6-trifluoromethyl-2H-1-benzopyran-4-carboxamide A mixture of 2,2-bis(fluoromethyl)-6-trifluoromethyl-2H-1-benzopyran-4-carboxylic acid (1.55 g), thionyl chloride (0.51 ml) and toluene (5 ml) was stirred at 80° C. for 5 hours. The reaction mixture was concentrated under reduced pressure; to the resulting residue, a mixture of 2-cyanoethylamine (0.42 g) and acetonitrile (5 ml) was added over an ice bath; further, a mixture of triethylamine (2.52 g) and acetonitrile (5 ml) was added and the resulting mixture was stirred first over an ice bath for 10 minutes, then at room temperature for 1 hour. To the reaction mixture, 2 N HCl was added and the precipitating crystals were recovered by filtration. The recovered crystals were dissolved in ethyl acetate, washed with a saturated aqueous solution of sodium chloride, dried with anhydrous sodium sulfate and concentrated under reduced pressure; the resulting residue was recrystallized with an ethanol/water mixed solvent to give N-(2-cyanoethyl)-2,2-bis(fluoromethyl)-6-trifluoromethyl-2H-1-benzopyran-4-carboxamide (1.61 g) having a melting point of 129–131° C.

1H-NMR (DMSO-$d_6$) δ: 2.77(2H, t, J=6.3 Hz), 3.47(2H, q, J=6.3 Hz), 4.53–4.82(4H, m), 6.14(1H, s), 7.11(1H, d, J=8.6 Hz), 7.59(1H, dd, J=8.6, 2.0 Hz), 7.83(1H, d, J=2.0 Hz), 8.85–9.00(1H, m). MSm/z:360($M^+$).

Example A5

N-(2-Cyanoethyl)-6-pentafluoroethyl-2,2-bis (fluoromethyl)-2H-1-benzopyran-4-carboxamide A mixture of 4-bromo-6-pentafluoroethyl-2,2-bis (fluoromethyl)-2H-1-benzopyran (0.40 g), bis (triphenylphosphine)palladium chloride (28 mg), 2-cyanoethylamine (0.28 g), potassium iodide (0.17 g) and N,N-dimethylformamide (5 ml) was stirred under a CO atmosphere at 80° C. for 2 hours. To the reaction mixture, 2N HCl was added, followed by extraction with ethyl acetate; the extract was dried with sodium sulfate and subjected to silica gel column chromatography (eluent; hexane/ethyl acetate=1/1) to give the titled compound (0.33 g) having a melting point of 144–145° C.

1H-NMR (CDCl$_3$) δ: 2.73(2H, t, J=6.3 Hz:), 3.67(2H, q, J=6.3 Hz), 4.44–4.73(4H, m), 6.08(1H, s), 6.40–6.60(1H, m), 7.03(1H, d, J=8.6 Hz), 7.47(1H, dd, J=8.6, 2.0 Hz), 7.81(1H, d, J=2.0 Hz). MSm/z:410($M^+$).

B. Examples for Schemes (3) and (4):

Example B1

Preparation of 1-Fluoro-2-fluoromethyl-3-butyn-2-yl p-Toluenesulfonate

An amount (6.6 g) of 1-fluoro-2-fluoromethyl-3-butyn-2-ol and p-toluenesulfonyl chloride (9.5 g) were dissolved in tetrahydrofuran (100 ml); to the solution under cooling with ice, 60% oily sodium hydride (2.4 g) was added under a nitrogen atmosphere. After the end of the addition, the mixture was stirred for 5 hours while its temperature was raised to room temperature. To the reaction mixture, water was added followed by extraction with ether. The extract was washed with water and a saturated aqueous solution of sodium chloride, dried with anhydrous sodium sulfate and concentrated under reduced pressure. The resulting residue was subjected to silica gel column chromatography (eluent; hexane/methylene chloride=1/1) to give the titled compound (11.1 g).

1H-NMR (CDCl$_3$) δ: 2.45(3H, s), 2.74(1H, s), 4.53–4.87 (4H, m), 7.34(2H, d, J=8.3 Hz), 7.83(2H, d, J=8.3 Hz).

Example B2

Preparation of 1-Fluoro-2-fluoromethyl-3-butyn-2-yl Methanesulfonate (A) An amount (1.2 g) of 1-fluoro-2-fluoromethyl-3-butyn-2-ol was dissolved in tetrahydrofuran (10 ml); to the solution under cooling with ice, 60% oily sodium hydride (0.48 g) was added under a nitrogen atmosphere. The solution was stirred for 30 minutes under cooling with ice and then methanesulfonyl chloride (1.1 ml) was added dropwise. The solution was stirred for 2.5 hours while its temperature was raised to room temperature. To the reaction mixture, etcher was added, followed by extraction with diethyl ether. The extract was washed with water and a saturated aqueous solution of sodium chloride, and dried with anhydrous sodium sulfate and concentrated under reduced pressure. The resulting residue was subjected to silica gel column chromatography (eluent; 30% ethyl acetate/hexane) to give the titled compound (1.6 g).

1H-NMR (CDCl$_3$) δ: 2.98(1H, s), 3.22(3H, s), 4.57–4.89 (4H, m).

(B) An amount (1.2 g) of 1-fluoro-2-fluoromethyl-3-butyn-2-ol and methanesulfonyl chloride (0.85 ml) were dissolved in tert-butyl methyl ether (15 ml); to the solution under cooling with ice, triethylamine (1.5 ml) was added dropwise in a nitrogen atmosphere. After the end of the dropwise addition, the solution was stirred for 1.5 hours under cooling with ice. To the reaction mixture, tert-butyl methyl ether was added, followed by washing with water and a saturated aqueous solution of sodium chloride. The mixture was dried with anhydrous sodium sulfate and concentrated under reduced pressure to give the titled compound (1.9 g).

1H-NMR (CDCl$_3$) δ: 2.98(1H, s), 3.22(3H, s), 4.57–4.89 (4H, m).

Example B3

Preparation of 1-Fluoro-2-fluoromethyl-3-butyn-2-yl 4-Trifluoromethylphenyl Ether (A) An amount (18.6 g) of 1-fluoro-2-fluoromethyl-3-butyn-2-yl methanesulfonate and 4-hydroxybenztrifluoride (19.8 g) were dissolved in acetonitrile (200 ml). To the solution under cooling with ice, cupric chloride dihydrate (3 mg) was added under a nitrogen atmosphere and then diisopropylethylamine (12.3 g) as dissolved in acetonitrile (100 ml) was added dropwise. After the end of the dropwise addition, the solution was stirred overnight while its temperature was raised to room temperature. The acetonitrile was distilled off under reduced pressure and, after addition of hexane, the residue was washed with water, an aqueous solution of sodium hydroxide, dilute hydrochloric acid, aqueous sodium bicarbonate and a saturated aqueous solution of sodium chloride. The residue was dried with anhydrous sodium sulfate and concentrated under reduced pressure. The resulting residue was distilled under reduced pressure to give the titled compound (13.9 g).

1H-NMR (CDCl$_3$) δ: 2.77(1H, s), 4.52–4.80(4H, m), 7.32(2H, d, J=8.6 Hz), 7.59(2H, d, J=8.6 Hz).

(B) An amount (24.8 g) of 1-fluoro-2-fluoromethyl-3-butyn-1-yl p-toluenesulfonate and 4-hydroxybenztrifluoride (16.2 g) were dissolved in acetonitrile (400 ml). To the solution under cooling with ice, cupric chloride dihydrate (5 mg) was added in a nitrogen atmosphere and then diisopropylethylamine (11.7 g) as dissolved in acetonitrile (100 ml) was added dropwise. After the end of the dropwise addition, the mixture was stirred for 6 hours while its temperature was raised to room temperature. The acetonitrile was distilled off under reduced pressure and, following the addition of hexane, the residue was washed with water, an aqueous solution of sodium hydroxide, dilute hydrochloric acid, aqueous bicarbonate and a saturated aqueous solution of sodium chloride. The residue was dried with anhydrous sodium sulfate and concentrated under reduced pressure; the resulting residue was distilled under reduced pressure to give the titled compound (11.9 g).

Example B4

Preparation of 5-Fluoro-4-fluoromethyl-4-(4-trifluoromethylphenoxy)-2-pentynoic Acid A portion (1.32 g) of the 1-fluoro-2-fluoromethyl-3-butyn-2-yl 4-trifluoromethylphenyl ether obtained in Example B3 was dissolved in t-butyl methyl ether (20 ml); to the solution, 1.63 M n-butyllithium (2.913 ml) was added at –70° C. under a nitrogen atmosphere and the mixture was stirred for 15 minutes. Subsequently, carbon dioxide gas was bubbled into the reaction mixture for 10 minutes, followed by addition of 0.1 N HCl and extraction with ethyl acetate; the resulting organic layer was washed with a saturated aqueous solution of sodium chloride, dried with anhydrous sodium sulfate and concentrated under reduced pressure to give the titled compound (1.45 g) as a colorless oil.

1H-NMR (CDCl$_3$) δ: 4.70(4H, dddd, J=47.2, 13.2, 9.9, 2.0 Hz), 7.31(2H, d, J=8.6 Hz), 7.63(2H, d, J=8.6 Hz), 9.20(1H, br s).

Example B5

Preparation of N-(2-Cyanoethyl)-5-fluoro-4-fluoromethyl-4-(4-trifluoromethylphenoxy)-2-pentynamide (A) An amount (1.1 g) of 5-fluoro-4-fluoromethyl-4-(4-trifluoromethylphenoxy)-2-pentynoic acid and triethylamine (903 mg) were dissolved in dichloromethane (20 ml); to the solution under stirring at –10° C., ethyl chloroformate (464 mg) was added dropwise and the mixture was stirred at –10° C. for another one hour. Subsequently, 3-aminopropionitrile (500 mg) was added to the reaction mixture, followed by stirring at room temperature for 2 hours. To the reaction mixture, a hexane/ethyl acetate mixed solvent (1/1) was added and the resulting mixture was washed with 0.1 N HCl, a saturated aqueous solution of sodium hydrogencarbonate and a saturated aqueous solution of sodium chloride, dried with anhydrous sodium sulfate and concentrated under reduced pressure; the resulting residue was subjected to silica gel column chromatography (eluent; hexane/ethyl acetate=3/2) to give the titled compound (1.2 g) as a colorless oil.

1H-NMR (CDCl$_3$) δ: 2.64(2H, t, J=6.3 Hz), 3.55(2H, dt, J=6.3, 5.9 Hz), 4.68(4H, dddd, J=46.2, 15.8, 9.9, 2.0 Hz), 6.42(1H, br s), 7.31(2H, d, J=8.6 Hz), 7.63(2H, d, J=8.6 Hz).

(B) An amount (61 mg) of 1-fluoro-2-fluoromethyl-3-butyn-2-yl 4-trifluoromethylphenyl ether was dissolved in t-butyl methyl ether (2 ml); to the solution, 1.69 M n-butyllithium (0.148 ml) was added at −70° C. under a nitrogen atmosphere and the mixture was stirred for 10 minutes. To the reaction mixture, 2-cyanoethyl isocyanate (28 mg) was added and the resulting mixture was stirred at −70° C. for 10 minutes. To the reaction mixture, a saturated aqueous solution of ammonium chloride was added, followed by extraction with hexane/ethyl acetate (1/1); the resulting organic layers were washed with a 1 N aqueous solution of sodium hydroxide and a saturated aqueous solution of sodium chloride, dried with anhydrous sulfate and concentrated under reduced pressure; the resulting residue was subjected to silica gel column chromatography (eluent; hexane/ethyl acetate=3/2) to give the titled compound (45 mg) as a colorless oil.

Example B6

Preparation of 2,2-Bis(fluoromethyl)-N-(2-cyanoethyl)-6-trifluoromethyl-2H-1-benzopyran-4-carboxamide To undecane (0.8 ml) being heated under reflux, N-(2-cyanoethyl)-5-fluoro-4-fluoromethyl-4-(4-trifluoromethylphenoxy)-2-pentynamide (60 mg) was added and the mixture was heated under reflux for 1 hour. After concentrating under reduced pressure, the resulting residue was subjected to silica gel column chromatography (eluent; dichloromethane/ethyl acetate=10/1) to give the titled compound (54 mg), which was identical to the authentic sample.

Comparative Example

Preparation of N-(2-Cyanoethyl)-2-(1-(fluoromethyl)ethenyl)-5-trifluoromethylbenzofuran-3-carboxamide Reaction was performed as in Example B6, except that the reaction solvent undecane was replaced by diethylaniline. Only the titled compound was obtained quantitatively.

1H-NMR (CDCl$_3$) δ: 2.78(2H, t, J=6.3 Hz), 3.75(2H, dt, J=6.3, 6.3 Hz), 5.33(2H, d, J=46.5 Hz), 5.91(1H, d, J=3.6 Hz), 6.20(1H, s), 6.53(1H, br s), 7.57(1H, d, J=8.6 Hz), 7.64(1H, dd, J=8.6, 1.6 Hz), 8.13(1H, br s).

Example B7

Reaction was performed as in Example B6 using various reaction solvents. The solvents used, their boiling points and the resulting yield ratios are listed in the following table, in which A stands for 2,2-bis(fluoromethyl)-N-(2-cyanoethyl)-6-trifluoromethyl-2H-1-benzopyran-4-carboxamide and B stands for N-(2-cyanoethyl)-2-(1-fluoromethylethenyl)-5-trifluoromethylbenzofuran-3-carboxamide.

TABLE 1

| Solvent | Boiling point | Yield ratio (A:B) |
|---|---|---|
| Tetraglyme | 275° | 6:1 |
| Diphenyl ether | 260° | 7:1 |
| N-methylpyrrolidone | 209° | 1:20 |
| Tetralin | 207° | 7:1 |

TABLE 1-continued

| Solvent | Boiling point | Yield ratio (A:B) |
|---|---|---|
| No solvent | 200° | B alone |
| Dodecane | 216° | 14:1 |
| Undecane | 196° | 14:1 |
| Decane | 174° | 6:1 |
| Perfluorofluorene | 210° | 2.5:1 |
| Perfluorofluorene + undecane | 196° | 4:1 |

Note:
The numeral (200°) in the column of "Boiling Points" given for "No solvent" represents the heating temperature.

Example B8

Preparation of 5-Fluoro-4-fluoromethyl-4-(4-trifluoromethylphenoxy)-N-propyl-2-pentynamide An amount (264 mg) of 1-fluoro-2-fluoromethyl-3-butyn-2-yl 4-trfluoromethyl phenyl ether was dissolved in diethyl ether (2 ml); to the solution, 1.68 M n-butyllithium (0.71 ml) was added at 0° C. under a nitrogen atmosphere and the mixture was stirred for 1 hour. To the reaction mixture, propyl isocyanate (85 mg) was added at 0° C. and the mixture was stirred at room temperature for 5 hours. The reaction mixture was diluted with diethyl ether, washed with a saturated aqueous solution of sodium chloride, dried with anhydrous sodium sulfate and concentrated under reduced pressure; the resulting residue was subjected to silica gel column chromatography (eluent; dichloromethane/methanol=100/3) to give the titled compound (320 mg) as a colorless oil.

1H-NMR (CDCl$_3$) δ: 0.93(3H, t, J=7.3 Hz), 1.47–1.61 (2H, m), 3.25(2H, dt J=7.3, 6.6 Hz), 4.54–4.8.1(4H, m), 5.79(1H, br s), 7.31(2H, d, J=8.6 Hz), 7.61(2H, d, J=8.6 Hz).

Example B9

Preparation of 2,2-Bis(fluoromethyl)-6-trifluoromethyl-N-propyl-2H-1-benzopyran-4-carboxamide An amount (50 mg) of 5-fluoro-4-fluoromethyl-4-(4-trifluoromethylphenoxy)-N-propyl-2-pentynamide was dissolved in o-dichlorobenzene (5 ml) and the solution was heated under reflux for 3.5 hours. The reaction mixture was concentrated under reduced pressure and the resulting residue was subjected to silica gel column chromatography (eluent; hexane/ethyl acetate=3/1) to give the titled compound (31 mg).

1H-NMR (CDCl$_3$) δ: 0.99(3H, t, J=7.3 Hz), 1.56–1.70 (2H, m), 3.37(2H, dt J=6.9, 6.6 Hz), 4.44–4.73(4H, m), 5.98(2H, br s), 6.99(1H, d, J=8.6 Hz), 7.48(1H, dd, J=8.6, 2.0 Hz), 7.83(1H, d, J=2.0 Hz).

C. Examples for Schemes (5) and (6):

Example C1

1-Fluoro-2-fluoromethyl-3-butyn-2-yl p-Toluenesulfonate

An amount (6.6 g) of 1-fluoro-2-fluoromethyl- 3-butyn-2-ol and p-toluenesulfonyl chloride (9.5 g) were dissolved in tetrahydrofuran (100 ml); to the solution under cooling with ice, 60% oily sodium hydride (2.4 g) was added under a nitrogen atmosphere. After the end of the addition, the mixture was stirred for 5. hours while its temperature was raised to room temperature. Water was added to the reaction mixture, followed by extraction with ether. The extract was washed with water and a saturated aqueous solution of sodium chloride, dried with anhydrous sodium sulfate and concentrated under reduced pressure. The resulting residue was subjected to silica gel column chromatography (eluent; hexane/methylene chloride=1/1) to give the titled compound (11.1 g).

1H-NMR (CDCl$_3$) δ: 2.45(3H, s), 2.74(1H, s), 4.53–4.87 (4H, m), 7.34(2H, d, J=8.3 Hz), 7.83(2H, d, J=8.3 Hz).

Example C2

1-Fluoro-2-fluoromethyl-3-butyn-2-yl Methanesulfonate

An amount (1.2 g) of 1-fluoro-2-fluoromethyl-3-butyn-2-ol and methanesulfonyl chloride (0.85 ml) were dissolved in tert-butyl methyl ether (15 ml); to the solution under cooling with ice, triethylamine (1.5 ml) was added dropwise in a nitrogen atmosphere. After stirring for 1.5 hours under cooling with ice, tert-butyl methyl ether was added to the reaction mixture, which was then washed with water and a saturated aqueous solution of sodium chloride. The mixture was dried with anhydrous sodium sulfate and concentrated under reduced pressure to give the titled compound (1.9 g).

1H-NMR (CDCl$_3$) δ: 2.98(1H, s), 3.22(3H, s), 4.57–4.89 (4H, m).

Example C3

1-Fluoro-2-fluoromethyl-3-butyn-2-yl Propanesulfonate

An amount (2.4 g) of 1-fluoro-2-fluoromethyl-3-butyn-2-ol was dissolved in tetrahydrofuran (20 ml); to the solution under cooling with ice, 60% oily sodium hydride (0.96 g) was added under a nitrogen atmosphere. After stirring for 30 minutes under cooling with ice, propanesulfonyl chloride (2.2 ml) was added dropwise. The mixture was stirred for 5 hours while its temperature was raised to room temperature. Water was added to the reaction mixture, followed by extraction with ether. The extract was washed with water and a saturated aqueous solution of sodium chloride, dried with anhydrous sodium sulfate and concentrated under reduced pressure. The resulting residue was subjected to silica gel column chromatography (eluent; 30% ethyl acetate/hexane) to give the titled compound (4.1 g).

1H-NMR (CDCl$_3$) δ: 1.09(3H, t, J=7.3 Hz), 1.87–2.02 (2H, m), 3.25–3.31(2H, m), 4.56–4.88(4H, m).

Example C4

1-Fluoro-2-fluoromethyl-3-butyn-2-yl p-Chlorobenzenesulfonate

An amount (1.2 g) of 1-fluoro-2-fluoromethyl-3-butyn-2-ol and p-chlorobenzenesulfonyl chloride (2.1 g) were dissolved in tetrahydrofuran (10 ml); to the solution under cooling with ice, 60% oily sodium hydride (0.48 g) was added under a nitrogen atmosphere. After the end of the addition, the mixture was stirred for 4 hours while its temperature was raised to room temperature. A hexane/ethane mixed solvent (1/1) was added to the reaction mixture, which was then washed with water and a saturated aqueous solution of sodium chloride, dried with anhydrous sodium sulfate and concentrated under reduced pressure. The resulting residue was subjected to silica gel column chromatography (eluent; hexane/methylene chloride=1/1) and then recrystallized from methylene chloride/hexane to give the titled compound (2.2 g).

1H-NMR (CDCl$_3$) δ: 2.77(1H, s), 4.54–4.88(4H, m), 7.53(2H, d, J=8.6 Hz), 7.89(2H, d, J=8.6 Hz).

Example C5

1-Fluoro-2-fluoromethyl-3-butyn-2-yl Benzenesulfonate

An amount (1.2 g) of 1-fluoro-2-fluoromethyl-3-butyn-2-ol and benzenesulfonyl chloride (1.8 g) were dissolved in tetrahydrofuran (10 ml); to the solution under cooling with ice, 60% oily sodium hydride (0.48 g) was added in a nitrogen atmosphere. After the end of the addition, the mixture was stirred for 4 hours while its temperature was raised to room temperature. A hexane/ether mixed solvent (1/1) was added to the reaction mixture, which was then washed with water and a saturated aqueous solution of sodium chloride, dried with anhydrous sodium sulfate and concentrated under reduced pressure. The resulting residue was subjected to silica gel column chromatography (eluent; hexane/methylene chloride=1/1) to give the titled compound (2.2 g).

1H-NMR (CDCl$_3$) δ: 2.74(1H, s), 4.55–4.88(4H, m), 7.52–7.69(3H, m), 7.96(2H, d, J=7.3 Hz).

Example C6

1-Fluoro-2-fluoromethyl-3-butyn-2-yl 4-Trifluoromethylphenyl Ether (A) An amount (18.6 g) of 1-fluoro-2-fluoromethyl-3-butyn-2-yl methanesulfonate and 4-hydroxybenztrifluoride (19.8 g) were dissolved in acetonitrile (200 ml). To the solution under cooling with ice, cupric chloride dihydrate (3 mg) was added under a nitrogen atmosphere; then, diisopropylethylamine (12.3, g) as dissolved in acetonitrile (100 ml) was added dropwise. After the end of the dropwise addition, the mixture was stirred overnight while its temperature was raised to room temperature. The acetonitrile was distilled off under reduced pressure and hexane was added to the residue, which was washed with water, an aqueous solution of sodium hydroxide, dilute hydrochloric acid, aqueous sodium bicarbonate and a saturated aqueous solution of sodium chloride. The residue was dried with anhydrous sodium sulfate and concentrated under reduced pressure; the resulting residue was distilled under reduced pressure to give the titled compound (13.9 g).

1H-NMR (CDCl$_3$) δ: 2.77(1H, s), 4.52–4.79(4H, m), 7.32(2H, d, J=8.6 Hz), 7.59(2H, d, J=8.6 Hz).

(B) An amount (24.8 g) of 1-fluoro-2-fluoromethyl-3-butyn-2-yl p-toluenesulfonate and 16.2 g of 4-hydroxybenztrifluoride were dissolved in acetonitrile (400 ml). To the solution under cooling with ice, cupric chloride dihydrate (5 mg) was added under a nitrogen atmosphere; then, diisopropylethylamine (11.7 g) as dissolved in acetonitrile (100 ml) was added dropwise. After the end of the dropwise addition, the mixture was stirred for 6 hours while its temperature was raised to room temperature. The acetonitrile was distilled off under reduced pressure and hexane was added to the residue, which was washed with water, an aqueous solution of sodium hydroxide, dilute hydrochloric acid, aqueous sodium bicarbonate and a saturated aqueous solution of sodium chloride. The residue was dried with anhydrous sodium sulfate and concentrated under reduced pressure; the resulting residue was distilled under reduced pressure to give the titled compound (11.9 g).

Example C7

4-Bromo-1-fluoro-2-fluoromethyl-3-butyn-2-yl 4-Trifluoromethylphenyl Ether

An amount (13.9 g) of 1-fluoro-2-fluoromethyl-3-butyn-2-yl 4-trifluoromethylphenyl ether was dissolved in a solvent consisting of a mixture of tert-butyl methyl ether (100 ml) and tert-butyl alcohol (150 ml). To the solution under cooling with ice, potassium tert-butoxide (7.1 g) was added under a nitrogen atmosphere; after stirring for a while, bromine (3 ml) was added dropwise. After the end of the dropwise addition, the mixture was stirred for 30 minutes under stirring with ice. Hexane was added to the reaction mixture, which was then washed with water and a saturated aqueous solution of sodium chloride. The mixture was dried with anhydrous sodium sulfate and concentrated under reduced pressure to give the titled compound (18.1 g).

1H-NMR (CDCl$_3$) δ: 4.50–4.77(4H, m), 7.29(2H, d, J=8.6 Hz), 7.60(2H, d, J=8.6 Hz).

Example C8

4-Bromo-2,2-bis(fluoromethyl)-6-trifluoromethyl-2H-1-benzopyran

An amount (18.1 g) of 4-bromo-1-fluoro-2-fluoromethyl-3-butyn-2-yl 4-trifluoromethylphenyl ether was dissolved in solvent naphtha (100 ml) and the solution was refluxed for 4 hours under a nitrogen atmosphere. The solvent was distilled off under reduced pressure and the resulting residue was distilled under reduced pressure to give the titled compound (14.5 g).

1H-NMR (CDCl$_3$) δ: 4.41–4.71(4H, m), 6.14(1H, s), 6.95(1H, d, J=8.6 Hz), 7.50(1H, dd, J=8.6, 2.0 Hz), 7.71(1H, d, J=2.0 Hz).

Example C9

N-(2-Cyanoethyl)-2,2-bis(fluoromethyl)-6-trifluoromethyl-2H-1-benzopyran-4-carbothioamide An amount (103 mg) of 4-bromo-2,2-bis(fluoromethyl)-6-trifluoromethyl-2H-1-benzopyran was dissolved in diethyl ether (0.5 ml); to the solution, 1.68 M n-butyllithium (0.18 ml) was added at −10° C. under a nitrogen atmosphere. After stirring the reaction mixture for 10 minutes, copper(I) cyanide (27 mg) and tetrahydrofuran (0.6 ml) were added and the resulting mixture was stirred for 30 minutes at 0° C. Subsequently, a tetrahydrofuran solution (0.3 ml) of 2-cyanoethyl isothiocyanate (34 mg) was added and the mixture was stirred for 4 hours at 0° C. To the reaction mixture, a saturated aqueous solution of ammonium chloride was added, followed by extraction with diethyl ether; the resulting organic layer was washed with 2 N HCl, a saturated aqueous solution of sodium hydrogencarbonate and a saturated aqueous solution of sodium chloride, dried with anhydrous sodium sulfate and concentrated under reduced pressure; the resulting residue was subjected to silica gel column chromatography (eluent; dichloromethane/diethyl ether=10/1) to give the titled compound (8 mg), which was identical to the authentic sample.

Example C10

N-ethyl-2,2-bis(fluoromethyl)-6-trifluoromethyl-2H-1-benzopyran-4-carbothioamide An amount (103 mg) of 4-bromo-2,2-bis(fluoromethyl)-6-trifluoromethyl-2H-1-benzopyran was dissolved in diethyl ether (0.3 ml); to the solution, 1.68 M n-butyllithium (0.18 ml) was added at 0° C. under a nitrogen atmosphere. After stirring the reaction mixture for 2 minutes, a diethyl ether solution (0.3 ml) of ethyl isothiocyanate (34 mg) was added and the mixture was stirred for 2.5 hours at 0° C. The reaction mixture was diluted with diethyl ether, washed with a saturated aqueous solution of sodium hydrogencarbonate and a saturated aqueous solution of sodium chloride, dried with anhydrous sodium sulfate and concentrated under reduced pressure; the resulting residue was subjected to silica gel column chromatography (eluent; hexane/ethyl acetate=4/1) to give the titled compound (60 mg) as a pale yellow crystal.

mp 65–67° C. 1H-NMR (CDCl$_3$) δ: 1.36(3h, t, J=7.2 Hz,), 3.82(2H, m), 4.35–4.80(4H, m), 5.84(1H, s), 7.00(1H, d, J=8.6 Hz), 7.40(1H, br s), 7.48(1H, d, J=8.6 Hz), 7.69(1H, s).

Example C11

O-methyl 2,2-bis(fluoromethyl)-6-trifluoromethyl-2H-1-benzopyran-4-carbothioate

An amount (65 mg) of 4-bromo-2,2-bis(fluoromethyl)-6-trifluoromethyl-2H-1-benzopyran was dissolved in t-butyl methyl ether (2 ml); to the solution, 1.69 M n-butyllithium (0.11 ml) was added at −70° C. under a nitrogen atmosphere and the mixture was stirred for 10 minutes. Then, dimethoxycarbon sulfide (39 mg) was slowly added dropwise to the reaction mixture, which was stirred for 30 minutes at −70° C. To the reaction mixture, a saturated aqueous solution of ammonium chloride was added, followed by extraction with hexane/ethyl acetate (3/1). The resulting organic layers were washed with a saturated aqueous solution of sodium chloride, dried with anhydrous sodium sulfate and concentrated under reduced pressure; the resulting residue was subjected to silica gel column chromatography (eluent; hexane/ethyl acetate=2/1) to give the titled compound (36 mg) as a colorless oil.

1H-NMR (CDCl$_3$) δ: 4.26(3H, s), 4.51(2H, ddd, J=46.5, 9.9, 2.0 Hz), 4.68(2H, ddd, J=46.8, 9.9, 1.6 Hz), 6.39(1H, s), 7.03(1H, d, J=8.6 Hz), 7.48(1H, d, J=8.6 Hz), 7.74(1H, s).

Example C12

O-ethyl 2,2-bis(fluoromethyl)-6-trifluoromethyl-2H-1-benzopyran-4-carbothioate

An amount (58 mg) of 4-bromo-2,2-bis(fluoromethyl)-6-trifluoromethyl-2H-1-benzopyran was dissolved in t-butyl methyl ether (2 ml); to the solution, 1.69 M n-butyllithium (0.108 ml) was added at −70° C. under a nitrogen atmosphere and the mixture was stirred for 15 minutes. Then, diethyl thiocarbonate (67 mg) was added dropwise to the reaction mixture, which was stirred for 30 minutes at −70° C. To the reaction mixture, a saturated aqueous solution of ammonium chloride was added, followed by extraction with hexane/ethyl acetate (3/1). The resulting organic layers were washed with a saturated aqueous solution of sodium chloride, dried with anhydrous sodium sulfate and concentrated under reduced pressure; the resulting residue was subjected to silica gel column chromatography (eluent; hexane/ethyl acetate=2/1) to give the titled compound (31 mg) as a colorless oil.

1H-NMR (CDCl$_3$) δ: 1.50(3H, t, J=7.4 Hz), 4.43–4.76 (6H, m), 6.42(1H, s), 7.03(1H, d, J=8.6 Hz), 7.48(1H, d, J=8.6 Hz), 7.77(1H, s).

Example C13

N-(2-Cyanoethyl)-2,2-bis(fluoromethyl)-6-trifluoromethyl-2H-1-benzopyran-4-carbothioamide O-methyl 2,2-bis(fluoromethyl)-6-trifluoromethyl- 2H-1-benzopyran-4-carbothioate (0.34 g) and DBU (10 mg) were dissolved in tetrahydrofuran (5 ml); to the solution, 3-aminopropionitrile (0.2 ml) was added at room temperature in a nitrogen atmosphere and the resulting mixture was stirred for 7 hours at room temperature. Ethyl acetate was added to the reaction mixture, which was washed with water, dilute HCl, aqueous sodium bicarbonate and a saturated aqueous solution of sodium chloride. The mixture was dried with anhydrous sodium sulfate and concentrated under reduced pressure; the resulting residue was subjected to silica gel column chromatography (eluent; methylene chloride) to give the titled compound (0.33 g), which was identical to the authentic sample.

Example C14

Methyl 5-fluoro-4-fluoromethyl-4-(4-trifluoromethylphenoxy)-2-pentynoate

An amount (0.53 g) of 1-fluoro-2-fluoromethyl-3-butyn-2-yl 4-trifluoromethylphenyl ether was dissolved in diethyl ether (3 ml); to the solution under cooling with ice, a hexane solution (1.4 ml) of 1.69 M n-butyllithium was added dropwise under a nitrogen atmosphere. After the end of the dropwise addition, the mixture was stirred for 1 hour under cooling with ice. The resulting mixture was added dropwise to a solution of methyl chloroformate (0.38 g) in diethyl ether (3 ml) under a nitrogen atmosphere under cooling with ice. After stirring the mixture for 1 hour under cooling with ice, hexane was added, followed by washing with water and a saturated aqueous solution of sodium chloride. The mixture was dried with anhydrous sodium sulfate and concentrated under reduced pressure; the resulting residue was subjected to silica gel column chromatography (eluent; hexane/methylene chloride=1/1) to give the titled compound (0.51 g).

1H-NMR (CDCl$_3$) δ: 3.80(3H, s), 4.55–4.82(4H, m), 7.31(2H, d, J=8.6 Hz), 7.62(2H, d, J=8.6 Hz).

Example C15

Methyl 2,2-Bis(fluoromethyl)-6-trifluoromethyl-2H-1-benzopyran-4-carboxylate

An amount (0.28 g) of methyl 5-fluoro-4-fluoromethyl-4-(4-trifluoromethylphenoxy)-2-pentynoate was added dropwise to o-dichlorobenzene (1.0 ml) during refluxing under a nitrogen atmosphere. After the end of the dropwise addition, the reaction mixture was refluxed for 3 hours. The solvent was distilled off under reduced pressure and the resulting residue was subjected to silica gel column chromatography (eluent; 10% tetrahydrofuran/hexane) to give the titled compound (0.25 g).

1H-NMR (CDCl$_3$) δ: 3.90(3H, s), 4.45–4.74(4H, m), 6.70(1H, s), 7.00(1H, d, J=8.6 Hz), 7.49(1H, br. d, J=8.6 Hz), 8.32(1H, br. s).

Example C16

O-Methyl 2,2-bis(fluoromethyl)-6-trifluoromethyl-2H-1-benzopyran-4-carbothioate

Methyl 2,2-bis(fluoromethyl)-6-trifluoromethyl-2H-1-benzopyran-4-carboxylate (1.0 g) was dissolved in xylene (2.5 ml); to the solution, 2,4-bis(4-methoxyphenyl)-1,3-dithia-2,4-diphosphethane-2,4-disulfide (1.6 g) was added under a nitrogen atmosphere and the mixture was refluxed for 6 hours. The insoluble matter was filtered off by addition of a hexane and toluene (2/1) mixed solvent. The filtrate was concentrated under reduced pressure and the resulting residue was subjected to silica gel column chromatography (eluent; hexane/methylene chloride=2/1) to give the titled compound (0.75 g).

1H-NMR (CDCl$_3$) δ: 4.26(3H, s), 4.45–4.75(4H, m), 6.39(1H, s), 7.03(1H, d, J=8.6 Hz), 7.48(1H, br. d, J=8.6 Hz), 7.74(1H, br. s).

Example C17

Preparation of N-(2-Cyanoethyl)-2,2-bis(fluoromethyl)-6-trifluoromethyl-2H-1-benzopyran-4-carboxamide A mixture of 4-bromo-2,2-bis(fluoromethyl)-6-trifluoromethyl-2H-1-benzopyran (1.73 g), 2-cyanoethylamine (1.44 g), potassium iodide (0.86 g), triphenylphosphine (26 mg), palladium acetate (11 mg) and N,N-dimethylacetamide (10 ml) was stirred under a CO atmosphere at 100° C. for 3 hours. To the reaction mixture, 2 N HCl was added and the precipitating crystals were recovered by filtration. To the recovered crystals, ethyl acetate was added and the insoluble matter was filtered off; the filtrate was washed with a saturated aqueous solution of sodium thiosulfate and a saturated aqueous solution of sodium chloride, dried with anhydrous sodium sulfate and concentrated under reduced pressure; the resulting residue was recrystallized with an ethanol and water mixed solvent to give N-(2-cyanoethyl)-2,2-bis(fluoromethyl)-6-trifluoromethyl-2H-1-benzopyran-4-carboxamide (1.46 g) represented by the formula (C1-1) and having a melting point of 129–131° C.

1H-NMR (DMSO-d$_6$) δ: 2.77(2H, t, J=6.3 Hz), 3.47(2H, q, J=6.3 Hz), 4.53–4.82(4H, m), 6.14(1H, s), 7.11(1H, d, J=8.6 Hz), 7.59(1H, dd, J=8.6, 2.0 Hz), 7.83(1H, d, J=2.0 Hz), 8.85–9.00(1H, m). MSm/z:360(M$^+$).

Example C18

Preparation of N-(2-Cyanoethyl)-2,2-bis(fluoromethyl)-6-trifluoromethyl-2H-1-benzopyran-4-carboxamide via 2,2-bis(fluoromethyl)-6-trifluoromethyl-2H-1-benzopyran-4-carboxylic acid (alternative method for preparing the end compound of Example C17)

1) 2,2-Bis(fluoromethyl)-6-trifluoromethyl-2H-1-benzopyran-4-carboxylic Acid

A mixture of 4-bromo-2,2-bis(fluoromethyl)-6-trifluoromethyl-2H-1-benzopyran (1.72 g), potassium acetate (2.00 g), potassium iodide (0.85 g), triphenylphosphine (27 mg), palladium acetate (11 mg) and N,N-dimethylacetamide (10 ml) was stirred under a CO atmosphere at 120° C. for 9 hours. To the reaction mixture, 2 N HCl was added and the precipitating crystals were recovered by filtration. To the recovered crystals, ethyl acetate was added and the insoluble matter was filtered off; the filtrate was washed with a saturated aqueous solution of sodium thiosulfate and a saturated aqueous solution of sodium chloride, dried with anhydrous sodium sulfate and concentrated under reduced pressure; the resulting residue was dissolved in a saturated aqueous solution of sodium hydrogencarbonate washed with dichloromethane; concentrated HCl was added to the resulting aqueous layer to make it acidic and the precipitating crystals were recovered by filtration. The recovered crystals were dissolved in ethyl acetate, dried with anhydrous magnesium sulfate and concentrated under reduced pressure; the resulting residue was recrystallized with a solvent consisting of a mixture of ethyl acetate and hexane, thereby giving 2,2-bis(fluoromethyl)-6-trifluoromethyl-2H-1-benzopyran-4-carboxylic acid (1.25 g) represented by the formula (C2-1) and having a melting point of 162–163° C.

1H-NMR (DMSO-$d_6$) δ: 4.56–4.85(4H, m), 6.81(1H, s), 7.08(1H, d, J=8.6 Hz), 7.60(1H, dd, J=8.6, 2.0 Hz), 7.83(1H, d, J=2.0 Hz), 8.86(1H, d, J=2.0 Hz), 13.45–13.70(1H, m). MSm/z:308($M^+$).

2) N-(2-Cyanoethyl)-2,2-bis(fluoromethyl)-6-trifluoromethyl-2H-1-benzopyran-4-carboxamide A mixture of 2,2-bis(fluoromethyl)-6-trifluoromethyl-2H-1-benzopyran-4-carboxylic acid (1.55 g), thionyl chloride (0.51 ml) and toluene (5 ml) was heated at 80° C. for 5 hours. The reaction mixture was concentrated under reduced pressure; to the resulting residue, a mixture of 2-cyanoethylamine (0.42 g) and acetonitrile (5 ml) was added on an ice bath; following the addition of a mixture of triethylamine (2.52 g) and acetonitrile (5 ml), the resulting mixture was stirred first on an ice bath for 10 minutes, then at room temperature for 1 hour. To the reaction mixture, 2 N HCl was added and the precipitating crystals were recovered by filtration. The recovered crystals were dissolved in ethyl acetate, washed with a saturated aqueous solution of sodium chloride, dried with anhydrous sodium sulfate and concentrated under reduced pressure; the resulting residue was recrystallized with an ethanol and water mixed solvent to give N-(2-cyanoethyl)-2,2-bis(fluoromethyl)-6-trifluoromethyl-2H-1-benzopyran-4-carboxamide (1.61 g) represented by the formula (C2-2) and having a melting point of 129–131° C.

1H-NMR (DMSO-$d_6$) δ: 2.77(2H, t, J=6.3 Hz), 3.47(2H, q, J=6.3 Hz), 4.53–4.82(4H, m), 6.14(1H, s), 7.11(1H, d, J=8.6 Hz), 7.59(1H, dd, J=8.6, 2.0 Hz), 7.83(1H, d, J=2.0 Hz), 8.85–9.00(1H, m). MSm/z:360($M^+$).

Example C19

N-(2-Cyanoethyl)-2,2-bis(fluoromethyl)-6-trifluoromethyl-2H-1-benzopyran-4-carboxamide To an ice-cooled mixture of 2,2-bis(fluoromethyl)-6-trifluoromethyl-2H-1-benzopyran-4-carboxylic acid (0.20 g) and tetrahydrofuran (3 ml), N,N'-carbonyldiimidazole (0.12 g) was added with stirring and the mixture was stirred for 1 hour. Thereafter, 2-cyanoethylamine (0.06 g) was added and the mixture was stirred first under cooling with ice for 1 hour, then at room temperature for 12 hours. To the reaction mixture, an aqueous solution of potassium carbonate was added, followed by extraction with methylene chloride; the organic layer was washed with water and dried; the solvent was distilled off and the resulting residue was recrystallized with a solvent consisting of a mixture of ethyl acetate and hexane, thereby giving the titled compound (0.20 g) having a melting point of 135–136° C.

1H-NMR (DMSO-$d_6$) δ: 2.77(2H, t, J=6.3 Hz), 3.47(2H, q, J=6.3 Hz), 4.53–4.82(4H, m), 6.14(1H, s), 7.11(1H, d, J=8.6 Hz), 7.59(1H, dd, J=8.6, 2.0 Hz), 7.83(1H, d, J=2.0 Hz), 8.85–9.00(1H, m). MSm/z:360($M^+$).

Example C20

N-(2-Cyanoethyl)-6-pentafluoroethyl-2,2-bis(fluoromethyl)-2H-1-benzopyran-4-carboxamide To an ice-cooled mixture of 2,2-bis(fluoromethyl)-6-trifluoromethyl-2H-1-benzopyran-4-carboxylic acid (0.20 g) and tetrahydrofuran (3 ml), N,N'-carbonyldiimidazole (0.10 g) was added with stirring and the mixture was stirred for 1 hour. Thereafter, 2-cyanoethylamine (0.05 g) was added and the mixture was stirred first under cooling with ice for 1 hour, then at room temperature for 12 hours. To the reaction mixture, an aqueous solution of potassium carbonate was added, followed by extraction with methylene chloride; the organic layer was washed with water and dried; the solvent was distilled off and the resulting residue was recrystallized with a solvent consisting of a mixture of ethyl acetate and hexane, thereby giving the titled compound (0.19 g) having a melting point of 144–145° C.

1H-NMR ($CDCl_3$) δ: 2.73(2H, t, J=6.3 Hz), 3.67(2H, q, J=6.3 Hz), 4.44–4.73(4H, m), 6.08(1H, s), 6.40–6.60(1H, m), 7.03(1H, d, J=8.6 Hz), 7.47(1H, dd, J=8.6, 2.0 Hz), 7.81(1H, d, J=2.0 Hz). MSm/z:410($M^+$).

INDUSTRIAL APPLICABILITY

The processes of the present invention for producing 4-substituted benzopyran derivatives involve fewer steps and feature greater convenience and safety than the prior art processes; therefore, these processes have outstanding practical utility as methods of synthesizing intermediates for the manufacture of medicines, agrichemicals, cosmetics, etc.

A List of Chemical Formulae (Part 1)

Compounds Described in Prior Art Documents (1)

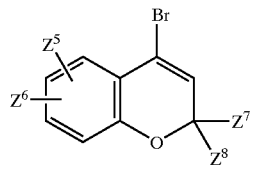

(XVIII)

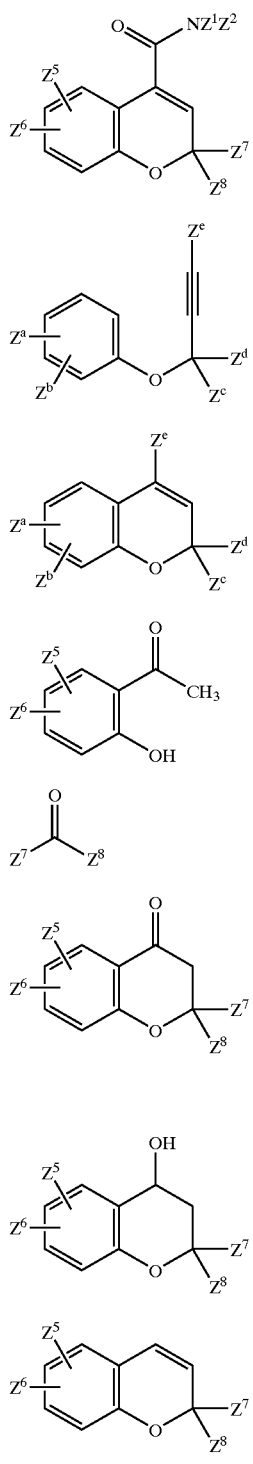
A List of Chemical Formulae (Part 2)
Compounds Described in Prior Art Documents (2)
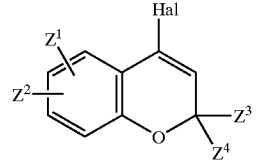
(XXVII)
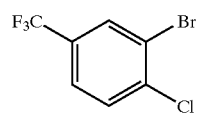
(IIf)
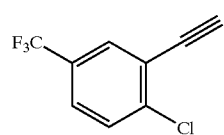
(XIX)
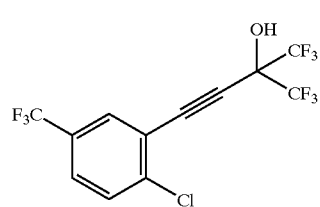
(XX)
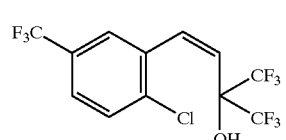
(XXI)
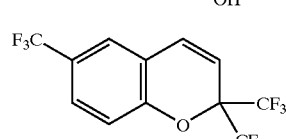
(XXII)
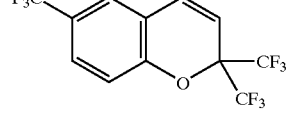
(XXIII)
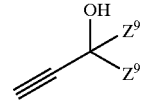
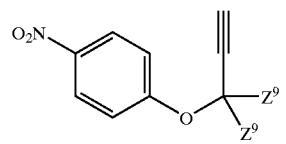
(XXIV)
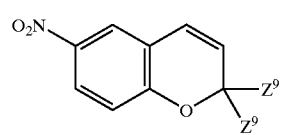
(XXV)
A List of Chemical Formulae (Part 3)
Compounds Described in Prior Art Documents (3)
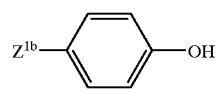
(H)

-continued

A List of Chemical Formulae (Part 4)
Compounds Realted to the Invention (1)

(XI)
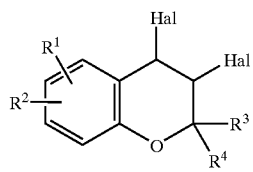
A List of Chemical Formulae (Part 5)
Compounds Realted to the Invention (2)
(G-I)
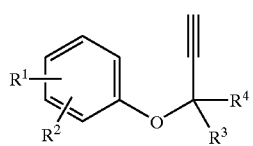
(G-II)
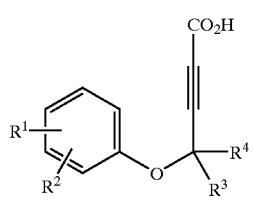
(G-IVa)
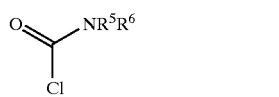
(G-V)
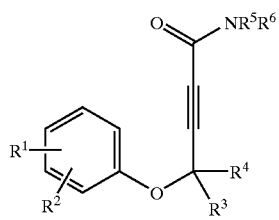
(C-I)
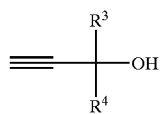
(C-IV)
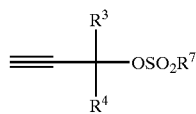
(C-V)
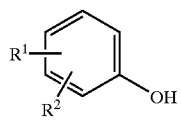
(C-VI)
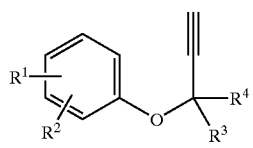
(D-II)
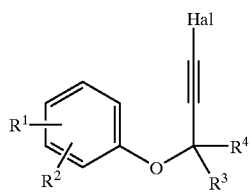
(G-VII)
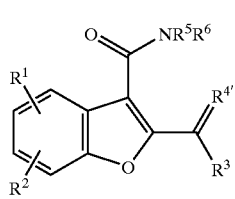
A List of Chemical Formulae (Part 6)
Compounds Realted to the Invention (3)
(H-IV)
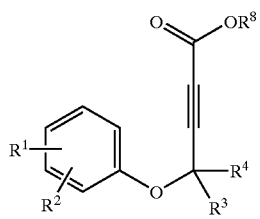
(H-V)
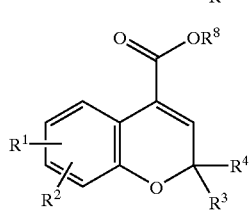
(G-VIa)
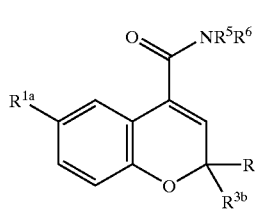
(IIa)
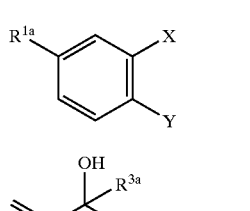
(IIIa)
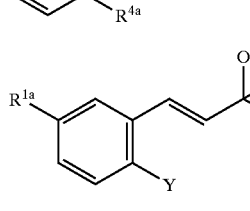
(IVa)
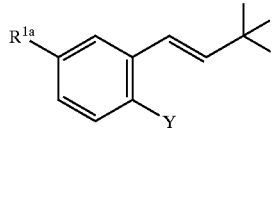

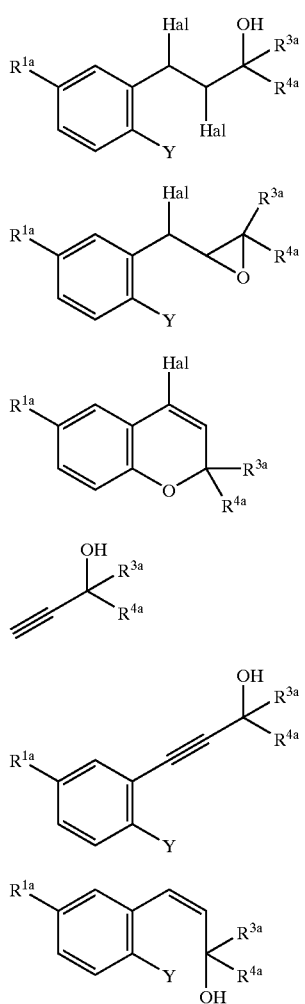
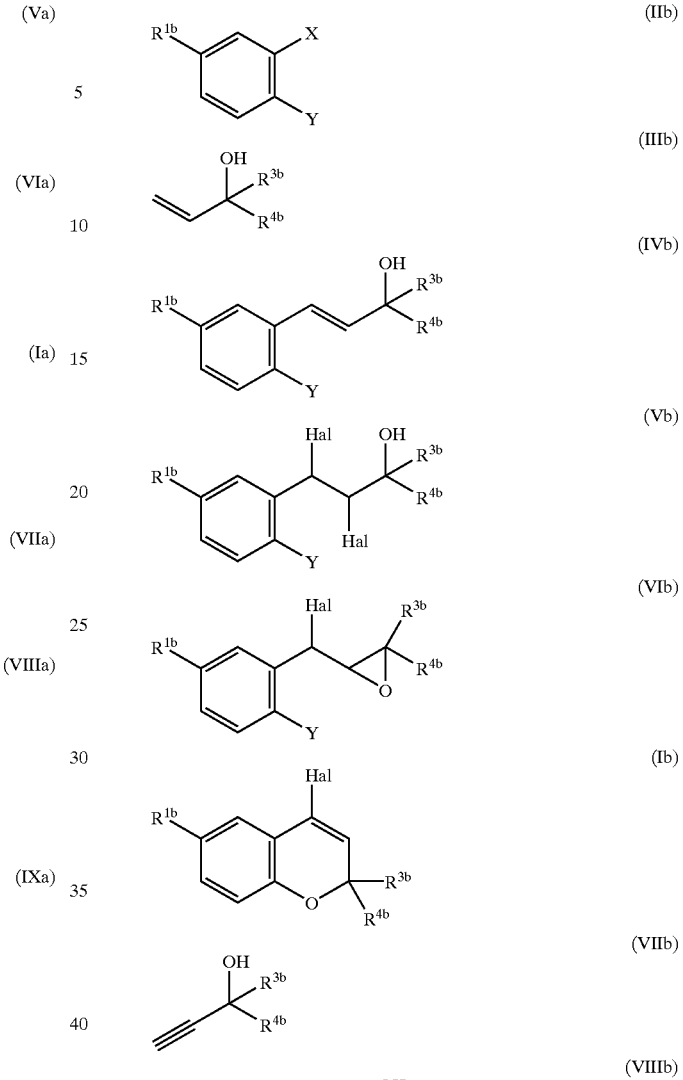
A List of Chemical Formulae (Part 7)
Compounds Realted to the Invention (4)
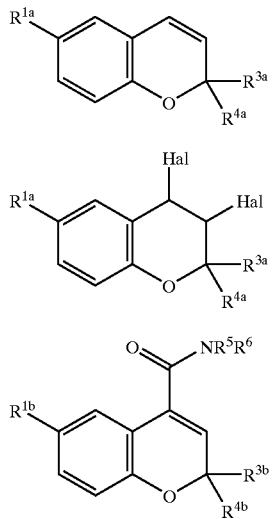
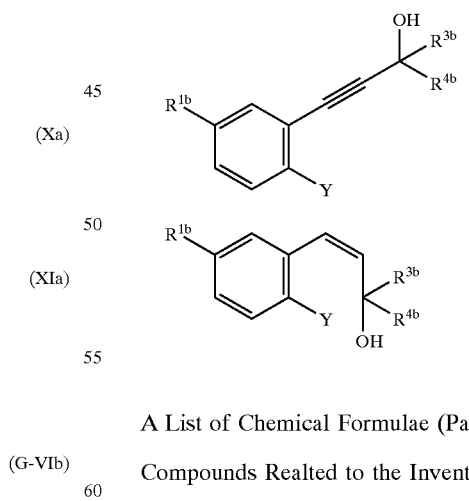
A List of Chemical Formulae (Part 8)
Compounds Realted to the Invention (5)
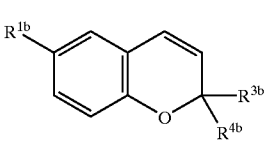

-continued
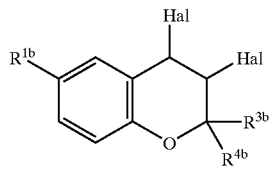 (XIb)
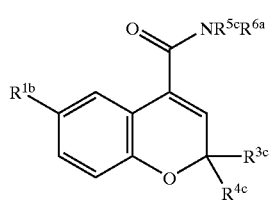 (G-VIc)
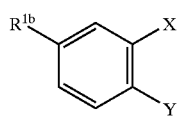 (IIb)
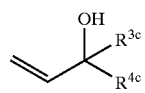 (IIIc)
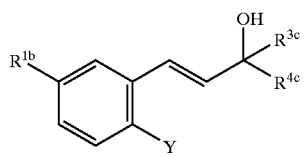 (IVc)
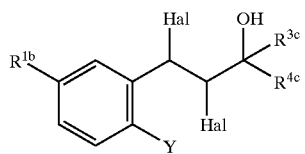 (Vc)
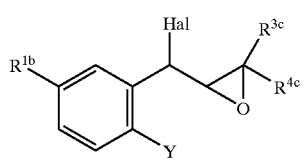 (VIc)
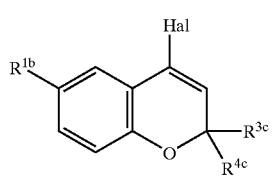 (Ic)
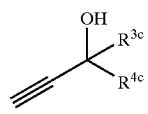 (VIIc)
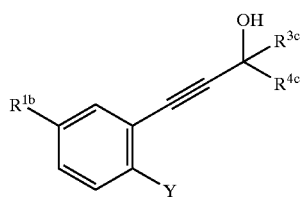 (VIIIc)
-continued
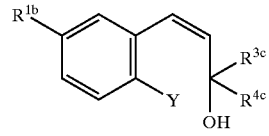 (IXc)
A List of Chemical Formulae (Part 9)
Compounds Realted to the Invention (6)
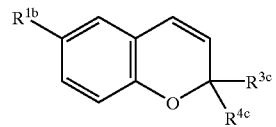 (Xc)
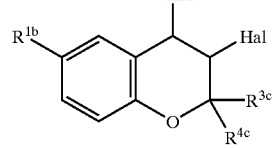 (XIc)
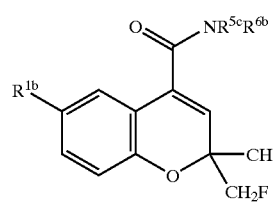 (G-VId)
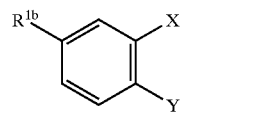 (IId)
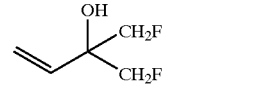 (IIId)
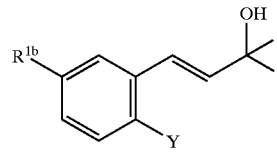 (IVd)
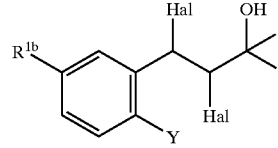 (Vd)
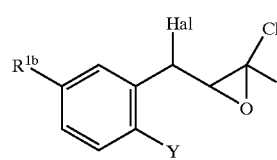 (VId)

-continued
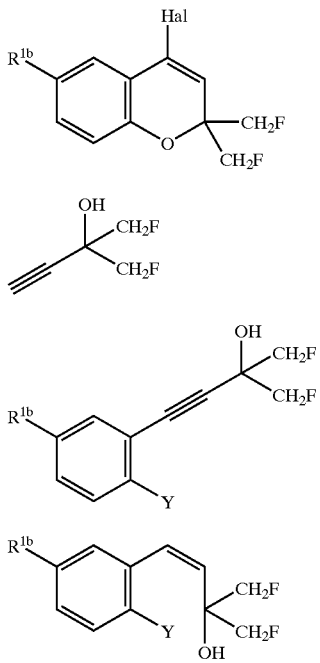
A List of Chemical Formulae (Part 10)
Compounds Realted to the Invention (7)
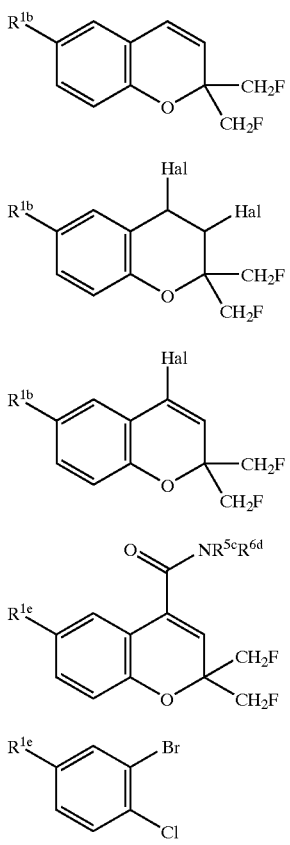
-continued
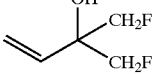 (IIId)
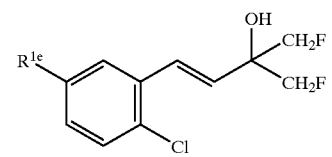 (IVe)
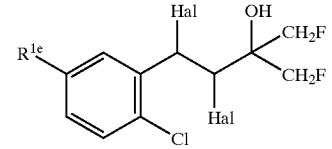 (Ve)
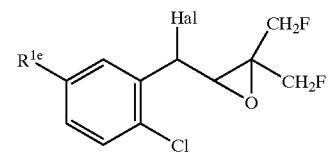 (VIe)
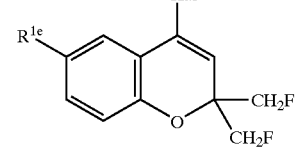 (Ie)
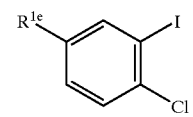 (IIe2)
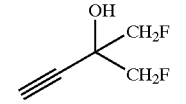 (VIId)
A List of Chemical Formulae (Part 11)
Compounds Realted to the Invention (8)
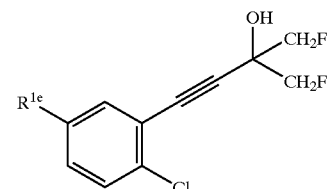 (VIIIe)
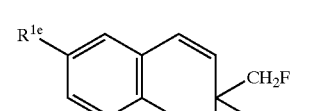 (IXe)
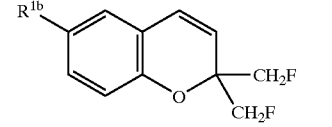 (Xd)

-continued
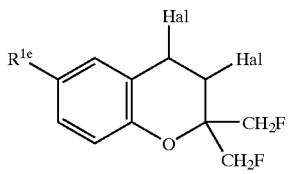
(XIe)
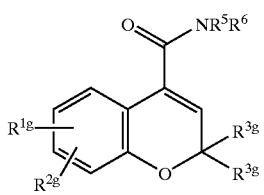
(G-VIg)
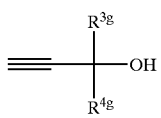
(C-Ig)
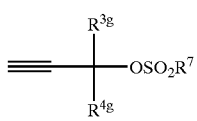
(C-IVg)
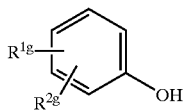
(C-Vg)
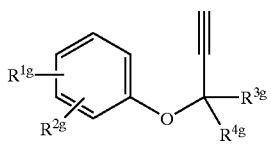
(G-Ig)
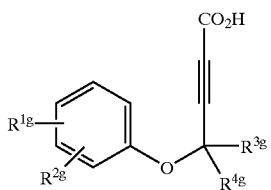
(G-IIg)
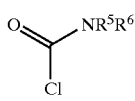
(G-IVa)
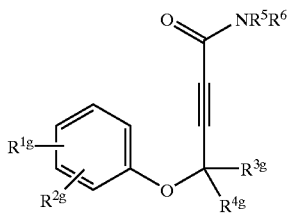
(G-Vg)
A List of Chemical Formulae (Part 12)
Compounds Realted to the Invention (9)
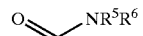
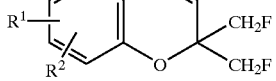
(G-VIh)
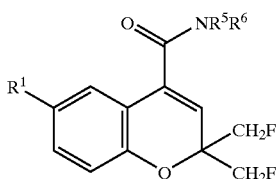
(G-VIi)
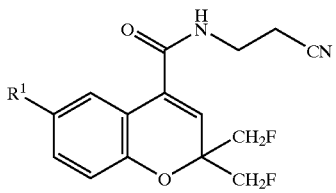
(G-VIj)
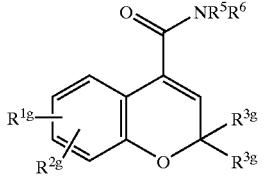
(G-VIg)
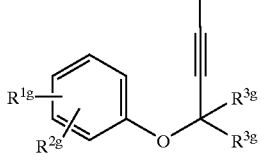
(G-Vk)
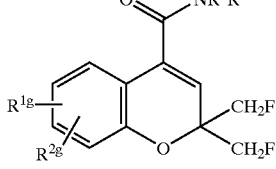
(G-VIl)
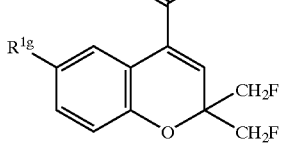
(G-VIm)
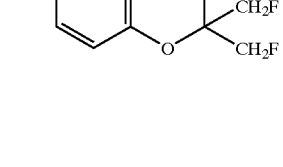
(G-VIn)

(Iz)
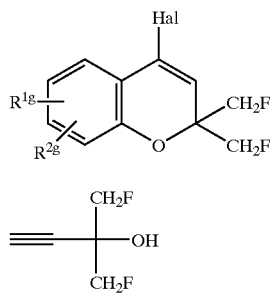
A List of Chemical Formulae (Part 13)
Compounds Realted to the Invention (10)
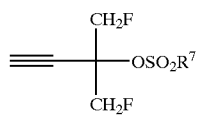 (C-IVa)
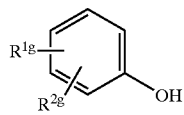 (C-Va)
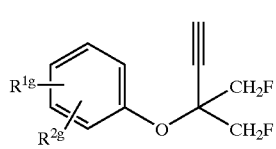 (C-VIa)
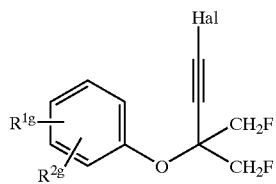 (D-IIa)
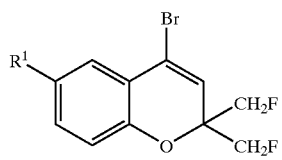 (Iy)
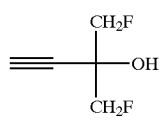 (C-Ia)
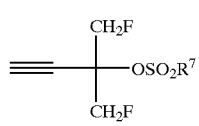 (C-IVa)
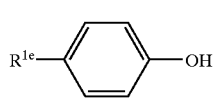 (C-Va)
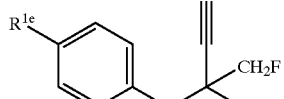 (C-VIb)
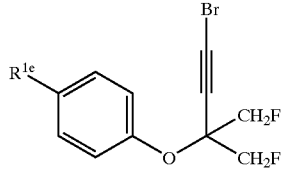 (D-IIb)
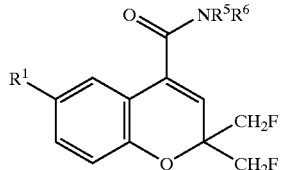 (G-VIz)
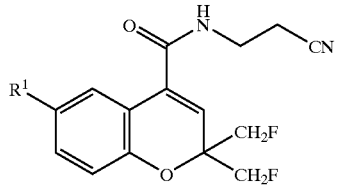 (G-VIy)
A List of Chemical Formulae (Part 14)
Compounds Realted to the Invention (11)
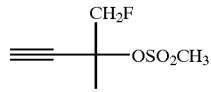 (C-IVb)
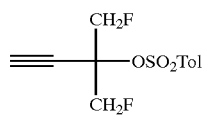 (C-IVc)
 (C-Va)
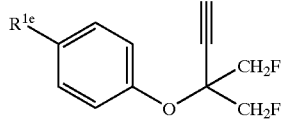 (C-VIb)
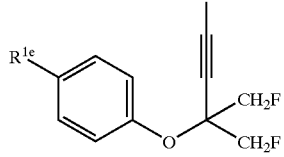 (D-IIb)

(Iq) 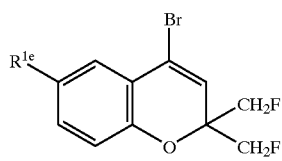
(G-VI) 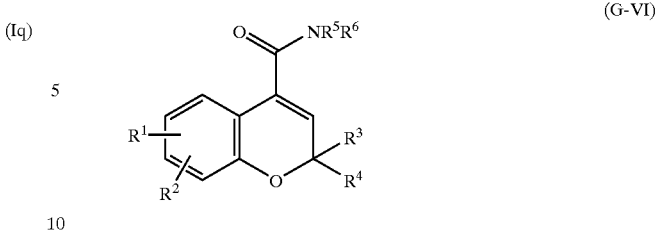
A List of Chemical Formulae (Part 15)
Synthesis Procedures for Process Schemes (1) and (2)
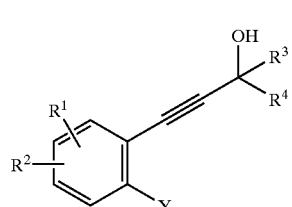
(VIII)
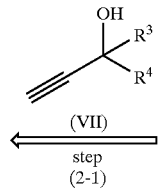
(VII)
step (2-1)
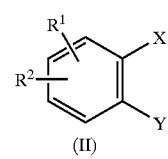
(II)
step (1-1)
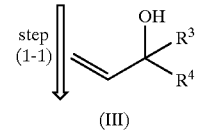
(III)
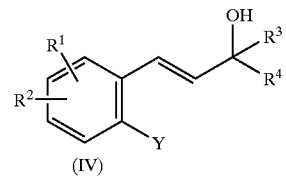
(IV)
step (2-2) reducing agent
step (1-2) halogenating agent
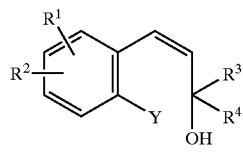
(IX)
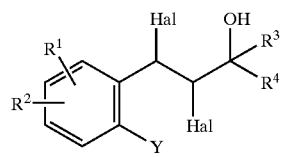
(V)
step (2-3) base
step (1-3) base
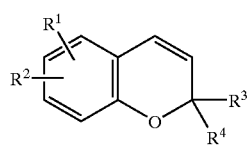
(X)
step (2-4) halogenating agent
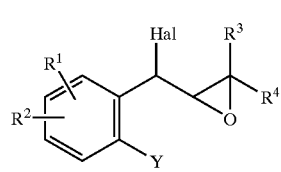
(VI)

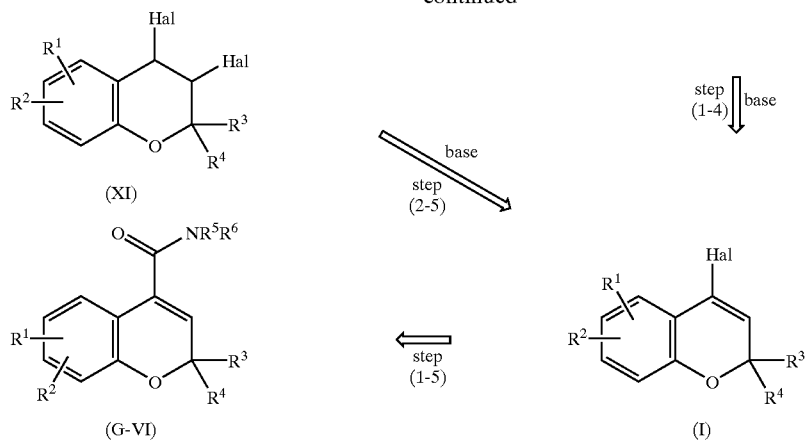
A List of Chemical Formulae (Part 16)
Synthesis Procedures for Process Schemes (3) and (4)
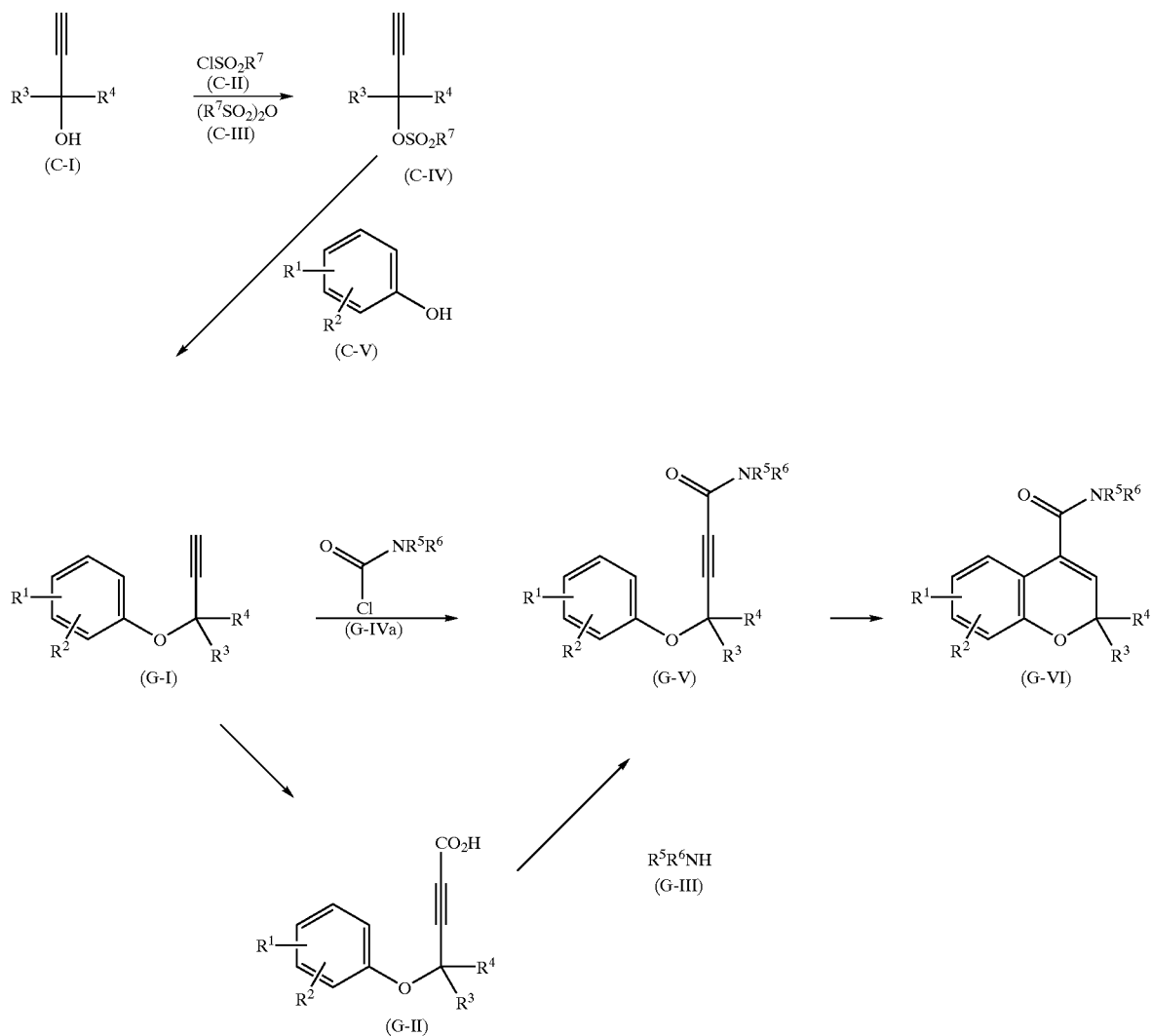

A List of Chemical Formulae (Part 17)
Synthesis Procedures for Process Schemes (5) and (6)
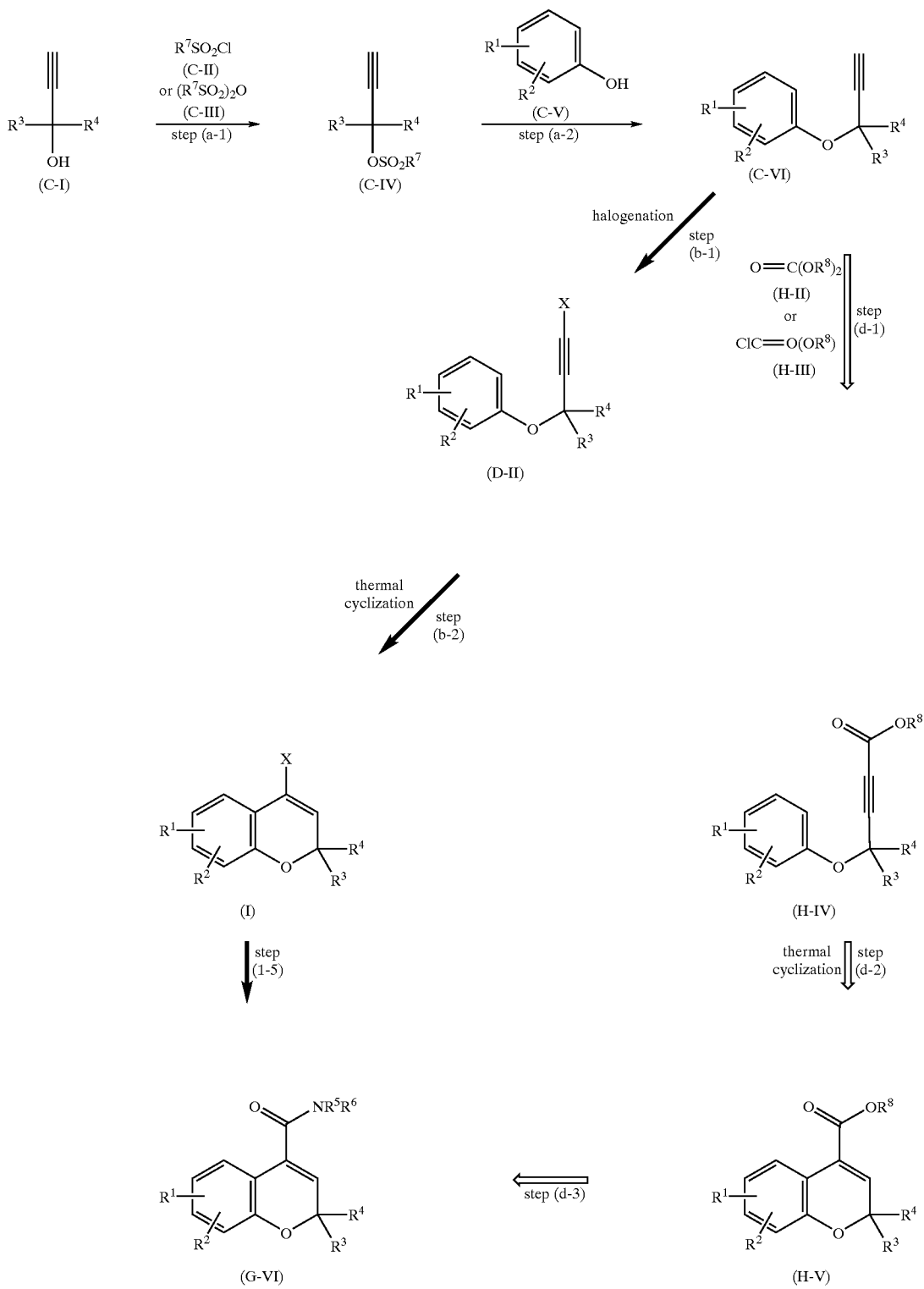

What is claimed is:

1. A process for producing 4-substituted benzopyran derivatives represented by formula (G-VI)

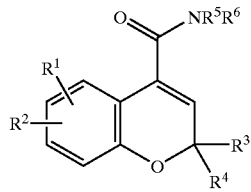

where $R^1$ and $R^2$ which may be the same or different represent a hydrogen atom, an optionally substituted lower alkyl group, an optionally substituted lower alkoxy group, an optionally substituted lower alkoxycarbonyl group, an optionally substituted lower alkylsulfonyl group, an optionally substituted arylsulfonyl group, a halogen atom, a nitro group, a cyano group or $NY_aY_b$ where $Y_a$ and $Y_b$ which may be the same or different and each represents a hydrogen atom, an optionally substituted lower alkyl group, an optionally substituted lower alkoxycarbonyl group, an acyl group, an optionally substituted lower alkylsulfonyl group or an optionally substituted arylsulfonyl group or, when taken together with the nitrogen atom to which they are bound, may form a 3- to 8-membered ring or, when taken together, represent a substituent =N—O—N=; $R^3$ and $R^4$ which may be the same or different represent a hydrogen atom or an optionally substituted lower alkyl group or, when taken together with the carbon atom to which they are bound, represent a polymethylene group or a substituent forming a heterocycle, provided that $R^3$ and $R^4$ are not both a hydrogen atom; $R^5$ and $R^6$ which may be the same or different represent a hydrogen atom or an optionally substituted lower alkyl group by scheme (2), comprising the following steps (2):(2-1)→(2-2)→(2-3)→(2-4)→(2-5)→(1-5);

(2-1) reaching a compound of formula (II)

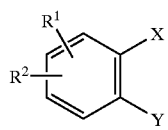

were X and Y which may be the same or different represent a leaving group selected from a halogen atom, an optionally substituted lower alkylsulfonyloxy group or an arylsulfonyloxy group; $R^1$ and $R^2$ have the same meanings as defined above with acetylene of formula (VII)

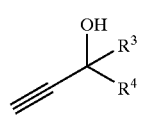

where $R^3$ and $R^4$ have the same meanings as defined above to give a compound of formula (VIII)

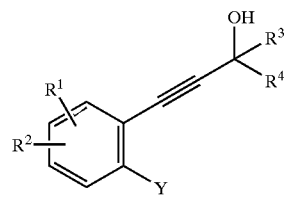

where Y, $R^1$, $R^2$, $R^3$ and $R^4$ have the same meanings as defined above;

(2-2) reacting the resulting compound of formula (VIII) with a reducing agent to give a compound of formula (IX)

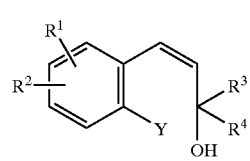

where Y, $R^1$, $R^2$, $R^3$ and $R^4$ have the same meanings as defined above;

(2-3) reacting the resulting compound of formula (X) with a base to give a benzopyran derivative of formula (X)

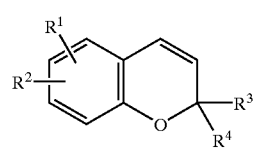

where $R^1$, $R^2$, $R^3$ and $R^4$ have the same meanings as defined above;

(2-4) reacting the resulting compound of formula (X) with a halogenating agent to give a 3,4-dihalobenzopyran derivative of formula (XI)

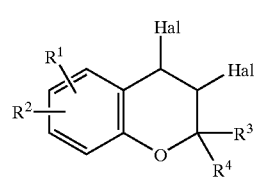

where $R^1$, $R^2$, $R^3$, $R^4$ and Hal have the same meanings as defined above;

(2-5) reacting the resulting compound of formula (XI) with a base to give a 4-halobenzopyran derivative of formula (I)

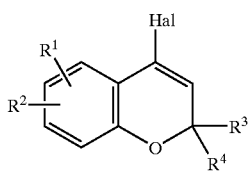

(I)

where $R^1$, $R^2$, $R^3$, $R^4$ and Hal have the same meanings as defined above;
to give a 4-substituted benzopyran derivative of formula (G-VT) set forth above.

2. A process for producing 4-substituted benzopyran derivatives represented by formula (G-VIa)

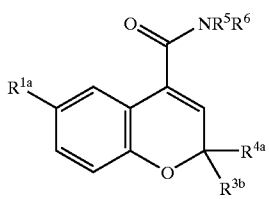

(G-VIa)

where $R^{1a}$ represents a lower perfluoroalkyl group, a nitro group or a cyano group; $R^{3a}$ and $R_{4a}$ which may be the same or different represent a hydrogen atom, an optionally substituted lower alkyl group or, when taken together with the carbon atom to which they are bound, represent a polymathylene group or a substituent forming a heterocycle, provided that $R^{3a}$ and $R^{4a}$ are not both a hydrogen atom; $R^5$ and $R^6$ which may be the same or different represent a hydrogen atom or an optionaly substituted lower alkyl group by scheme (2a) comprising the following steps:

(2a) (2a-1)→(2a-2)→(2a-3)→(2a-4)→(2a-5)→(1a-5);
(2a-2) treating a compound of formula (VIIIa)

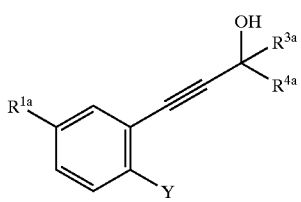

(VIIIa)

with a reducing agent to give a compound of formula (IXa)

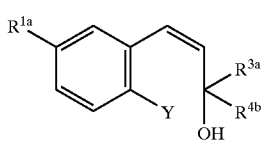

(IXa)

where $R^{1a}$, $R^{3a}$ and $R^{4a}$ have the same meanings as defined above, and Y is as defined in claim 1;

(2a-3) reacting the resulting compound of formula (IXa) with a base to give a benzopyran derivative of formula (Xa)

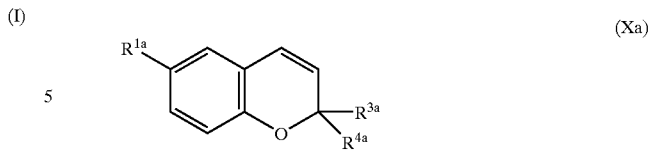

(Xa)

where $R^{1a}$, $R^{3a}$ and $R^{4a}$ have the same meanings as defined above;

(2a-4) reacting the resulting compound of formula (Xa) with. a halogenating agent to give a 3,4-dihalobenzopyran derivative of formula (XIa)

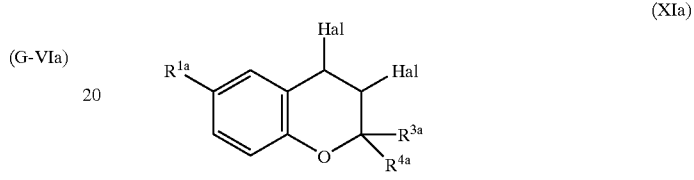

(XIa)

where $R^{1a}$, $R^{3a}$ and $R^{4a}$ have the same meanings as defined above and Hal represents a halogen atom;

(2a-5) treating the resulting compound of formula (XIa) with a base to give a 4-halobenzopyran derivative of formula (Ia) set forth above.

3. A process for producing 4-substituted benzopyran derivatives represented by the general formula (G-VIb)

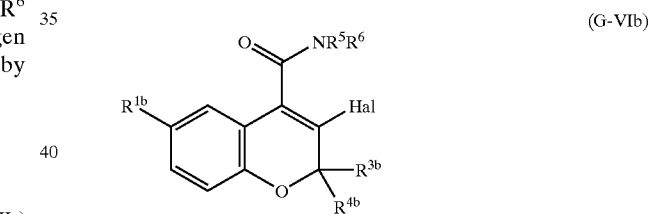

(G-VIb)

where $R^{1b}$ represents a lower perfluoroalakyl group; $R^{3b}$ and $R^{4b}$ which may be the same or different represent a hydrogen atom, an optionally substituted lower alkyl group or, when taker together with the carbon atom to which they are bound, represent a polymethylene group, provided that $R^{3b}$ and $R^{4b}$ are not both a hydrogen atom; $R^5$ and $R^6$ which may be the same or different represent a hydrogen atom or an optionally substituted lower alkyl group) by scheme(2b) comprising the following steps:

(2b) (2b-1)→(2b-2)→(2b-3)→(2ba-4)→(2b-5)→(1b-5);
(2b-1) reactig a compound of formula (IIb)

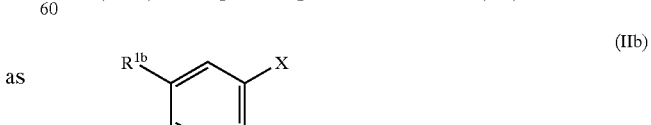

(IIb)

with acetylene of formula (VIIb)

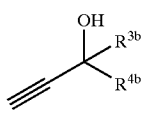
(VIIb)

where $R^{3b}$ and $R^{4b}$ have the same meanings as defined above to give a compound of formula (VIIIb)

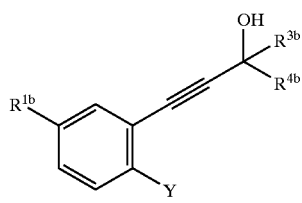
(VIIIb)

where $R^{1b}$, $R^{3b}$ and $R^{4b}$ have the same meanings as defined above; and Y is a defined in claim 1;

(2b-2) treating the resulting compound of formula (VIIIb) with a reducing agent to give a compound of formula (IXb)

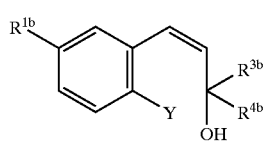
(IXb)

where Y, $R^{1b}$, $R^{3b}$ and $R^{4b}$ have the same meanings as defined above;

(2b-3) reacting the resulting compound of formula (IXb) with a base to give a benzopyran derivative of formula (Xb)

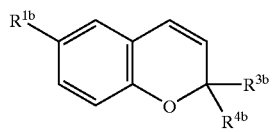
(Xb)

where $R^{1b}$, $R^{3b}$ and $R^{4b}$ have the same meanings as defined above;

(2b-4) reacting the resulting compound of formula (Xb) with a halogenating agent to give a 3,4-dihalobenzopyran derivative of formula

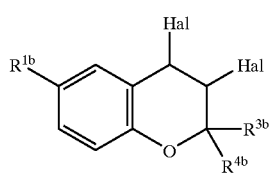
(XIb)

where $R^{1b}$, $R^{3b}$, $R^{4b}$ and Hal have the same meanings as defined above;

(2b-5) treating the resulting compound of formula (XIb) with a base to give a 4-halobenzopyran derivative of formula (Ib) set forth above.

4. A process for producing 4-substituted benzopyran derivatives represented by formula (G-VIc)

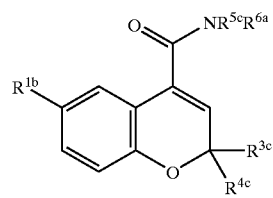
(G-VIc)

where $R^{1b}$ represents a lower perfluoroalkyl croup; $R^{3c}$ and $R^{4c}$, which are the same represent a lower alkyl group or a lower fluoroalkyl group; $R^{5c}$ represents a hydrogen atom and $R^6$ represents an optionally substituted lower alkyl group by scheme (2c) comprising the following steps:

(2c) (2c-1)→(2c-2)→(2c-3)→(2c-4)→(2c-5)→(1c-5);

(2c-1) reacting a compound of formula (IIb)

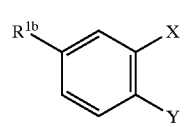
(IIb)

with acetylene of formula (VIIc)

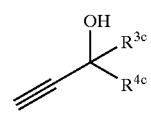
(VIIc)

where $R^{3c}$ and $R^{4c}$ have the same meanings as defined above to give a compound of formula (VIIIc)

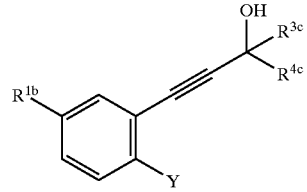
(VIIIc)

where $R^{1b}$, $R^{3c}$ and $R^{4c}$ have the same meanings as defined above; and Y is as defined in claim 1;

(2c-2) treating the resulting compound of formula (VIIIc) with a reducing agent to give a compound of formula (IXc)

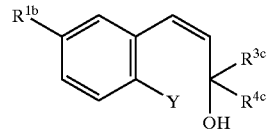
(IXc)

where Y, $R^{1b}$, $R^{3c}$ and $R^{4c}$ have the same meanings as defined above;

(2c-3) reacting the resulting compound of formula (IXc) with a base to give a benzopyran derivative of formula (Xc)

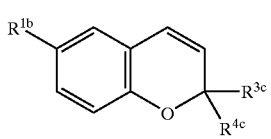

(Xc)

where $R^{1b}$, $R^{3c}$ and $R^{4c}$ have the same meanings as defined above;

(2c-4) reacting the resulting compound of formula (Xc) with a halogenating agent to give a 3,4-dihalobenzopyran derivative of formula

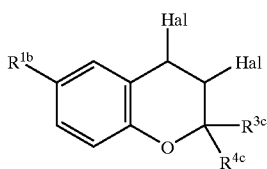

(XIc)

where $R^{1b}$, $R^{3c}$, $R^{4c}$ and Hal have the same meanings as defined above;

(2c-5) treating the resulting compound of formula (XIc) with a base to give a 4-halobenzopyran derivative of formula (1c) set forth above.

5. A process for producing 4-substituted benzopyran derivatives represented by formula (G-VId)

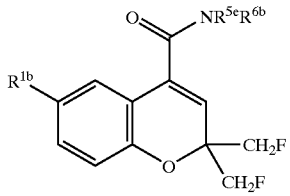

(G-VId)

where $R^{1b}$ represents a lower perfluoroalkyl group; $R^{5c}$ represents a hydrogen atom; and $R^{6b}$ represents a lower alkyl group which may optionally have a cyano group scheme (2d) the following steps:

(2d) (2d-1)→(2d-2)→(2d-3)→(2d-4)→(2d-5)→(1d-5);

(2d-2) treating a compound of formula (VIIId)

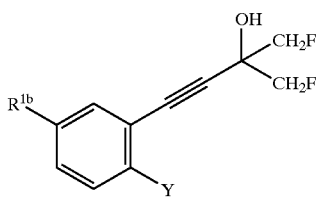

(VIIId)

with a reducing agent to give a compound of formula (IXd)

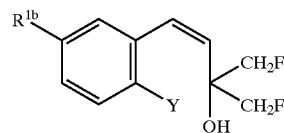

(IXd)

where $R^{1b}$ have the same meaning as defined above; and Y is as defined in claim 1;

(2d-3) reacting the resulting compound of formula (IXd) with a base to give a benzopyran derivative of formula (Xd)

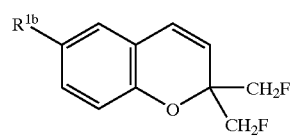

(Xd)

where $R^{1b}$ has the same meaning as defined above;

(2d-4) reacting the resulting compound of formula (Xd) with a halogenating agent to give a 3,4-dihalobenzopyran derivative of formula (XId)

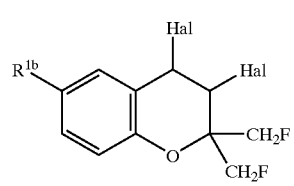

(XId)

where $R^{1b}$ and Hal have the same meanings as defined above;

(2d-5) treating the resulting compound of formula (XId) with a base to give a 4-halobenzopyran derivative of formula (Id)

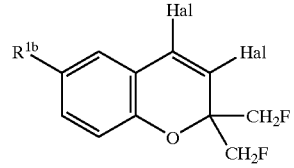

(Id)

where $R^{1b}$ and Hal have the same meanings as defined above.

6. A process for producing 4-substituted benzopyran derivatives represented by formula (G-VIe)

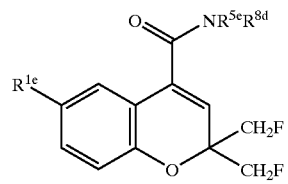

(G-VIe)

where $R^{1e}$ represents a trifluoromethyl group or a pentafluoroethyl group; $R^{5c}$ represents a hydrogen atom; $R^{6d}$ represents a cyanoethyl group by scheme (2e) comprising the following steps:

(2e) (2e-1)→(2e-2)→(2e-3)→(2e-4)→(2e-5)→(1e-5);

(2e-2) treating a compound of formula (VIIIe)

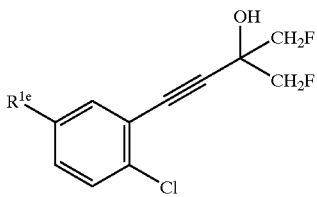

(VIIIe)

with a reducing agent to give a compound of formula (IXe)

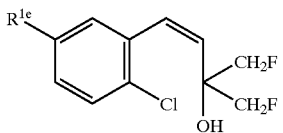

(IXe)

where $R^{1e}$ has the same meaning as defined above;

(2e-3) reacting the resulting compound of formula (IXe) with a base to give a benzopyran derivative of formula (Xd)

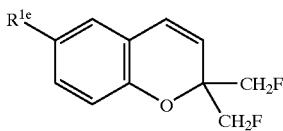

(Xd)

where $R^{1d}$ has the same meaning as defined above:

(2e-4) reacting the resulting compound of formula (Xd) with a halogenating agent to give a 3,4-dihalobenzopyran derivative of formula (XIe)

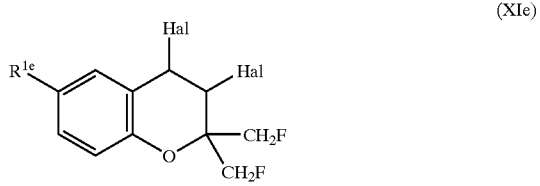

(XIe)

where $R^{1e}$ and Hal have the sane meanings as defined above;

(2e-5) treating the resulting compound of formula (XIe) with a base to give a 4-halobenzopyran derivative of formula (Ie) set forth above.

7. The process according to claim 2 wherein the leaving group is selected from the group consisting of halogen atoms, optionally substituted lower alkylsulfonyloxy groups, and arylsulfonyloxy groups.

8. The process according to claim 3 wherein the leaving group is selected from the group consisting of halogen atoms, optionally substituted lower alkylsulfonyloxy groups, and arylsulfonyloxy groups.

9. The process according to claim 4 wherein the leaving group is selected from the group consisting of halogen atoms, optionally substituted lower alkylsulfonyloxy groups, and arylsulfonyloxy groups.

10. The process according to claim 5 wherein the leaving group is selected from the group consisting of halogen atoms, optionally substituted lower alkylsulfonyloxy groups, and arylsulfonyloxy groups.

* * * * *

UNITED STATES PATENT AND TRADEMARK OFFICE
CERTIFICATE OF CORRECTION

PATENT NO. : 6,455,708 B1
DATED : September 24, 2002
INVENTOR(S) : Yukio Suzuki et al.

It is certified that error appears in the above-identified patent and that said Letters Patent is hereby corrected as shown below:

<u>Title page, Item (54) and Column 1, line 1,</u>
Delete "THE PREPARATION OF" and insert therefor -- PRODUCING --.

Signed and Sealed this

Fourth Day of February, 2003

JAMES E. ROGAN
*Director of the United States Patent and Trademark Office*